US011001542B2

(12) United States Patent
McCormick et al.

(10) Patent No.: US 11,001,542 B2
(45) Date of Patent: May 11, 2021

(54) INTEGRATION OF OXIDATIVE COUPLING OF METHANE PROCESSES

(71) Applicant: Lummus Technology LLC, The Woodlands, TX (US)

(72) Inventors: Jarod McCormick, Palo Alto, CA (US); Guido Radaelli, Pleasant Hill, CA (US); Humera Abdul Rafique, Livermore, CA (US); James Hidajat, South San Francisco, CA (US); Srinivas R. Vuddagiri, Davis, CA (US); Joshua Ryan Miles, San Francisco, CA (US); Richard Black, Houston, TX (US)

(73) Assignee: Lummus Technology LLC, The Woodlands, TX (US)

( * ) Notice: Subject to any disclaimer, the term of this patent is extended or adjusted under 35 U.S.C. 154(b) by 0 days.

(21) Appl. No.: 15/987,068

(22) Filed: May 23, 2018

(65) Prior Publication Data
US 2019/0119182 A1    Apr. 25, 2019

Related U.S. Application Data

(60) Provisional application No. 62/644,098, filed on Mar. 16, 2018, provisional application No. 62/584,441,
(Continued)

(51) Int. Cl.
*C07C 2/84*    (2006.01)
*C07C 2/08*    (2006.01)
(Continued)

(52) U.S. Cl.
CPC ............. *C07C 2/84* (2013.01); *B01J 19/245* (2013.01); *C07C 2/08* (2013.01); *C07C 2/82* (2013.01);
(Continued)

(58) Field of Classification Search
CPC .... C07C 2/08; C07C 2/82; C07C 2/84; C07C 7/04; C07C 7/12; C07C 6/04; C10G 9/00;
(Continued)

(56) References Cited

U.S. PATENT DOCUMENTS 2,324,172 A    7/1943 Parkhurst
2,486,980 A    11/1949 Robinson
(Continued)

FOREIGN PATENT DOCUMENTS

CA    2041874 A1    11/1992
CA    2765769 A1    1/2011
(Continued)

OTHER PUBLICATIONS

Iwamoto, M. One step formation of propene from ethene or ethanol through metathesis on nickel ion-loaded silica. Molecules. Sep. 13, 2011;16(9):7844-63.
(Continued)

*Primary Examiner* — Youngsul Jeong
*Assistant Examiner* — Jason Y Chong
(74) *Attorney, Agent, or Firm* — Calfee, Halter & Griswold LLP

(57) ABSTRACT

The present disclosure provides methods and systems for producing an olefin, such as ethylene and propylene. A method for producing an olefin can comprise injecting an oxidizing agent and methane into an oxidative coupling of methane (OCM) reactor to generate ethylene. The methane and/or additional feedstocks for the OCM reactor can be derived from a thermal cracking or fluidized catalytic cracking (FCC) process. The ethylene generated in the OCM reactor can be converted to propylene through a dimerization unit and metathesis unit.

18 Claims, 23 Drawing Sheets

Related U.S. Application Data filed on Nov. 10, 2017, provisional application No. 62/536,876, filed on Jul. 25, 2017, provisional application No. 62/510,065, filed on May 23, 2017.

(51) Int. Cl.

| | | |
|---|---|---|
| *C07C 6/04* | (2006.01) | |
| *C07C 2/82* | (2006.01) | |
| *C10G 11/05* | (2006.01) | |
| *C10G 70/00* | (2006.01) | |
| *C10G 11/18* | (2006.01) | |
| *C10G 9/00* | (2006.01) | |
| *B01J 19/24* | (2006.01) | |
| *C07C 7/04* | (2006.01) | |
| *C07C 7/12* | (2006.01) | |

(52) U.S. Cl.
CPC .......... *C07C 6/04* (2013.01); *C07C 7/04* (2013.01); *C07C 7/12* (2013.01); *C10G 9/00* (2013.01); *C10G 11/05* (2013.01); *C10G 11/18* (2013.01); *C10G 70/00* (2013.01); *C10G 2400/20* (2013.01)

(58) Field of Classification Search
CPC ........ C10G 11/05; C10G 11/18; C10G 70/00; C10G 2400/20; B01J 19/245
See application file for complete search history.

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hugh, Jr. et al. |
| 3,584,071 A | 6/1971 | Mcnulty et al. |
| 3,596,473 A | 8/1971 | Martin |
| 3,660,519 A | 5/1972 | Takaaki et al. |
| 3,686,334 A | 8/1972 | Britton |
| 3,686,350 A | 8/1972 | Isao et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |

(56) References Cited

U.S. PATENT DOCUMENTS

| | | |
|---|---|---|
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | Devries |
| 5,723,713 A * | 3/1998 | Maunders ............... C07C 2/10 585/329 |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Köster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |

(56) References Cited

U.S. PATENT DOCUMENTS

| | | |
|---|---|---|
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1* | 5/2005 | Sumner ............... C07C 6/04 585/324 |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1* | 5/2007 | Bridges ............... C07C 11/06 585/324 |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1* | 6/2008 | Bozzano ............... C07C 2/06 585/317 |
| 2008/0207975 A1 | 8/2008 | Crone et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0331174 A1 | 12/2010 | Chinta et al. |

(56) References Cited

U.S. PATENT DOCUMENTS

| | | |
|---|---|---|
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0022125 A1* | 1/2017 | Fichtl ........................ C07C 1/24 |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1* | 10/2018 | Takahama ................ B01J 23/44 |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |
| 2020/0207685 A1 | 7/2020 | Nyce et al. |
| 2020/0216370 A1 | 7/2020 | Rafique et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |

(56) References Cited

FOREIGN PATENT DOCUMENTS

| | | | |
|---|---|---|---|
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 0253522 A2 | 1/1988 |
| EP | 0303438 A2 | 2/1989 |
| EP | 336823 A1 | 10/1989 |
| EP | 0608447 A1 | 8/1994 |
| EP | 0634211 A1 | 1/1995 |
| EP | 0722822 A1 | 7/1996 |
| EP | 0761307 A1 | 3/1997 |
| EP | 0764467 A1 | 3/1997 |
| EP | 0716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | WO-8607351 A1 | 12/1986 |
| WO | WO-2002004119 A1 | 1/2002 |
| WO | WO-2004033488 A2 | 4/2004 |
| WO | WO-2004056479 A1 | 7/2004 |
| WO | WO-2004103936 A1 | 12/2004 |
| WO | WO-2005067683 A2 | 7/2005 |
| WO | 2007125360 A1 | 11/2007 |
| WO | WO-2007130515 A2 | 11/2007 |
| WO | WO-2008005055 A2 | 1/2008 |
| WO | WO-2008014841 A1 | 2/2008 |
| WO | WO-2008022147 A1 | 2/2008 |
| WO | WO-2008073143 A2 | 6/2008 |
| WO | 2008150451 A2 | 12/2008 |
| WO | 2008150451 A3 | 3/2009 |
| WO | WO-2009071463 A2 | 6/2009 |
| WO | WO-2009074203 A1 | 6/2009 |
| WO | WO-2009115805 A1 | 9/2009 |
| WO | WO-2010005453 A2 | 1/2010 |
| WO | WO-2011008464 A1 | 1/2011 |
| WO | WO-2011041184 A2 | 4/2011 |
| WO | WO-2011050359 A1 | 4/2011 |
| WO | WO-2010069488 A8 | 5/2011 |
| WO | WO-2011149996 A2 | 12/2011 |
| WO | 2012047274 A2 | 4/2012 |
| WO | 2012047274 A3 | 5/2012 |
| WO | WO-2012162526 A2 | 11/2012 |
| WO | WO-2013106771 A2 | 7/2013 |
| WO | 2013169462 A1 | 11/2013 |
| WO | 2013175204 A1 | 11/2013 |
| WO | WO-2013177433 A2 | 11/2013 |
| WO | WO-2013177431 A2 | 11/2013 |
| WO | WO-2014011646 A1 | 1/2014 |
| WO | 2014044387 A1 | 3/2014 |
| WO | WO-2014049445 A2 | 4/2014 |
| WO | 2014089479 A1 | 6/2014 |
| WO | 2013177433 A3 | 8/2014 |
| WO | 2014131435 A1 | 9/2014 |
| WO | WO-2014143880 A1 | 9/2014 |
| WO | 2015000061 A1 | 1/2015 |
| WO | 2015003193 A2 | 1/2015 |
| WO | 2015021177 A1 | 2/2015 |
| WO | WO-2015048295 A1 | 4/2015 |
| WO | WO-2015066693 A1 | 5/2015 |
| WO | WO-2015081122 A2 | 6/2015 |
| WO | WO-2015105911 A1 | 7/2015 |
| WO | WO-2015106023 A1 | 7/2015 |
| WO | WO-2015081122 A3 | 12/2015 |
| WO | WO-2016012371 A1 | 1/2016 |
| WO | WO-2016149507 A1 | 9/2016 |
| WO | WO-2016160563 A1 | 10/2016 |
| WO | 2016205411 A2 | 12/2016 |
| WO | 2016210006 A2 | 12/2016 |
| WO | 2016210006 A3 | 4/2017 |
| WO | WO-2017065947 A1 | 4/2017 |
| WO | 2016205411 A3 | 9/2017 |
| WO | WO-2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | WO-2018118105 A1 | 6/2018 |
| WO | 2019010498 A1 | 1/2019 |
| WO | 2019055220 A1 | 3/2019 |

OTHER PUBLICATIONS

Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.

Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.

Process Systems; "Steam Tables" Apr. 8, 2017—https://web.archive.org/web/20170408152403/https://valvesonline.com.au/references/steam-tables/.

Ahari, et al. Effects of operating parameters on oxidative coupling of methane over Na—W—Mn/SiO2 catalyst at elevated pressures. Journal of Natural Gas Chemistry. vol. 20, Issue 2, Mar. 2011, pp. 204-213.

PCT/US2018/041322 International Search Report and Written Opinion dated Sep. 24, 2018.

PCT/US2018/34184 International Search Report and Written Opinion dated Sep. 26, 2018.

U.S. Appl. No. 15/272,205 Office Action dated Sep. 25, 2018.

U.S. Appl. No. 15/354,886 Office Action dated Aug. 31, 2018.

U.S. Appl. No. 16/021,441 Office Action dated Aug. 28, 2018.

Agarwal, et al., Aqueous Au—Pd colloids catalyze selective CH4 oxidation to CH3OH with O2 under mild conditions, Science 358, Oct. 13, 2017, 223-27.

American Petroleum Institute Publication 534 "Heat Recovery Steam Generators" Jan. 1995 (51 pages).

Autothermal Partial Oxidative Coupling of Methane. IP.com, Prior Art Database Technical Disclosure, Jul. 29, 2008, 5 pages.

Barrett, et al. The determination of pore volume and area distributions in porous substances—Compuatations from nitrogen isotherms. J. Am. Chem. Soc., 1951, vol. 73, pp. 373-380.

Berstad, D. et al. Low-temperature CO2 removal from natural gas. Energy Procedia (2012) 26:41-48.

Bloch, et al. Hydrocarbon Separations in a Metal-Organic Framework with Open Iron(II) Coordination Sites, Science, 2012, 335:1606-1610.

Bollmann, et al. Ethylene tetramerization: a new route to produce 1-octene in exceptionally high selectivities. J Am Chem Soc. Nov. 17, 2004;126(45):14712-3.

Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.

Carter, et al. High activity ethylene trimerisation catalysts based on diphosphine ligands. Chem Commun (Camb). Apr. 21, 2002;(8):858-9.

Cavani, et al. Oxidative dehydrogenation of ethane and propane: How far from commercial implementation? Catalysis Today. 2007; 127(1-4):113-131.

Chemsystems PERP Report Ethylene Oxide/Ethylene Glycol 2005.

Chen, et al. M2 Forming—A Process for Aromatization of Light Hydrocarbons. Ind. Eng. Chem. Process. Des. Dev. 1986, 25, 151-155.

(56) References Cited

OTHER PUBLICATIONS

Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): Feb. 15-25, 2004.
Choudhary, et al. Surface Basicity and Acidity of Alkaline Earth-Promoted $La_2 O_3$ Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Co-pending U.S. Appl. No. 15/359,399, filed Nov. 22, 2016.
Co-pending U.S. Appl. No. 15/699,798, filed Sep. 8, 2017.
Co-pending U.S. Appl. No. 15/888,777, filed Feb. 5, 2018.
Co-pending U.S. Appl. No. 15/912,104, filed Mar. 5, 2018.
Co-pending U.S. Appl. No. 15/950,461, filed Apr. 11, 2018.
Co-pending U.S. Appl. No. 16/021,441, filed Jun. 28, 2018.
Co-pending U.S. Appl. No. 16/030,298, filed Jul. 9, 2018.
Co-pending U.S. Appl. No. 16/035,311, filed Jul. 13, 2018.
Debart, et al. $\alpha$-MNO2 Nanowires: A catalyst for the O2 Electrode in Rechargeabl Lithium Batteries. Angewandte Chemie International Edition 47: 4521-4524, 2008.
Enger, et al. A review of catalytic partial oxidation of methane to synthesis gas with emphasis on reaction mechanisms over transition metal catalysts. Applied Catalysis A: General 346 (1-2): Aug. 1-27, 2008.
European search report and search opinion dated Jan. 20, 2016 for EP Application No. 13817389.3.
Extended European search report and opinion dated Jul. 19, 2017 for EP Application No. 15734911.9.
Fallah, et al., A New Nano-(2Li2O/MgO) Catalyst/Porous Alpha-Alumina Composite for the Oxidative Coupling of Methane Reaction, AIChE Journal, Mar. 2010, 56(3):717-28.
Gao, et al. A study on methanol steam reforming to CO2 and H2 over the La2 CO4 nanofiber catalyst. Journal of Solid State Chemistry 181: 7-13, 2008.
Gao, et al. The direct decomposition of NO over the La2 CuO4 nanofiber catalyst. Journal of Solid State Chemistry 181: 2804-2807, 2008.
Ghosh, et al., Absorption of carbon dioxide into aqueous potassium carbonate promoted by boric acid, Energy Procedia, Feb. 2009, pp. 1075-1081.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): Feb. 1-15, 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale—Electronic Supplementary Material, 2013, 7 pages.
Huang, et al. Exploiting shape effects of $La_2 O_3$ nanocrystals for oxidative coupling of methane reaction. Nanoscale 5(22): 10844-10848, 2013.
International preliminary report on patentability dated Jul. 21, 2016 for PCT Application No. US2015/010688.
International search report and written opinion dated Mar. 6, 2014 for PCT/US2013/042480.

International search report and written opinion dated Mar. 17, 2014 for PCT Application No. US2013/021312.
International search report and written opinion dated Jun. 12, 2015 for PCT Application No. US2015/010688.
International search report and written opinion dated Aug. 11, 2016 for PCT/US2016/024195.
International search report and written opinion dated Aug. 16, 2017 for PCT Application US-2017027483.
International search report and written opinion dated Aug. 18, 2016 for PCT/US2016/022891.
International search report and written opinion dated Sep. 5, 2017 for PCT Application US-2017025544.
International search report and written opinion dated Nov. 1, 2013 for PCT/US2013/049742.
International search report and written opinion dated Nov. 11, 2015 for PCT Application No. US2014/067465.
International search report and written opinion dated Feb. 2, 2017 for PCT Application No. US-2016052959.
International search report dated Mar. 19, 2014 for PCT Application No. US2013/073657.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, et al. Synthesis of Ethylene via Oxidative Coupling of Methane. Journal of Catalysis 73: 9-19, 1982.
Keller, Gas-Adsorption Processes: State of the Art, American Chemical Society, 1983, pp. 145-169.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Li, et al. Combined Single-Pass Conversion of Methane Via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core—A Ushell Nanowires and Their Surface Enhanced Raman Spectroscopic Studies. Acta Chimica Sinica. 65 (9): 779-784, 2007.
Liu, et al. A novel Na2 WO4-Mn.SiC monolithic foam catalyst with improved thermal properties for the oxidative coupling of methane. Catalysis Communications 9: 1302-1306, 2008.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.

(56) References Cited

OTHER PUBLICATIONS

Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Niu, et al. Preparation and characterization of La2 $O_3CO_3$ nanowires with high surface areas. Jounral of the Chinese Rare Earth Society 23 (Spec. Issue): 33-36, Dec. 2005.
Notice of allowance dated Sep. 9, 2016 for U.S. Appl. No. 15/076,480.
Notice of allowance dated Oct. 6, 2016 for U.S. Appl. No. 15/076,480.
Notice of allowance dated Jan. 4, 2016 for U.S. Appl. No. 14/789,953.
Notice of allowance dated Jan. 10, 2017 for U.S. Appl. No. 15/076,480.
Notice of allowance dated Jan. 13, 2016 for U.S. Appl. No. 14/789,946.
Notice of allowance dated Mar. 15, 2017 for U.S. Appl. No. 13/936,783.
Notice of allowance dated Apr. 27, 2016 for U.S. Appl. No. 13/900,898.
Notice of allowance dated May 16, 2017 for U.S. Appl. No. 14/592,668.
Notice of allowance dated Jun. 8, 2015 for U.S. Appl. No. 13/739,954.
Notice of allowance dated Aug. 9, 2016 for U.S. Appl. No. 15/076,480.
Notice of allowance dated Aug. 10, 2017 for U.S. Appl. No. 15/341,551.
Notice of allowance dated Aug. 11, 2016 for U.S. Appl. No. 13/900,898.
Notice of allowance dated Aug. 22, 2016 for U.S. Appl. No. 14/820,460.
Notice of Allowance dated Sep. 21, 2017 for U.S. Appl. No. 15/341,551.
Notice of allowance dated Sep. 22, 2016 for U.S. Appl. No. 13/936,870.
Notice of allowance dated Oct. 24, 2016 for U.S. Appl. No. 14/789,901.
Notice of allowance dated Dec. 5, 2016 for U.S. Appl. No. 15/076,480.
Nyce, et al. PCT/US2015/010525 filed Jan. 7, 2015 for Ethylene-to-Liquids Systems and Methods.
Office action dated Jan. 14, 2016 for U.S. Appl. No. 13/936,870.
Office Action dated Jan. 25, 2018 for U.S. Appl. No. 15/354,886.
Office action dated Mar. 6, 2017 for U.S. Appl. No. 13/936,870.
Office action dated Mar. 16, 2016 for U.S. Appl. No. 14/789,901.
Office action dated Apr. 22, 2016 for U.S. Appl. No. 15/076.480.
Office action dated May 20, 2016 for U.S. Appl. No. 14/820,460.
Office action dated Jul. 21, 2017 for U.S. Appl. No. 15/076,402.
Office action dated Jul. 29, 2016 for U.S. Appl. No. 14/789,901.
Office action dated Sep. 6, 2017 for U.S. Appl. No. 13/936,870.
Office action dated Sep. 11, 2015 for U.S. Appl. No. 14/789,946.
Office action dated Sep. 11, 2015 for U.S. Appl. No. 14/789,953.
Office action dated Oct. 4, 2016 for U.S. Appl. No. 15/076,402.
Office action dated Oct. 23, 2014 for U.S. Appl. No. 13/739,954.
Office Action dated Oct. 27, 2017 for U.S. Appl. No. 14/553,795.
Office action dated Nov. 2, 2015 for U.S. Appl. No. 14/789,901.
Office Action dated Nov. 6, 2017 for U.S. Appl. No. 14/868,911.
Office action dated Nov. 7, 2016 for U.S. Appl. No. 13/936,783.
Office action dated Nov. 13, 2015 for U.S. Appl. No. 13/900,898.
Office Action dated Nov. 30, 2017 for U.S. Appl. No. 15/272,205.
Office action dated Dec. 23, 2015 for U.S. Appl. No. 13/936,783.
Office action dated Dec. 23, 2016 for U.S. Appl. No. 14/592,668.
Office action dated Jan. 26, 2017 for U.S. Appl. No. 15/341,551.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Pak, et al. Elementary Reactions in the Oxidative Coupling of Methane over Mn/NA2 WO4/SiO2 and Mn/NA2 WO4/MgO Catalysts. Journal of Catalysis 179:222-230, 1998.
Lunsford, et al. The oxidative coupling of methane on chlorinated Lithium-doped magnesium oxide. J. Chem. Soc., Chem. Commun., 1991, 1430-1432.
Qiu, et al. Steady-state conversion of methane to aromatics in high yields using an integrated recycle reaction system. Catalysis Letters 48: 11-15, 1997.
Rafique, et al. PCT/US2015/010688 filed Jan. 8, 2015 for "Oxidative Coupling of Methane Implementations for Olefin Production".
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK-Conference, Hamburg, Germany (2007).
Sheridan, D. et al. PCT/US2014/067465 filed Nov. 25, 2014 for "Integrated Mixers and Heat Exchangers for Oxidative Coupling Methane Systems".
Simons, K. Membrane Technologies for CO2 Capture. Dissertation, U. of Twente (2010).
Smith, et al. Recent developments in solvent absorption technologies at the CO2CRC in Australia. Energy Procedia 1(2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Takanabe, et al. Mechanistic Aspects and Reaction Pathways for Oxidative Coupling of Methane on Mn/NA2WO4/SiO2 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 WO4/SiO2 . Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Supplementary European search report dated Jun. 27, 2017 for EP Application No. 14866399.
U.S. Appl. No. 13/936,870 Notice of Allowance dated Mar. 21, 2018.
U.S. Appl. No. 62/050,729, filed Sep. 15, 2014.
U.S. Appl. No. 62/073,478, filed Oct. 31, 2014.
U.S. Appl. No. 15/888,777 Office Action dated Apr. 26, 2018.
U.S. Appl. No. 14/553,795 Notice of Allowance dated May 25, 2018.
U.S. Appl. No. 14/868,911 Office Action dated May 29, 2018.
U.S. Appl. No. 15/076,402 Office Action dated Mar. 8, 2018.
U.S. Appl. No. 15/356,202 Office Action dated Apr. 26, 2018.
U.S. Appl. No. 15/476,889 Office Action dated Apr. 30, 2018.
U.S. Appl. No. 15/487,181 Corrected Notice of Allowability dated Mar. 1, 2018.
U.S. Appl. No. 15/487,181 Notice of Allowability dated Feb. 13, 2018.
U.S. Appl. No. 15/487,181 Notice of Allowance dated Jan. 30, 2018.
U.S. Appl. No. 15/487,181 Supplemental Notice of Allowability dated Feb. 7, 2018.

(56) References Cited

OTHER PUBLICATIONS

Wang, et al. Autothermal oxidative coupling of methane on the $SrCO_3/Sm_2O_3$ catalysts. Catalysis communications 10: 807-810, 2009.
Wang, et al. Comparative study on oxidation of methane to ethane and ethylene over NA2 WO4-Mn/SiO2 catalysts prepared by different methods. Journal of Molecular Catalysis A: Chemical 245:272-277, 2006.
Wang, et al., Critical Influence of BaC03 on Low Temperature Catalytic Activity of BaC03/Zr02 Catalysts for Oxidative Coupling of Methane, Catalysis Letters (2009), 129:156-162.
Wang, et al. Low temperature selective oxidation of methane to ethane and ethylene over $BaCO_3/La_2O_3$ catalysts prepared by urea combustion method. Catalysis communications 7: 5963, 2006.
Water Electrolysis & Renewable Energy Systems. FuelCellToday (May 2013).
Wikipedia search, Adiabatic Process, Mar. 2011, 10 pages.
Witek-Krowiak, A. et al. Carbon Dioxide Removal in a Membrane Contactor—Selection of Absorptive Liquid/Membrane System. Intl J Chem Eng and Appl. (2012) 3(6):391-395.
Wong, et al. Oxidative coupling of methane over alkali metal oxide promoted $La2 O_3/BaCO_3$ cataylsts. J. Chem. Tech. Biotechnol. 65:351-354, 1996.
Xu, et al. Maximise ethylene gain and acetylene selective hydrogenation efficiency. Petroleum technology quarterly 18.3 (2013): 39-42.
Xu, G. et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires. Nanotechnology 17: 2304-2310, 2006.
Yu, et al. Oxidative coupling of methane over acceptor-doped SrTi $O_3$: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.
Zhou. BP-UOP Cyclar Process. Handbook of Petroleum Refining Processes, The McGraw-Hill Companies (2004), pp. 2.29-2.38.
Zhou, et al. Functionalization of lanthanum hydroxide nanowires by atom transfer radical polymerization. Nanotechnology 18, 2007, 7 pages.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
Co-pending U.S. Appl. No. 15/581,996, filed Apr. 28, 2017.
Duan, et al. Three-dimensional copper (II) metal-organic framework with open metal sites and anthracene nucleus for highly selective C2H2/CH4 and C2NH2/CO2 gas separation at room temperature. Microporous and Mesoporous Materials. vol. 181, Nov. 15, 2013, pp. 99-104.
He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.

Chemical Engineering—"Separation Processes: Supercritical CO2: A Green Solvent" Feb. 1, 2010.
Caskey, et al., Dramatic Tuning of Carbon Dioxide Uptake via Metal Substitution in a Coordination Polymer with Cylindrical Pores, J. Am. Chem. Soc., (2009), 130(33): 10870-71.
Corma, From Microporous to Mesoporous Molecular Sieve Materials and Their Use in Catalysis, Chern. Rev., 97, 1997, pp. 2373-2419.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Geier, et al., Selective adsorption of ethylene over ethane and propylene over propane in the metal-organic frameworks M2(dobdc) (M = Mg, Mn, Fe, Co, Ni, Zn), Chem. Sci., 2013, 4:2054-2061.
Godini, et al. Techno-economic analysis of integrating the methane oxidative coupling and methane reforming processes. Fuel processing technology 2013 v.106 pp. 684-694.
Goto et al, Mesoporous Material from Zeolite, Journal of Poruous Materials, 2002, pp. 43-48.
Haag, W.O. et al. Aromatics, Light Olefins and Gasoline from Methanol: Mechanistic Pathways with ZSM-5 Zeolite Catalyst. J Mol Catalysis (1982) 17:161-169.
Liu, et al. Increasing the Density of Adsorbed Hydrogen with Coordinatively Unsaturated Metal Centers in Metal-Organic Frameworks Langmuir, 2008, 24:4772-77.
Makal, et al., Methane storage in advanced porous materials, Critical Review, Chem. Soc. Rev., 2012, 41 :7761-7779.
Mokhatab et al. "Handbook of Natural Gas Transmission and Processing: Principles and Practices" 2015. Chapter 7, pp. 237-242. (Year 2015).
Morgan, C.R. et al. Gasoline from Alcohols. Ind Eng Chem Prod Res Dev(1981) 20:185-190.
Ogura et al. Formation of Uniform Mesopores in ZSM-5 Zeolite through Treatment in Alkaline Solution, Chemistry Letters, 2000, pp. 882-883.
Olefins Conversion Technology, Website Accessed Aug. 28, 2014, http:www.CBI.com.
Tabak, S.A. et al. Conversion of Methanol over ZSM-5 to Fuels and Chemicals. Cat Today (1990) 307-327.
Wu, et al., High-Capacity Methane Storage in Metal-Organic Frameworks M2(dhtp): The Important Role of Open Metal Sites, J. Am. Chem. Soc. 131 (13):4995-5000.
Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.
PCT/US2018/34184 International Preliminary Report on Patentability dated Dec. 5, 2019.
Examination Report dated Dec. 23, 2019 for GCC Patent Application No. GC 2018-35369.
Extended European Search Report dated Jan. 22, 2021 for EP Application No. 18806030.5.
Examination Report dated Jan. 14, 2021 for GCC Patent Application No. GC 2018-35369.

\* cited by examiner

INTEGRATION OF OXIDATIVE COUPLING OF METHANE PROCESSES

CROSS-REFERENCE

This application claims the benefit of U.S. Provisional Patent Application No. 62/510,065, filed May 23, 2017, U.S. Provisional Patent Application No. 62/536,876, filed Jul. 25, 2017, U.S. Provisional Patent Application No. 62/584,441, filed Nov. 10, 2017, and U.S. Provisional Patent Application No. 62/644,098, filed Mar. 16, 2018, each of which is incorporated herein by reference in its entirety.

BACKGROUND

Olefins, including ethylene and propylene, are important feedstocks in the chemicals industry. Olefins can be generated from the cracking of high molecular weight hydrocarbon streams into lower molecular weight streams. Additionally olefins can be interconverted among species with various numbers of carbon atoms through chemical tranformations.

SUMMARY

Recognized herein is a need for efficient and commercially viable olefin production systems and methods for converting alkanes into olefins when coupled to crude to chemicals (C2C) processes such as high-severity fluidized catalytic cracking (HS-FCC) processes and processes employing dimerization and metathesis operations.

The present disclosure provides systems and methods for generating olefins, including ethylene and propylene, through the integration of an oxidative-coupling of methane (OCM) process with an additional process that can either provide the feedstock for the OCM process or can consume the products of the OCM process.

An aspect of the present disclosure provides a method for producing propylene, the method comprising: (a) injecting a first stream containing methane ($CH_4$) and a second stream containing an oxidizing agent into an oxidative coupling of methane (OCM) reactor at a temperature of at least about 400° C. and a pressure of at least about 3 bar(g) to produce an OCM product stream containing ethylene, hydrogen ($H_2$), carbon dioxide ($CO_2$), carbon monoxide (CO), and unconverted $CH_4$; (b) injecting at least a portion of the OCM product stream into a dimerization reactor to produce butene, wherein less than about 50% of the butene is isobutene; and (c) injecting the butene into a metathesis reactor to produce an effluent stream comprising propylene and unconverted butene.

In some embodiments, (b) and (c) are performed in a single vessel. In some embodiments, dimerization and metathesis are performed in a single reactor or over a single catalyst. In some embodiments, at least about 50% of the butene is 1-butene or 2-butene. In some embodiments, a portion of the ethylene produced in the OCM reactor is injected into the dimerization reactor, and an additional portion of the ethylene produced in the OCM reactor is injected into the metathesis reactor. In some embodiments, about 70% of the ethylene produced in the OCM reactor is injected into the dimerization reactor, and about 30% of the ethylene produced in the OCM reactor is injected into the metathesis reactor. In some embodiments, substantially no ethylene is injected into metathesis reactor without first being injected into the dimerization reactor. In some embodiments, the butene produced in the dimerization reactor contains $C_{5+}$ compounds, and wherein the $C_{5+}$ compounds are removed using a de-butanizer prior to (c). In some embodiments, the ethylene is separated from $C_{3+}$ components in the effluent stream of the metathesis reactor. In some embodiments, a portion of the separated ethylene is recycled to the metathesis reactor. In some embodiments, the propylene in the effluent stream of the metathesis reactor is separated from the unconverted butene. In some embodiments, the unconverted butene is recycled to the metathesis reactor. In some embodiments, the ethylene that is injected into the dimerization reactor has a purity of at least about 99.5 mol %. In some embodiments, at least about 95% of the ethylene is converted into butenes in the dimerization reactor. In some embodiments, the butene that is injected into the metathesis reactor further comprises un-converted ethylene, which unconverted ethylene is passed through the dimerization reactor without being converted to butene. In some embodiments, the unconverted ethylene is about the only ethylene that is injected into the metathesis reactor. In some embodiments, the unconverted methane from the OCM reactor is removed through a vacuum pressure swing adsorption (VPSA) process to produce a VPSA effluent stream that contains less than about 1% methane. In some embodiments, the VPSA effluent stream is injected into a distillation column that removes $C_{3+}$ species to generate a distillation effluent stream that has a higher concentration of ethylene than the VPSA effluent stream. In some embodiments, the propylene generated in the metathesis reactor is also separated using the distillation column that removes the $C_{3+}$ species. In some embodiments, the butene produced in the dimerization reactor is injected, without prior purification, into the metathesis reactor. In some embodiments, the method further comprises injecting ethane into the OCM reactor in (a). In some embodiments, the method further comprises injecting propane into the OCM reactor in (a). In some embodiments, the method further comprises separating the ethylene produced in the OCM reactor in (a) from ethane, methane, and hydrogen comprised in the OCM product stream. In some embodiments, the $CO_2$ is separated from the OCM product stream. In some embodiments, the $CO_2$ is injected into a methanation reactor to produce additional $CH_4$. In some embodiments, the additional $CH_4$ produced in the methanation reactor is injected into the OCM reactor. In some embodiments, distillation is used to purify the ethylene from the OCM product stream. In some embodiments, pressure swing adsorption is used to purify the ethylene from the OCM product stream. In some embodiments, a C1 splitter is used to recycle the methane back to the OCM reactor. In some embodiments, a C2 splitter is used to recycle the ethane back to the OCM reactor. In some embodiments, the methane recovered from the pressure swing adsorption is recycled to the OCM reactor. In some embodiments, the dimerization reactor contains a dimerization catalyst. In some embodiments, the OCM reactor contains an OCM catalyst. In some embodiments, the OCM catalyst comprises nanowires. In some embodiments, the method further comprises separating the effluent stream of the metathesis reactor. In some embodiments, distillation is used to purify the effluent stream. In some embodiments, ethylene and ethane are separated from $C_{3+}$ products in a distillation column. In some embodiments, propylene and propane are separated in a distillation column. In some embodiments, the metathesis reactor reacts ethylene with butene to generate propylene. In some embodiments, butene reacts with butene to generate propylene.

Another aspect of the present disclosure provides a method for producing propylene, the method comprising: (a) injecting a first stream containing methane and a second stream containing an oxidizing agent into an oxidative coupling of methane (OCM) reactor to produce a stream containing ethylene; (b) injecting the ethylene into a dimerization reactor to produce butenes including 1-butene, 2-butene, and isobutene; and (c) injecting the butenes into a metathesis reactor to produce an effluent comprising propylene and unreacted butenes, wherein in the metathesis reactor the 1-butene and 2-butene metathesize to produce the propylene, and wherein the ethylene is not injected directly into the metathesis reactor.

In some embodiments, the method further comprises: (d) recycling a portion of the unreacted butenes to the metathesis reactor. In some embodiments, less than about 50% of the unreacted butenes are recycled to the metathesis reactor. In some embodiments, the method further comprises injecting ethane into the OCM reactor in (a). In some embodiments, the method further comprises injecting propane into the OCM reactor in (a). In some embodiments, the method further comprises separating the ethylene produced in the OCM reactor in (a) from other components comprising $CO_2$, CO, $H_2$, and unreacted $CH_4$ comprised in the stream. In some embodiments, the $CO_2$ is separated from the stream. In some embodiments, the $CO_2$ is injected into a methanation reactor to produce additional $CH_4$. In some embodiments, the additional $CH_4$ is injected into the OCM reactor. In some embodiments, distillation is used to purify the ethylene from the stream. In some embodiments, pressure swing adsorption is used to purify the ethylene from the stream. In some embodiments, a C1 splitter is used to recycle methane back to the OCM reactor. In some embodiments, a C2 splitter is used to recycle ethane back to the OCM reactor. In some embodiments, methane recovered from the pressure swing adsorption is recycled to the OCM reactor. In some embodiments, a debutenizer is used to extract $C_{5+}$ products from the dimerization reactor in (b). In some embodiments, the debutenizer is a distillation column. In some embodiments, the dimerization reactor contains a dimerization catalyst. In some embodiments, the OCM reactor contains an OCM catalyst. In some embodiments, the OCM catalyst comprises nanowires. In some embodiments, the method further comprises purifying the effluent of the metathesis reactor. In some embodiments, distillation is used to purify the effluent. In some embodiments, the purifying comprises separating ethylene and ethane from $C_{3+}$ components in a distillation column. In some embodiments, the purifying comprises separating propylene and propane in a distillation column. In some embodiments, the butenes are not purified prior to injection in the metathesis reactor. In some embodiments, the effluent of the metathesis reactor is injected into the distillation column. In some embodiments, the separated $C_{3+}$ components are fed into a stabilizer to remove $C_{4+}$ components from propylene and propane. In some embodiments, the propylene is separated from the propane in the distillation column. In some embodiments, at least about 90% of the propylene generated in the metathesis reactor is included in an effluent stream of the distillation column.

Another aspect of the present disclosure provides a system for producing propylene, comprising: (a) at least one oxidative-coupling of methane (OCM) subsystem that (i) has a first input stream comprising methane ($CH_4$), (ii) has a second input feed stream comprising an oxidizing agent, and (iii) is configured to generate from the methane and the oxidizing agent a product stream comprising ethylene; (b) at least one first purification subsystem that is downstream of, and fluidically coupled to, the OCM subsystem, which at least one first purification subsystem is configured to use the product stream of the OCM subsystem to produce an ethylene stream having a higher concentration of ethylene than the product stream; (c) at least one dimerization subsystem downstream of, and fluidically coupled to, the at least one first purification subsystem, wherein the at least one dimerization subsystem is capable of converting the ethylene stream into a stream containing butenes; (d) at least one metathesis subsystem downstream of, and fluidically coupled to, the at least one dimerization subsystem, wherein the at least one metathesis subsystem is configured to convert the stream containing the butenes including 1-butene and 2-butene into a metathesis product stream containing propylene and unconverted butenes; and (e) at least one second purification subsystem that is downstream of, and fluidically coupled to, the at least one metathesis subsystem, which at least one second purification subsystem is configured to separate the unconverted butenes from the propylene.

In some embodiments, the system further comprises: a recycle loop that is fluidically coupled to the at least one second purification subsystem and the at least one dimerization subsystem, which recycle loop is configured to return the unconverted butenes from the at least one second purification subsystem to the at least one dimerization subsystem. In some embodiments, the recycle loop diverts at least about 50% of the unconverted butenes away from the at least one metathesis subsystem. In some embodiments, the at least one OCM subsystem contains an OCM reactor. In some embodiments, the OCM reactor contains an OCM catalyst. In some embodiments, the OCM catalyst comprises nanowires. In some embodiments, the at least one first purification subsystem is configured to remove $CO_2$ from the product stream of the OCM subsystem. In some embodiments, the at least one first purification subsystem is configured to feed the $CO_2$ into a methanation reactor. In some embodiments, the at least one first purification subsystem contains a subsystem that removes methane from the product stream of the OCM subsystem. In some embodiments, the subsystem comprises at least one demethanizer. In some embodiments, the demethanizer is a distillation column. In some embodiments, the subsystem comprises a pressure swing adsorption unit. In some embodiments, the at least one first purification subsystem contains a subsystem that removes ethane from the product stream of the OCM subsystem. In some embodiments, the subsystem comprises at least one C2 splitter. In some embodiments, the at least one C2 splitter comprises a distillation column. In some embodiments, the at least one second purification subsystem comprises a distillation column. In some embodiments, the at least one first purification subsystem and the at least one second purification subsystem are the same. In some embodiments, the system does not contain a purification subsystem that is capable of changing a composition of the stream of the at least one dimerization reactor prior to being injected in the at least one metathesis reactor.

Another aspect of the present disclosure provides a method for producing olefins, the method comprising: (a) injecting a feed stream containing a mixture of hydrocarbons having a first average molecular weight into a vessel operating at a temperature of at least about 500° C., thereby producing a cracked hydrocarbon stream containing a mixture of hydrocarbons having a second average molecular weight, wherein the second average molecular weight is less than the first average molecular weight; (b) separating one or more light hydrocarbons from the cracked hydrocarbon stream; and (c) injecting the one or more light hydrocarbons separated in (b) into an oxidative coupling of methane (OCM) reactor that converts at least a portion of the one or more light hydrocarbons into ethylene.

In some embodiments, the one or more light hydrocarbons comprise hydrogen sulfide ($H_2S$). In some embodiments, the $H_2S$ constitutes at least about 5 percent by weight (wt %) of the light hydrocarbons. In some embodiments, the vessel is a thermal cracker. In some embodiments, the vessel is a fluidized catalytic cracker (FCC). In some embodiments, the FCC is operated as a high-severity fluidized catalytic cracker (HS-FCC). In some embodiments, the HS-FCC operates at a temperature of at least about 500° C. In some embodiments, the HS-FCC contains a catalyst that moves relative to the vessel. In some embodiments, the catalyst is injected into a top portion of the vessel and falls to a bottom portion of the vessel. In some embodiments, the catalyst comprises a zeolite. In some embodiments, the zeolite is ZSM-5. In some embodiments, the HS-FCC operates with a residence time of less than about 1 second (s), and wherein the residence time is a period of time that passes between the feed stream entering the vessel and the cracked hydrocarbon stream exiting the vessel. In some embodiments, the one or more light hydrocarbons include hydrocarbons having one to three carbon atoms (C1-C3 hydrocarbons). In some embodiments, the one or more light hydrocarbons include methane. In some embodiments, the one or more light hydrocarbons include ethane. In some embodiments, the one or more light hydrocarbons include propane. In some embodiments, methane from the HS-FCC is fed into the OCM reactor. In some embodiments, ethane from the HS-FCC is fed into the OCM reactor. In some embodiments, propane from the HS-FCC is fed into the OCM reactor. In some embodiments, the ethylene is included in a product stream from the OCM reactor, and wherein the product stream is used to generate an ethylene stream that has a higher concentration of ethylene than the product stream. In some embodiments, the OCM reactor produces $CO_2$, which $CO_2$ is separated from the ethylene. In some embodiments, the $CO_2$ is injected into a methanation reactor to produce additional $CH_4$. In some embodiments, the additional $CH_4$ is injected into the OCM reactor. In some embodiments, pressure swing adsorption is used to generate an ethylene stream from the OCM reactor. In some embodiments, a C1 splitter is used to recycle methane back to the OCM reactor. In some embodiments, methane recovered from the pressure swing adsorption is recycled to the OCM reactor. In some embodiments, the thermal cracker is operated at a pressure of at least about 3 bar(g). In some embodiments, the FCC contains a catalyst. In some embodiments, the catalyst comprises a zeolite. In some embodiments, the zeolite comprises a high USY zeolite. In some embodiments, the zeolite comprises ZSM-5 zeolites. In some embodiments, the OCM reactor contains an OCM catalyst. In some embodiments, the OCM catalyst comprises nanowires.

Another aspect of the present disclosure provides a system for producing olefins, comprising: a fluidized catalytic cracker (FCC) unit containing a catalyst that is movable downward through the FCC unit; a first separations subsystem fluidically coupled to the FCC unit, which first separations subsystem is configured to separate components that have a boiling point greater than that of propane from those with a boiling point lower than that of propane; a second separations subsystem fluidically coupled to the FCC unit, the second separations subsystem configured to remove hydrogen sulfide ($H_2S$); and an oxidative-coupling of methane (OCM) unit fluidically coupled to the FCC unit and configured to convert the components that have a boiling point lower than that of propane into ethylene.

In some embodiments, the FCC unit is a high-severity FCC (HS-FCC) unit. In some embodiments, the FCC unit operates at temperatures of at least about 500° C. In some embodiments, the FCC unit operates with a residence time of less than about 1 second (s). In some embodiments, the catalyst in the FCC unit comprises a zeolite. In some embodiments, the system further comprises a heat recovery subsystem, which is downstream of and fluidically coupled to the OCM unit, the heat recovery system configured to transfer heat from the OCM unit to another heat transfer medium. In some embodiments, the system further comprises a process gas compressor, which is downstream of and fluidically coupled to the heat recovery subsystem, the process gas compressor configured to increase a pressure of an OCM gas exiting the OCM unit. In some embodiments, the system further comprises a $CO_2$ separation subsystem, which is downstream of and fluidically coupled to the process gas compressor, the $CO_2$ separation subsystem configured to remove $CO_2$ from an OCM gas exiting the OCM unit. In some embodiments, the $CO_2$ separation subsystem comprises an absorber unit. In some embodiments, the $CO_2$ separation subsystem comprises a pressure-swing adsorption unit. In some embodiments, the system further comprises a demethenation subsystem, which is downstream of and fluidically coupled to the $CO_2$ separation subsystem, the demethenation subsystem configured to remove methane from an OCM gas exiting the OCM unit. In some embodiments, the demethanation subsystem comprises a pressure-swing adsorption unit. In some embodiments, the system further comprises a methanation unit, which is configured to convert $CO_2$ to methane.

Another aspect of the present disclosure provides a method for producing propylene, comprising: (a) injecting a stream containing methane and a stream containing an oxidizing agent into an oxidative coupling of methane (OCM) unit to generate an OCM effluent stream containing ethylene, propylene, and propane; (b) fractionating the OCM effluent stream using one or more separation units to generate (i) a first stream comprising ethylene and (ii) a second stream comprising propylene and propane; (c) injecting at least a portion of the second stream into an additional separation unit to generate a propylene stream and a propane stream; and (d) injecting at least a portion of the propane stream into a propane dehydrogenation (PDH) unit to generate a PDH effluent containing propylene and hydrogen.

In some embodiments, the method further comprises injecting at least a portion of the PDH effluent into one or more additional separation units to generate a first effluent stream comprising hydrogen and $C_1$-$C_2$ hydrocarbons, and a second effluent stream comprising $C_{3+}$ hydrocarbons. In some embodiments, the oxidizing agent comprises oxygen. In some embodiments, the method further comprises injecting at least a portion of the first effluent stream into the one or more additional separation units to generate a hydrogen stream and an OCM feed stream. In some embodiments, the OCM feed stream contains hydrogen, methane, and ethane. In some embodiments, at least a portion of the OCM feed stream is injected into an OCM recycle loop. In some embodiments, the OCM recycle loop is comprised of any combination of i) a process gas compressor, ii) a methanation unit, iii) a $CO_2$ removal unit, iv) a demethanation unit, and v) the OCM unit. In some embodiments, the OCM recycle loop is comprised of i)-v). In some embodiments, the method further comprises generating heat using hydrogen from the hydrogen stream. In some embodiments, the method further comprises injecting at least a portion of the ethylene produced in the OCM unit into a dimerization unit to generate a butene-containing stream. In some embodiments, the method further comprises injecting at least a portion of the butene-containing stream into the dimerization unit to generate a propylene-containing stream. In some embodiments, the one or more additional separation units comprise include distillation towers. In some embodiments, the one or more additional separation units comprise a pressure-swing adsorption (PSA) unit.

Another aspect of the present disclosure provides a method for producing methanol (MeOH) and hydrocarbon compounds containing at least two carbon atoms ($C_{2+}$ compounds), comprising: (a) separating the CO and/or $CO_2$ from the product stream to generate a CO and/or $CO_2$ stream; (b) directing the CO and/or $CO_2$ stream to an MeOH reactor to produce MeOH; (c) separating the un-reacted $CH_4$ from the product stream to produce a $CH_4$ stream; and (d) directing at least a portion of the $CH_4$ stream to a steam methane reformer (SMR) that produces hydrogen ($H_2$) and CO and/or $CO_2$, wherein the $CH_4$ stream is directed into the SMR without passing through a pre-reformer.

In some embodiments, the method further comprises directing the MeOH produced in (c) to a methanol to olefins (MTO) process to produce a first olefin stream. In some embodiments, the method further comprises combining the first olefin stream and the $C_{2+}$ compounds to produce a combined olefin stream and enriching olefins from the combined olefin stream. In some embodiments, the method further comprises directing CO and/or $CO_2$ produced in the SMR to the MeOH reactor. In some embodiments, all of the CO and/or $CO_2$ from the product stream and all of the CO and/or $CO_2$ from the SMR is converted to MeOH in the MeOH reactor. In some embodiments, the un-reacted $CH_4$ is provided as fuel to the SMR. In some embodiments, the un-reacted $CH_4$ is provided as feedstock to the SMR, and wherein the SMR converts the un-reacted $CH_4$ into the $H_2$ and the CO and/or $CO_2$ for conversion to MeOH in the MeOH reactor. In some embodiments, at least about 95% of the methane is converted into MeOH or $C_{2+}$ compounds. In some embodiments, the method further comprises providing the $C_{2+}$ compounds to a cracker that cracks or refines the $C_{2+}$ compounds. In some embodiments, at least 80% of the methane consumed by the SMR is from the $CH_4$ stream. In some embodiments, the method further comprises directing a portion of the $CH_4$ stream to a cracker. In some embodiments, at least 80% of the methane consumed by the SMR and the cracker is from the $CH_4$ stream. In some embodiments, the method further comprises directing at least a portion of the $CH_4$ stream to a methane-consuming process. In some embodiments, at least 80% of the methane consumed by the SMR, the cracker and the methane-consuming process is from the $CH_4$ stream. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and an oxidizing agent and (ii) reacts the $CH_4$ and the oxidizing agent to yield a product stream comprising the $C_{2+}$ compounds, carbon monoxide (CO) and/or carbon dioxide ($CO_2$), and un-reacted $CH_4$; an MeOH reactor that (i) receives the CO and/or $CO_2$ separated from the product stream and (ii) reacts the CO and/or $CO_2$ to produce MeOH; and a steam methane reformer (SMR) that (i) receives the un-reacted $CH_4$ separated from the product stream without use of a pre-reformer upstream of the SMR, and (ii) provides hydrogen ($H_2$) and at least one of carbon monoxide (CO) and $CO_2$ to the MeOH reactor to produce MeOH.

In some embodiments, the system further comprises a methanol to olefins (MTO) reactor that converts the MeOH to olefins. In some embodiments, the system further comprises a separations module that enriches olefins from the $C_{2+}$ compounds and the olefins. In some embodiments, the system further comprises a separation unit downstream of the OCM reactor and upstream of the MeOH reactor, wherein the separation unit separates the CO and/or $CO_2$ from the product stream. In some embodiments, the system further comprises a separation unit downstream of the OCM reactor and upstream of the SMR, wherein the separation unit separates the un-reacted $CH_4$ from the product stream. In some embodiments, the SMR uses the un-reacted $CH_4$ as fuel. In some embodiments, the SMR uses the un-reacted $CH_4$ as a feedstock and converts the un-reacted $CH_4$ into the $H_2$ and the at least one of CO and $CO_2$ for conversion to MeOH in the MeOH reactor. In some embodiments, the MeOH reactor converts all of the CO and/or $CO_2$ from the product stream and all of the CO and/or $CO_2$ from the SMR to MeOH. In some embodiments, at least about 95% of the methane is converted into MeOH or $C_{2+}$ compounds. In some embodiments, the system further comprises a cracker that (i) receives the $C_{2+}$ compounds and (ii) cracks or refines the $C_{2+}$ compounds. In some embodiments, the un-reacted $CH_4$ directed to the SMR provides at least 80% of the methane consumed by the SMR. In some embodiments, the system further comprises a cracker that receives at least a portion of the unreacted $CH_4$. In some embodiments, at least 80% of the methane consumed by the SMR and the cracker is from the unreacted $CH_4$. In some embodiments, the system further comprises a methane-consuming module that receives the unreacted $CH_4$. In some embodiments, at least 80% of the methane consumed by the SMR, the cracker and the methane-consuming module is from the unreacted $CH_4$. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a method for producing methanol (MeOH) and hydrocarbon compounds containing at least two carbon atoms ($C_{2+}$ compounds), comprising: (a) directing methane ($CH_4$) and an oxidizing agent into an oxidative coupling of methane (OCM) reactor to produce a product stream comprising the $C_{2+}$ compounds, carbon monoxide (CO) and/or carbon dioxide ($CO_2$), and un-reacted $CH_4$; (b) separating the CO and/or $CO_2$ from the product stream to generate a CO and/or $CO_2$ stream; and (c) directing the CO and/or $CO_2$ stream to an MeOH reactor to produce MeOH, wherein the CO and/or $CO_2$ stream is directed into the MeOH reactor without passing through an autothermal reformer (ATR).

In some embodiments, the method further comprises directing the MeOH produced in (c) to a methanol to olefins (MTO) process to produce a first olefin stream. In some embodiments, the method further comprises combining the first olefin stream and the $C_{2+}$ compounds to produce a combined olefin stream and enriching olefins from the combined olefin stream. In some embodiments, all of the CO and/or $CO_2$ from the product stream is converted to MeOH in the MeOH reactor. In some embodiments, at least about 95% of the methane is converted into MeOH or $C_{2+}$ compounds. In some embodiments, the method further comprises directing the $C_{2+}$ compounds to a cracker that cracks or refines the $C_{2+}$ compounds. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and an oxidizing agent and (ii) reacts the $CH_4$ and the oxidizing agent to yield a product stream comprising the $C_{2+}$ compounds, carbon monoxide (CO) and/or carbon dioxide ($CO_2$), and un-reacted $CH_4$; and an MeOH reactor that (i) receives CO and/or $CO_2$ separated from the product stream without use of a pre-reformer upstream of the MeOH reactor, and (ii) reacts the CO and/or $CO_2$ to produce MeOH.

In some embodiments, the system further comprises a methanol to olefins (MTO) reactor that converts the MeOH to olefins. In some embodiments, the system further comprises a separations module that enriches olefins from the $C_{2+}$ compounds and the olefins. In some embodiments, the MeOH reactor converts all of the CO and/or $CO_2$ from the product stream to MeOH. In some embodiments, the system further comprises a separation unit downstream of the OCM reactor and upstream of the MeOH reactor, wherein the separation unit separates the CO and/or $CO_2$ from the product stream. In some embodiments, at least about 95% of the methane is converted into MeOH or $C_{2+}$ compounds. In some embodiments, the system further comprises a cracker that (i) receives the $C_{2+}$ compounds and (ii) cracks or refines the $C_{2+}$ compounds. In some embodiments, the system further comprises a cracker that receives at least a portion of the unreacted $CH_4$. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a method for producing methanol (MeOH) and hydrocarbon compounds containing at least two carbon atoms ($C_{2+}$ compounds), comprising: (a) directing methane ($CH_4$) and an oxidizing agent into an oxidative coupling of methane (OCM) reactor to produce a product stream comprising the $C_{2+}$ compounds and un-reacted $CH_4$; (b) separating the un-reacted $CH_4$ from the product stream to produce a $CH_4$ stream; (c) directing at least a portion of the $CH_4$ stream to a steam methane reformer (SMR) that produces hydrogen ($H_2$) and CO and/or $CO_2$, wherein the $CH_4$ stream is directed into the SMR without passing through a pre-reformer; and (d) directing the CO and/or $CO_2$ produced in (c) to an MeOH reactor to produce MeOH.

In some embodiments, the method further comprises directing the MeOH produced in (d) to a methanol to olefins (MTO) process to produce a first olefin stream. In some embodiments, the method further comprises combining the first olefin stream and the $C_{2+}$ compounds to produce a combined olefin stream and enriching olefins from the combined olefin stream. In some embodiments, all of the CO and/or $CO_2$ from the SMR is converted to MeOH in the MeOH reactor. In some embodiments, the un-reacted $CH_4$ is provided as fuel to the SMR. In some embodiments, the un-reacted $CH_4$ is provided as feedstock to the SMR, and wherein the SMR converts the un-reacted $CH_4$ into the $H_2$ and the CO and/or $CO_2$ for conversion to MeOH in the MeOH reactor. In some embodiments, at least about 95% of the methane is converted into MeOH or $C_{2+}$ compounds. In some embodiments, the method further comprises providing the $C_{2+}$ compounds to a cracker that cracks or refines the $C_{2+}$ compounds. In some embodiments, at least 80% of the methane consumed by the SMR is from the $CH_4$ stream. In some embodiments, the method further comprises directing a portion of the $CH_4$ stream to a cracker. In some embodiments, at least 80% of the methane consumed by the SMR and the cracker is from the $CH_4$ stream. In some embodiments, the method further comprises directing at least a portion of the $CH_4$ stream to a methane-consuming process. In some embodiments, at least 80% of the methane consumed by the SMR, the cracker and the methane-consuming process is from the $CH_4$ stream. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and an oxidizing agent and (ii) reacts the $CH_4$ and the oxidizing agent to yield a product stream comprising the $C_{2+}$ compounds and un-reacted $CH_4$; a steam methane reformer (SMR) that (i) receives the un-reacted $CH_4$ separated from the product stream without use of a pre-performer upstream of the SMR, and (ii) provides hydrogen ($H_2$) and carbon monoxide (CO) and/or $CO_2$, and an MeOH reactor that (i) receives the CO and/or $CO_2$ and (ii) reacts the CO and/or $CO_2$ to produce MeOH.

In some embodiments, the system further comprises a methanol to olefins (MTO) reactor that converts the MeOH to olefins. In some embodiments, the system further comprises a separations module that enriches olefins from the $C_{2+}$ compounds and the olefins. In some embodiments, the system further comprises a separation unit downstream of the OCM reactor and upstream of the SMR, wherein the separation unit separates the un-reacted $CH_4$ from the product stream. In some embodiments, the SMR uses the un-reacted $CH_4$ as fuel. In some embodiments, the SMR uses the un-reacted $CH_4$ as a feedstock and converts the un-reacted $CH_4$ into the $H_2$ and the CO and/or $CO_2$ for conversion to MeOH in the MeOH reactor. In some embodiments, the MeOH reactor converts all of the CO and/or $CO_2$ from the product stream and all of the CO and/or $CO_2$ from the SMR to MeOH. In some embodiments, at least about 95% of the methane is converted into MeOH or $C_{2+}$ compounds. In some embodiments, the system further comprises a cracker that (i) receives the $C_{2+}$ compounds and (ii) cracks or refines the $C_{2+}$ compounds. In some embodiments, the un-reacted $CH_4$ directed to the SMR provides at least 80% of the methane consumed by the SMR. In some embodiments, the system further comprises a cracker that receives at least a portion of the unreacted $CH_4$. In some embodiments, at least 80% of the methane consumed by the SMR and the cracker is from the unreacted $CH_4$. In some embodiments, the system further comprises a methane-consuming module that receives the unreacted $CH_4$. In some embodiments, at least 80% of the methane consumed by the SMR, the cracker and the methane-consuming module is from the unreacted $CH_4$. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a method for producing ethylene and methanol, the method comprising: (a) injecting a methane feedstream and an oxidizing agent-containing feedstream into an oxidative coupling of methane (OCM) subsystem that generates an OCM effluent stream containing ethylene, $CO_2$ and/or CO, and unconverted methane; (b) injecting the OCM effluent stream into a $CO_2$ separation subsystem that generates a stream containing $CO_2$ and a stream containing methane and ethylene; (c) injecting at least a portion of the stream containing $CO_2$ into a methanol synthesis subsystem; (d) injecting at least a portion of the stream containing methane and ethylene into a purification subsystem that generates a stream containing methane and a stream containing ethylene; and (e) injecting at least a portion of the stream containing methane into a steam methane reformer (SMR) subsystem, wherein the at least the portion of the stream containing methane is injected into the SMR subsystem without passing through a pre-reformer.

In some embodiments, the method further comprises, prior to (e), injecting the at least the portion of the stream containing methane into a hydrogenation subsystem. In some embodiments, the hydrogenation subsystem comprises a hydrogenation reactor. In some embodiments, the hydrogenation reactor hydrogenates acetylene. In some embodiments, the method further comprises injecting an oxygen-containing stream and a methane-containing stream into an autothermal reformer (ATR) that generates a stream containing CO and $H_2$. In some embodiments, the methane-containing stream is an effluent of the SMR subsystem. In some embodiments, the method further comprises injecting an effluent of the SMR subsystem into a heat recovery subsystem. In some embodiments, the method further comprises injecting an effluent of the heat recovery subsystem into a syngas compressor subsystem. In some embodiments, the method further comprises injecting an effluent of the syngas compressor subsystem into the methanol synthesis subsystem. In some embodiments, the method further comprises injecting an effluent of the methanol synthesis subsystem into a product recovery subsystem. In some embodiments, the product recovery subsystem comprises one or more distillation columns. In some embodiments, the method further comprises injecting at least a portion of an effluent of the methanol synthesis subsystem into the SMR subsystem. In some embodiments, the method further comprises injecting the methane feedstream into a desulfurization subsystem prior to (a). In some embodiments, having a methanol production rate that is increased by at least about 10% relative to a method that does not comprise injecting a stream containing methane into an oxidative coupling of methane (OCM) subsystem. In some embodiments, the $CO_2$ that is injected into the methanol synthesis subsystem reacts with $H_2$ to produce methanol. In some embodiments, the method further comprises heating the SMR subsystem using at least a portion of the stream containing methane generated in (d). In some embodiments, the oxidizing agent-containing feedstream comprises oxygen.

Another aspect of the present disclosure provides a method for producing olefins, comprising: (a) directing methane ($CH_4$) and an oxidizing agent into an oxidative coupling of methane (OCM) reactor to produce a product stream comprising the $C_{2+}$ compounds including olefins, carbon monoxide (CO) and/or carbon dioxide ($CO_2$), and un-reacted $CH_4$; (b) enriching the CO and/or $CO_2$ from the product stream to generate an enriched CO and/or $CO_2$ stream; (c) directing the enriched CO and/or $CO_2$ stream to an MeOH reactor to produce MeOH; (d) directing at least some of the MeOH to a methanol to olefins (MTO) reactor to produce a second olefins stream; (e) enriching the un-reacted $CH_4$ from the product stream to produce an enriched $CH_4$ stream; and (f) directing at least a portion of the enriched $CH_4$ stream to a steam methane reformer (SMR) that produces hydrogen ($H_2$) and CO and/or $CO_2$.

In some embodiments, the method further comprises recovering olefins from the product stream and the second olefins stream. In some embodiments, the method further comprises directing CO and/or $CO_2$ produced in the SMR to the MeOH reactor. In some embodiments, all of the CO and/or $CO_2$ from the product stream and all of the CO and/or $CO_2$ from the SMR is converted to MeOH in the MeOH reactor. In some embodiments, the un-reacted $CH_4$ is provided as fuel to the SMR. In some embodiments, the un-reacted $CH_4$ is provided as feedstock to the SMR, and wherein the SMR converts the un-reacted $CH_4$ into the $H_2$ and the at least one of CO and $CO_2$ for conversion to MeOH in the MeOH reactor. In some embodiments, at least about 95% of the methane is converted into MeOH or $C_{2+}$ products. In some embodiments, the method further comprises providing the $C_{2+}$ compounds to a cracker that cracks or refines the $C_{2+}$ compounds. In some embodiments, at least 80% of the methane consumed by the SMR is from the enriched $CH_4$ stream. In some embodiments, the method further comprises directing a portion of the enriched $CH_4$ stream to a cracker. In some embodiments, at least 80% of the methane consumed by the SMR and the cracker is from the enriched $CH_4$ stream. In some embodiments, the method further comprises directing at least a portion of the enriched $CH_4$ stream to a methane-consuming process. In some embodiments, at least 80% of the methane consumed by the SMR, the cracker and the methane-consuming process is from the enriched $CH_4$ stream. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a system for producing olefins, comprising: an oxidative coupling of methane (OCM) reactor that (i) receives methane ($CH_4$) and an oxidizing agent and (ii) reacts the $CH_4$ and the oxidizing agent to yield a product stream comprising the $C_{2+}$ compounds including olefins, carbon monoxide (CO) and/or carbon dioxide ($CO_2$), and un-reacted $CH_4$; an MeOH reactor that (i) receives CO and/or $CO_2$ enriched from the product stream and (ii) reacts the CO and/or $CO_2$ to produce MeOH; a methanol to olefins (MTO) reactor that converts at least some of the MeOH into olefins to produce a second olefins stream; and a steam methane reformer (SMR) that (i) receives un-reacted $CH_4$ enriched from the product stream and (ii) provides hydrogen ($H_2$) and at least one of carbon monoxide (CO) and $CO_2$ to the MeOH reactor to produce MeOH.

In some embodiments, the system further comprises a separations module that enriches olefins from the product stream and the second olefins stream. In some embodiments, the system further comprises a separation unit downstream of the OCM reactor and upstream of the MeOH reactor, wherein the separation unit enriches the CO and/or $CO_2$ from the product stream. In some embodiments, the system further comprises a separation unit downstream of the OCM reactor and upstream of the SMR, wherein the separation unit enriches the un-reacted $CH_4$ from the product stream. In some embodiments, the SMR uses the un-reacted $CH_4$ as fuel. In some embodiments, the SMR uses the un-reacted $CH_4$ as a feedstock and converts the un-reacted $CH_4$ into the $H_2$ and the at least one of CO and $CO_2$ for conversion to MeOH in the MeOH reactor. In some embodiments, the MeOH reactor converts all of the $CO_2$ from the product stream and all of the $CO_2$ from the SMR to MeOH. In some embodiments, at least about 95% of the methane is converted into MeOH or $C_{2+}$ products. In some embodiments, the system further comprises a cracker that (i) receives the $C_{2+}$ compounds and (ii) cracks or refines the $C_{2+}$ compounds. In some embodiments, the un-reacted $CH_4$ directed to the SMR provides at least 80% of the methane consumed by the SMR. In some embodiments, the system further comprises a cracker that receives at least a portion of the unreacted $CH_4$. In some embodiments, at least 80% of the methane consumed by the SMR and the cracker is from the unreacted $CH_4$. In some embodiments, the system further comprises a methane-consuming module that receives the enriched $CH_4$. In some embodiments, at least 80% of the methane consumed by the SMR, the cracker and the methane-consuming module is from the unreacted $CH_4$. In some embodiments, the product stream comprises CO. In some embodiments, the product stream comprises $CO_2$. In some embodiments, the product stream comprises CO and $CO_2$. In some embodiments, the oxidizing agent comprises oxygen.

Another aspect of the present disclosure provides a method for producing propylene, the method comprising: (a) feeding propane into a propane dehydrogenation (PDH) process, which PDH process converts the propane into hydrocarbon compounds with three or more carbon atoms ($C_{3+}$ compounds) including propylene and PDH off-gas, which PDH off-gas comprises hydrocarbon compounds with one carbon atom ($C_1$ compounds), hydrocarbon compounds with two carbon atoms ($C_2$ compounds) and hydrogen ($H_2$); (b) feeding the PDH off-gas into an oxidative coupling of methane (OCM) process, which OCM process converts the $C_1$ compounds into ethylene, wherein the OCM process releases heat; and (c) providing the heat to the PDH process.

In some embodiments, the method further comprises converting the $H_2$ to methane in a methanation reactor in the OCM process. In some embodiments, the method further comprises generating from the $C_{3+}$ compounds a propylene stream comprising the propylene, wherein a concentration of the propylene in the propylene stream is greater than a concentration of the propylene in a stream comprising the $C_{3+}$ compounds. In some embodiments, the method further comprises polymerizing the propylene to produce polypropylene. In some embodiments, the method further comprises copolymerizing the propylene with the ethylene produced from the OCM process to produce poly(ethylene-co-propylene). In some embodiments, the OCM process also produces propylene or butene-1. In some embodiments, the method further comprises producing polypropylene and/or poly(propylene-co-1-butene) using the propylene or the butene-1 from the OCM process and/or the propylene from the PDH process. In some embodiments, the method further comprises diverting at least a portion of the propane from the PDH process to the OCM process. In some embodiments, the PDH process is integrated with the OCM process, and wherein the integration of reduces an amount of natural gas needed to provide heat to the PDH process as compared with an amount of natural gas needed for the PDH process in the absence of the integration. In some embodiments, at least about 85% of carbon atoms input into the PDH and the OCM process is converted to propylene, ethylene or polypropylene.

Another aspect of the present disclosure provides a system, comprising: a cracking reactor that receives a hydrocarbon feedstream comprising feedstream hydrocarbons and, with the aid of a cracking catalyst, facilitates cracking of the feedstream hydrocarbons to produce a cracked stream comprising cracked hydrocarbons, wherein the cracked hydrocarbons have a lower molecular weight than the feedstream hydrocarbons; a separations unit in fluid communication with the cracking reactor, wherein the first separations unit receives the cracked stream and separates the cracked hydrocarbons of the cracked stream into a plurality of streams including a methane-containing stream comprising methane; and an oxidative coupling of methane (OCM) reactor in fluid communication with the separations unit, wherein the OCM reactor receives the methane-containing stream and, with the aid of an OCM catalyst, converts the methane from the methane-containing stream to higher hydrocarbon products to yield an OCM product stream comprising the higher hydrocarbon products.

In some embodiments, the system further comprises one or more additional units between the cracking reactor and the separations unit or between the separations unit and the OCM reactor.

Another aspect of the present disclosure provides a method, comprising: (a) directing a hydrocarbon feedstream comprising feedstream hydrocarbons into a cracking reactor comprising a cracking catalyst that facilitates cracking of the feedstream hydrocarbons, to produce a cracked stream comprising cracked hydrocarbons, wherein the cracked hydrocarbons have a lower molecular weight than the feedstream hydrocarbons; (b) directing the cracked stream into a separations unit that separates the cracked hydrocarbons from the cracked stream into a plurality of streams including a methane-containing stream comprising methane; and (c) directing the methane-containing stream into an oxidative coupling of methane (OCM) reactor comprising an OCM catalyst that facilitates conversion of the methane from the methane-containing stream to higher hydrocarbon products to yield an OCM product stream comprising the higher hydrocarbon products.

In some embodiments, (i) the cracked stream is directed from the cracking reactor to the separations unit through one or more additional units or (ii) the methane-containing stream is directed from the separations unit to the OCM reactor through one or more additional units.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1:
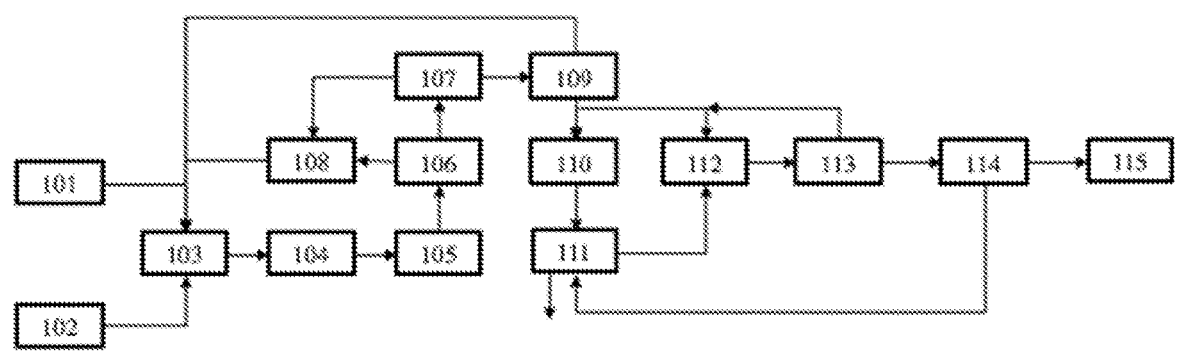
FIG. 1 shows an example process for converting methane into propylene using an oxidative coupling of methane (OCM), dimerization, and metathesis of ethylene and butenes.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terms "$C_{2+}$," and "$C_{2+}$ compound," as used herein, generally refer to a compound comprising two or more carbon atoms, e.g., two carbon atoms ($C_2$), three carbon atoms ($C_3$), etc. $C_{2+}$ compounds include, without limitation, alkanes, alkenes, alkynes and aromatics containing two or more carbon atoms. In some cases, $C_{2+}$ compounds include aldehydes, ketones, esters and carboxylic acids. Examples of $C_{2+}$ compounds include ethane, ethylene, acetylene, propane, propene, butane, butene, etc.

The term "C1-C3 hydrocarbons" refers to the molecular species that include hydrocarbons with one, two, or three carbon atoms. These include methane, ethane, ethylene, acetylene, propane, propylene, and propyne.

The term "non-$C_{2+}$ impurities," as used herein, generally refers to material that does not include $C_{2+}$ compounds. Examples of non-$C_{2+}$ impurities, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "apparent selectivity," as used herein, generally refers to the extent to which an alkane species with a given number of carbons is converted to an olefin with the same number of carbons (e.g. ethane conversion to ethylene, propane conversion to propylene, butane conversion to butane, etc.), and is expressed as a percentage.

The term "residence time," as used herein, generally refers to the average length of time during which a substance is in a given location or condition, such as inside a reactor.

The term "unit," as used herein, generally refers to a unit operation, which is a basic step in a process. Unit operations involve a physical change or chemical transformation, such as separation, crystallization, evaporation, filtration, polymerization, isomerization, transformation, and other reactions. A given process may require one or a plurality of unit operations to obtain the desired product from the starting materials, or feedstocks.

The term "higher hydrocarbon," as used herein, generally refers to a higher molecular weight and/or higher chain hydrocarbon. A higher hydrocarbon can have a higher molecular weight and/or carbon content than starting material(s) in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and can involve an exothermic reaction. In an OCM reaction, methane can be partially oxidized and coupled to form one or more $C_{2+}$ compounds, such as ethylene. In an example, an OCM reaction is $2CH_4+O_2 \rightarrow C_2H_4+2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "item of value," as used herein, generally refers to money, credit, a good or commodity (e.g., hydrocarbon). An item of value can be traded for another item of value.

The term "carbon efficiency," as used herein, generally refers to the ratio of the number of moles of carbon present in all process input streams (in some cases including all hydrocarbon feedstocks, such as, e.g., natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process, such as with the aid of a turbine (e.g., steam turbine). In some cases, power for the operation of the process can be provided by heat liberated by an OCM reaction.

Propylene Generation from Oxidative Coupling of Methane and Metathesis

An aspect of the present disclosure provides methods for integrating an oxidative coupling of methane (OCM) system with a dimerization system and a metathesis system. In this process, methane can be converted into ethylene in the oxidative coupling of methane reactor. The ethylene can be then used as a feedstock for dimerization into butenes, which can then be metathesized into propylene. A fraction of the butenes can later be recycled to the metathesis reactor.

The methane used for any of the processes described herein can come from any suitable source. In some cases, the feedstock for OCM (including methane and optionally ethane) come from the off-gas of a fluidic catalytic cracker (FCC). In some cases, it comes from coal in a coal to olefins (CTO) process. The methane can be gathered from coal beds, or produced from coal or any process utilizing coal.

FIG. 1 shows the integration of an oxidative coupling of methane (OCM) system with a dimerization system and a metathesis system 100. Inputs and outputs into respective units are indicated by arrows. The process 100 shows a source of methane 101 and a source of oxidizing agent 102 that are injected into an oxidative coupling of methane (OCM) reactor 103 in which the feeds are partially converted into ethylene, hydrogen ($H_2$), carbon dioxide ($CO_2$), carbon monoxide (CO), and unconverted methane ($CH_4$). The OCM reactor effluent can be injected into a heat recovery system 104 that cools the effluent stream, and can be then injected into a process gas compressor 105, wherein the gas pressure can be increased. The pressurized process gas can be then injected into a $CO_2$ removal system 106. There are two effluent streams from the $CO_2$ removal system 106, including one $CO_2$ enriched stream and one hydrocarbon enriched stream. The hydrocarbon enriched stream can be injected into a distillation column 107 which can generate a stream comprising methane, a stream comprising $C_2$ hydrocarbons, and a stream comprising $C_{3+}$ hydrocarbons. The $CO_2$ enriched stream from the $CO_2$ removal system 106 and the stream comprising methane from the distillation column 107 can then be injected into a methanation reactor 108. The methanation reactor can convert $CO_2$ into methane. The effluent of the methanation reactor 108 can then be injected into the oxidative coupling of methane (OCM) reactor 103. The stream comprising $C_2$ hydrocarbons that can be an effluent of the distillation column 107 can then be injected into a C2 splitter 109, which can separate ethylene from ethane. The ethane from the C2 splitter 109 can then be injected into the oxidative coupling of methane (OCM) reactor 103. The ethylene from the C2 splitter 109 can then be injected into a dimerization reactor 110 and a metathesis reactor 112. The dimerization reactor converts ethylene into butenes and higher molecular weight hydrocarbons, including 1-butene, 2-butene, isobutene, and $C_{5+}$ hydrocarbons. The effluent of the dimerization reactor 110 can then be injected into a debutenizer 111, which can separate the $C_{5+}$ components from butenes and species lighter than butenes. The butenes can then be injected into the metathesis reactor 112, which reacts ethylene with butenes to generate propylene. The effluent of the metathesis reactor 112 can then be injected into a de-ethanizer 113, which can separate ethylene from $C_{3+}$ components. The ethylene from the de-ethanizer 113 can then be injected into the metathesis reactor 112 or the dimerization reactor 110. The $C_{3+}$ components from the de-ethanizer 113 can then be injected into a de-propanizer 114, which can remove $C_{4+}$ components from $C_3$ components. The $C_{4+}$ components from the de-propanizer 114 can then be injected into the debutanizer 111. The $C_3$ components from the de-propanizer 114 can then be injected into a C3 splitter 115, which can separate propylene from propane.

The oxidizing agent that is injected into the oxidative coupling of methane reactor can be oxygen ($O_2$).

The oxidizing agent that is injected into the oxidative coupling of methane reactor can be hydrogen peroxide ($H_2O_2$).

The operating temperature of the oxidative coupling of methane (OCM) reactor can be at least about 200° C.°, at least about 300° C.°, at least about 400° C., at least about 450° C., at least about 500° C., at least about 550° C., at least about 600° C., at least about 650° C., at least about 700° C., at least about 750° C., at least about 800° C., at least about 850° C., or more.

The operating pressure of the oxidative coupling of methane reactor can be at least about 1 bar(g), at least about 2 bar (g), at least about 3 bar (g), at least about 4 bar (g), at least about 5 bar (g), at least about 6 bar (g), at least about 7 bar (g), at least about 8 bar (g), at least about 9 bar (g), at least about 10 bar (g), at least about 11 bar (g), at least about 12 bar (g), or more.

The concentration of ethylene in the effluent of the oxidative coupling of methane reactor can be at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, or more.

The fraction of ethylene that is generated in the oxidative coupling of methane (OCM) reactor that is injected into the dimerization reactor can be at least about 10%, at least about 20%, at least about 30%, at least about 40%, at least about 50%, at least about 60%, at least about 70%, at least about 80%, at least about 90%, or about 100%.

The fraction of the butenes that is generated in the dimerization reactor can be less than or equal to about 90%, 80%, 70%, 60%, 50%, 40%, 30%, 20%, 10%, 5% (vol %, wt %, or mol %) or less.

Of the butenes generated in the dimerization reactor, 1-butene or 2-butene account for at least about 10%, at least about 20%, at least about 30%, at least about 40%, at least about 50%, at least about 60%, at least about 70%, at least about 80%, at least about 90% (vol %, wt %, or mol %), or more of the total butenes.

The ethylene produced in the oxidative coupling of methane (OCM) reactor can be split between the dimerization reactor and the metathesis reactor, for example, about 90% is injected into the dimerization reactor and 10% is injected into the metathesis reactor, about 80% is injected into the dimerization reactor and 20% is injected into the metathesis reactor, about 70% is injected into the dimerization reactor and 30% is injected into the metathesis reactor, about 60% is injected into the dimerization reactor and 40% is injected into the metathesis reactor, about 50% is injected into the dimerization reactor and 50% is injected into the metathesis reactor, about 40% is injected into the dimerization reactor and 60% is injected into the metathesis reactor, about 30% is injected into the dimerization reactor and 70% is injected into the metathesis reactor, about 20% is injected into the dimerization reactor and 80% is injected into the metathesis reactor, or about 10% is injected into the dimerization reactor and 90% is injected into the metathesis reactor.

Figure 2:
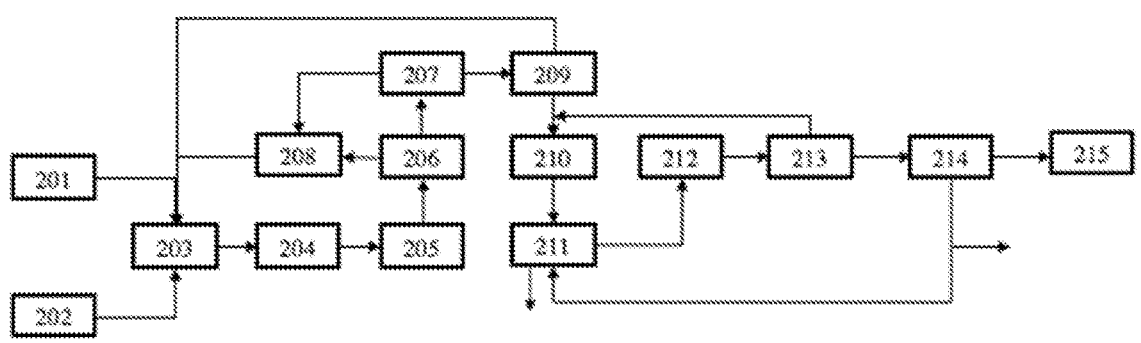
FIG. 2 shows an example process for converting methane into propylene using an oxidative coupling of methane (OCM), dimerization, and metathesis of butenes.

FIG. 2 shows the integration of an oxidative coupling of methane (OCM) system with a dimerization system and a metathesis system 200. Inputs and outputs into respective units are indicated by arrows. The process 200 shows a source of methane 201 and a source of oxidizing agent 202 that are injected into an oxidative coupling of methane (OCM) reactor 203 in which the feeds are partially converted into ethylene. The OCM reactor effluent can be injected into a heat recovery system 204 that cools the effluent stream, and can be then injected into a process gas compressor 205, wherein the gas pressure can be increased. The pressurized process gas can be then injected into a $CO_2$ removal system 206. There are two effluent streams from the $CO_2$ removal system 206, including one $CO_2$ enriched stream and one hydrocarbon enriched stream. The hydrocarbon enriched stream can be injected into a distillation column 207 which can generate a stream comprising methane, a stream comprising $C_2$ hydrocarbons, and a stream comprising $C_{3+}$ hydrocarbons. The $CO_2$ enriched stream from the $CO_2$ removal system 206 and the stream comprising methane from the distillation column 207 can then be injected into a methanation reactor 208. The methanation reactor can convert $CO_2$ into methane. The effluent of the methanation reactor 208 can then be injected into the oxidative coupling of methane (OCM) reactor 203. The stream comprising $C_2$ hydrocarbons that is an effluent of the distillation column 207 can then be injected into a C2 splitter 209, which can separate ethylene from ethane. The ethane from the C2 splitter 209 can then be injected into the oxidative coupling of methane (OCM) reactor 203. The ethylene from the C2 splitter 209 can then be injected into a dimerization reactor 210. The dimerization reactor converts ethylene into butenes and higher molecular weight hydrocarbons, including 1-butene, 2-butene, isobutene, and $C_{5+}$ hydrocarbons. The effluent of the dimerization reactor 210 can then be injected into a debutenizer 211, which can separate the $C_{5+}$ components from butenes and species lighter than butenes. The butenes can then be injected into the metathesis reactor 212, which reacts ethylene with butenes to generate propylene. The effluent of the metathesis reactor 212 can then be injected into a de-ethanizer 213, which can separate ethylene from $C_{3+}$ components. The ethylene from the de-ethanizer 213 can then be injected into the dimerization reactor 210. The $C_{3+}$ components from the de-ethanizer 213 can then be injected into a de-propanizer 214, which can remove $C_{4+}$ components from $C_3$ components. A fraction of the $C_{4+}$ components from the de-propanizer 214 can then be injected into the debutanizer 211, while a fraction is not injected into the debutanizer. The $C_3$ components from the de-propanizer 214 can then be injected into a C3 splitter 215, which can separate propylene from propane.

The ethylene of the C2 splitter can be injected into the dimerization reactor, wherein substantially no ethylene is injected into the metathesis reactor.

The fraction of butenes that are in the effluent of the de-propanizer which are recycled to the metathesis reactor can be less than or equal to about 90%, 80%, 70%, 60%, 50%, 40%, 30%, 20%, 10%, 5% (vol %, wt %, or mol %), or less.

The purity of the ethylene that is injected into the dimerization reactor can be at least about 10 mol %, at least about 20 mol %, at least about 30 mol %, at least about 40 mol %, at least about 50 mol %, at least about 60 mol %, at least about 70 mol %, at least about 80 mol %, at least about 90 mol %, at least about 95 mol %, at least about 99 mol %, at least about 99.5 mol %, at least about 99.9 mol %, or more.

In some embodiments, the conversion of ethylene to butenes in the dimerization reactor can be at least about 10%, at least about 20%, at least about 30%, at least about 40%, at least about 50%, at least about 60%, at least about 70%, at least about 80%, at least about 90%, at least about 95%, at least about 99%, or more.

In some embodiments, the unconverted ethylene that is in the effluent of the dimerization reactor can comprise substantially all of the ethylene that is injected into the metathesis reactor.

Figure 3:
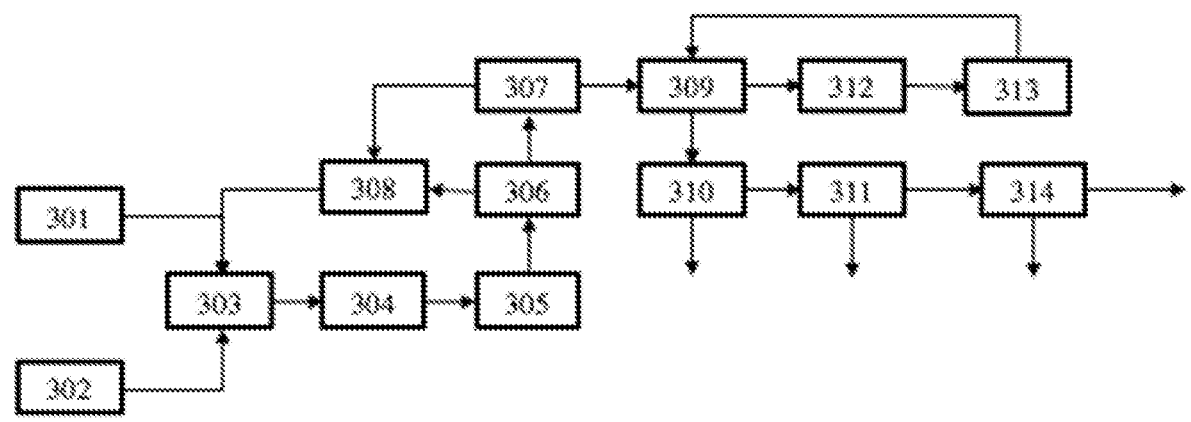
FIG. 3 shows an example process for converting methane into propylene using an oxidative coupling of methane (OCM), vacuum pressure swing adsorption (VPSA), dimerization, and metathesis of butenes.

FIG. 3 shows a system for generating propylene, which integrates an oxidative coupling of methane (OCM) system with a vacuum pressure swing adsorption (VPSA) system, a dimerization system, and a metathesis system 300. The process 300 shows a source of methane 301 and a source of oxidizing agent 302 that are injected into an oxidative coupling of methane (OCM) reactor 303 in which the feeds are partially converted into ethylene. The OCM reactor effluent can be injected into a heat recovery system 304 that cools the effluent stream, and can be then injected into a process gas compressor 305, wherein the gas pressure can be increased. The pressurized process gas can be then injected into a $CO_2$ removal system 306. There are two effluent streams from the $CO_2$ removal system 306, including one $CO_2$ enriched stream and one hydrocarbon enriched stream.

The hydrocarbon enriched stream can be injected into a vacuum pressure swing adsorption unit 307 which can generate a stream comprising methane and a stream comprising $C_{2+}$ hydrocarbons. The stream containing $C_{2+}$ hydrocarbons that can be an effluent of the vacuum pressure swing adsorption (VPSA) can be fed into a de-ethanizer 309 that separates $C_2$ components from $C_{3+}$ components. The $C_{3+}$ components from the de-ethanizer 309 are injected into a stabilizer 310, which separates the $C_{5+}$ components from $C_3$ and $C_4$ components. The $C_3$ and $C_4$ components that are in the effluent of the stabilizer 310 are injected into a de-propanizer 311, which separates the $C_3$ components from the $C_4$ components. The $C_3$ components are then injected into a C3 splitter 314 which separates propylene from proapane. The $C_2$ components from the de-ethanizer 309 are injected into a dimerization reactor 312 that converts ethylene into butenes. The butenes that are generated in the dimerization reactor 312 are then injected into a metathesis reactor 313 that converts butenes into propylene. The effluent of the metathesis reactor can be then injected into the de-ethanizer 309.

In some embodiments, the vacuum pressure swing adsorption system produces an effluent stream that contains less than about 10% methane, less than about 8% methane, less than about 5% methane, less than about 3% methane, less than about 1% methane, less than about 0.5% methane, less than about 0.1% (vol %, wt %, or mol %) methane, or less.

The effluent stream of the C3 splitter may contain at least about 50%, at least about 60%, at least about 70%, at least about 80%, at least about 90%, at least about 95%, or at least about 99% (vol %, wt %, or mol %) of the propylene that is generated in the metathesis reactor.

In some embodiments, oxidative coupling of methane reactor contains a catalyst. OCM catalysts can serve as radicalization initiators. Examples of OCM catalysts can be found in U.S. Patent Publication Serial No. 2012/0041246, U.S. Pat. No. 8,921,256, U.S. Patent Publication No. US 2015/0314267 or U.S. Patent Publication No. 2016/0074844, each of which is incorporated herein by reference in its entirety.

Olefin Generation from Oxidative Coupling of Methane and Cracking

An aspect of the present disclosure provides methods for integrating an oxidative coupling of methane (OCM) process with a thermal cracking process that can be used to generate olefins, including ethylene and ethane. A transformation of a high molecular weight hydrocarbon stream to a stream with a lower average molecular weight can be accomplished by holding the stream at an elevated temperature for a given time. This transformation can occur without the presence of a solid catalyst. A fraction of the stream with a reduced average molecular weight is C1-C3 hydrocarbons. These C1-C3 hydrocarbons separate from higher molecular weight components and used as a feedstock for an oxidative coupling of methane (OCM) process.

Figure 4:
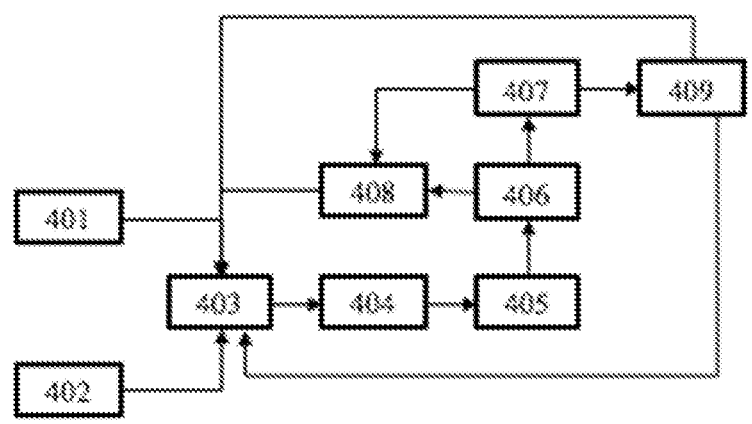
FIG. 4 shows an example process of using an offgas of a cracking unit as a feedstock for an oxidative coupling of methane (OCM) system.

FIG. 4 shows a system for producing ethylene, which incorporates an oxidative coupling of methane (OCM) process with a thermal cracking process 400. The process 400 shows a source of methane 401 and a source of oxidizing agent 402 that are injected into an oxidative coupling of methane (OCM) reactor 403 in which the feeds are partially converted into ethylene. The OCM reactor effluent can be injected into a heat recovery system 404 that cools the effluent stream, and can be then injected into a process gas compressor 405, wherein the gas pressure can be increased. The pressurized process gas can be then injected into a $CO_2$ removal system 406. There are two effluent streams from the $CO_2$ removal system 406, including one $CO_2$ enriched stream and one hydrocarbon enriched stream. The hydrocarbon enriched stream can be injected into a pressure swing adsorption unit 407 which can generate a stream comprising methane and a stream comprising $C_{2+}$ hydrocarbons. The stream containing methane can be injected into a methanation reactor 408. The $CO_2$ enriched stream from the $CO_2$ removal system 406 can be also injected into the methanation reactor 408. The hydrocarbon enriched stream that can be an effluent of the pressure swing adsorption unit 407 can be injected into a cracking subsystem, which includes separations units that can further purify the ethylene from the effluent gas.

Figure 5:
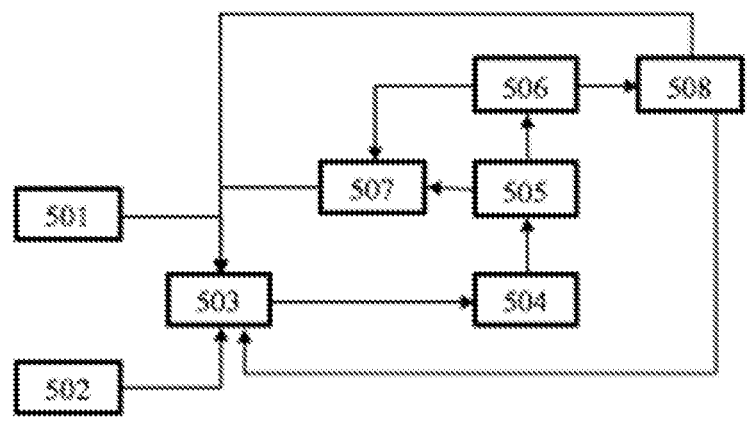
FIG. 5 shows an example process of using an offgas of a cracking unit as a feedstock for an oxidative coupling of methane (OCM) system without the use of a process gas compressor.

FIG. 5 shows a system for producing ethylene, which incorporates an oxidative coupling of methane (OCM) process with a thermal cracking process 500. The process 500 shows a source of methane 501 and a source of oxidizing agent 502 that are injected into an oxidative coupling of methane (OCM) reactor 503 in which the feeds are partially converted into ethylene. The OCM reactor effluent can be injected into a heat recovery system 504, wherein the temperature of the OCM effluent gas can be decreased. The cooled process gas can be then injected into a $CO_2$ removal system 505. There are two effluent streams from the $CO_2$ removal system 505, including one $CO_2$ enriched stream and one hydrocarbon enriched stream. The hydrocarbon enriched stream can be injected into a pressure swing adsorption unit 506 which can generate a stream comprising methane and a stream comprising $C_{2+}$ hydrocarbons. The stream containing methane can be injected into a methanation reactor 507. The $CO_2$ enriched stream from the $CO_2$ removal system 507 can be also injected into the methanation reactor 507. The hydrocarbon enriched stream that can be an effluent of the pressure swing adsorption unit 506 can be injected into a cracking subsystem, which includes separations units that can further purify the ethylene from the effluent gas.

Figure 6:
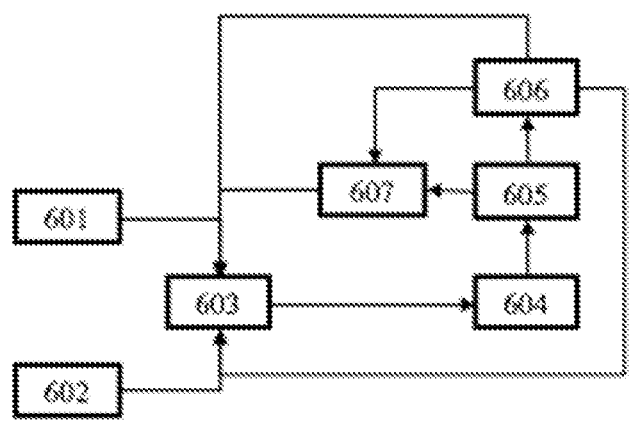
FIG. 6 shows an example process of using an offgas of a cracking unit as a feedstock for an oxidative coupling of methane (OCM) system without the use of a process gas compressor or a pressure swing adsorption (PSA) unit.

FIG. 6 shows a system for producing ethylene, which incorporates an oxidative coupling of methane (OCM) process with a thermal cracking process 600. The process 600 shows a source of methane 601 and a source of oxidizing agent 602 that are injected into an oxidative coupling of methane (OCM) reactor 603 in which the feeds are partially converted into ethylene. The OCM reactor effluent can be injected into a heat recovery system 604, wherein the temperature of the OCM effluent gas can be decreased. The cooled process gas can be then injected into a $CO_2$ removal system 605. There are two effluent streams from the $CO_2$ removal system 605, including one $CO_2$ enriched stream and one hydrocarbon enriched stream. The hydrocarbon enriched stream can be injected into cracking plant 606 that includes further ethylene purification systems. The stream containing methane can be injected into a methanation reactor 607. The $CO_2$ enriched stream from the $CO_2$ removal system 605 can be also injected into the methanation reactor 607.

In some embodiments, the operating temperature of the thermal cracker can be at least about 300° C.°, at least about 400° C.°, at least about 500° C., at least about 600° C., at least about 700° C., at least about 800° C., at least about 900° C., at least about 1000° C., or more.

Olefin Generation from OCM and High-Severity Fluidized Catalytic Cracking

An aspect of the present disclosure provides methods for integrating an oxidative coupling of methane (OCM) process with a high-severity fluidized catalytic cracking system that can be used to generate olefins, including ethylene and ethane. A transformation of a high molecular weight hydrocarbon stream to a stream with a lower average molecular weight can be accomplished by holding the stream at an elevated temperature for a given time. This transformation can occur in the presence of a solid catalyst that flows down the reactor. A high C1-C3 selectivity and a high olefin selectivity can be achieved through the use of high temperatures and low residence times. A fraction of the stream with a reduced average molecular weight is C1-C3 hydrocarbons. These C1-C3 hydrocarbons separate from higher molecular weight components and used as a feedstock for an oxidative coupling of methane (OCM) process.

High severity fluid catalytic cracking (FCC) can utilize traditional FCC technology under severe conditions (higher catalyst-to-oil ratios, higher steam injection rates, higher temperatures, etc.) in order to maximize the amount of propene and other light products. A high severity FCC unit can be fed with gas oils (paraffins) and residues, and can produce about 20-25 m % propene on feedstock together with greater volumes of motor gasoline and distillate byproducts.

Figure 7:
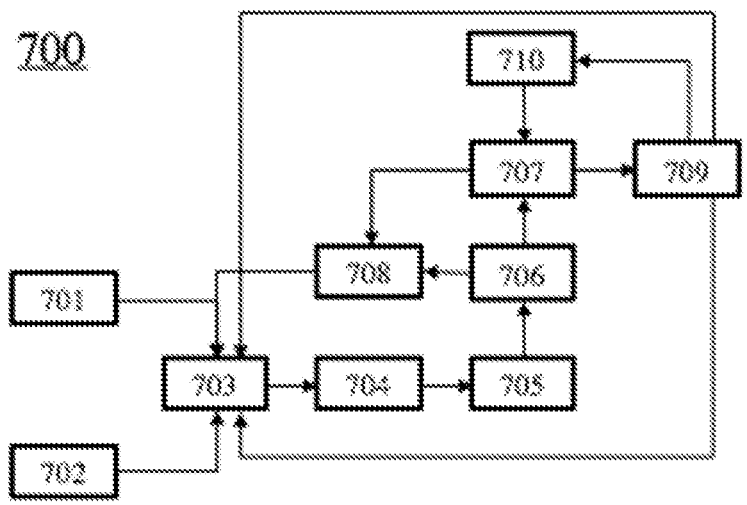
FIG. 7 shows an example system for using an offgas of a high severity fluidized catalytic cracker (HS-FCC) subsystem in tandem with an oxidative coupling of methane (OCM) subsystem.

FIG. 7 shows a system for producing ethylene, which incorporates an oxidative coupling of methane (OCM) process with a high-severity fluidized catalytic cracking system 700. The process 700 shows a source of methane 701 and a source of oxidizing agent 702 that are injected into an oxidative coupling of methane (OCM) reactor 703 in which the feeds are partially converted into ethylene. The OCM reactor effluent can be injected into a heat recovery system 704 that cools the effluent stream, and can be then injected into a process gas compressor 705, wherein the gas pressure can be increased. The pressurized process gas can be then injected into a $CO_2$ removal system 706. There are two effluent streams from the $CO_2$ removal system 706, including one $CO_2$ enriched stream and one hydrocarbon enriched stream. The hydrocarbon enriched stream can be injected into a demethanizer unit 707 which can generate a stream comprising methane and a stream comprising $C_{2+}$ hydrocarbons. The stream containing methane can be injected into a methanation reactor 708. The $CO_2$ enriched stream from the $CO_2$ removal system 706 can be also injected into the methanation reactor 708. The hydrocarbon enriched stream that can be an effluent of the demethanizer unit 707 can be injected into a high-severity fluidized catalytic cracking (HS-FCC) subsystem 709, which includes separations units that can further purify the ethylene from the effluent gas. The high-severity fluidized catalytic cracking (HS-FCC) subsystem has effluent streams that are injected into the OCM reactor 703. These effluent streams include a stream comprising propane, a stream comprising ethane, and a stream comprising methane. The stream comprising methane can be injected into a desulfurization unit 710 that removes sulfur from the methane stream. The desulfurized methane can be then injected into the demethanizer 707.

Figure 8:
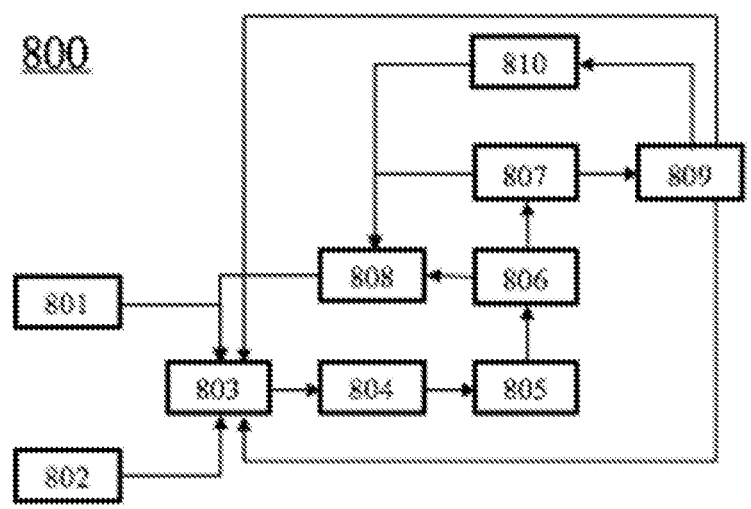
FIG. 8 shows an example system for using an offgas of a high severity fluidized catalytic cracker (HS-FCC) subsystem in tandem with an oxidative coupling of methane (OCM) subsystem which uses a pressure swing adsorption (PSA) unit to purify ethylene.

FIG. 8 shows a system for producing ethylene, which incorporates an oxidative coupling of methane (OCM) process with a high-severity fluidized catalytic cracking system 800. The. The process 800 shows a source of methane 801 and a source of oxidizing agent 802 that are injected into an oxidative coupling of methane (OCM) reactor 803 in which the feeds are partially converted into ethylene. The OCM reactor effluent can be injected into a heat recovery system 804 that cools the effluent stream, and can be then injected into a process gas compressor 805, wherein the gas pressure can be increased. The pressurized process gas can be then injected into a $CO_2$ removal system 806. There are two effluent streams from the $CO_2$ removal system 806, including one $CO_2$ enriched stream and one hydrocarbon enriched stream. The hydrocarbon enriched stream can be injected into a pressure swing adsorption (PSA) unit 807 which can generate a stream comprising methane and a stream comprising $C_{2+}$ hydrocarbons. The stream containing methane can be injected into a methanation reactor 808. The $CO_2$ enriched stream from the $CO_2$ removal system 806 can be also injected into the methanation reactor 808. The hydrocarbon enriched stream that can be an effluent of the PSA unit 807 can be injected into a high-severity fluidized catalytic cracking (HS-FCC) subsystem 809, which includes separations units that can further purify the ethylene from the effluent gas. The high-severity fluidized catalytic cracking (HS-FCC) subsystem has effluent streams that are injected into the OCM reactor 803. These effluent streams include a stream comprising propane, a stream comprising ethane, and a stream comprising methane. The stream comprising methane can be injected into a desulfurization unit 810 that removes sulfur from the methane stream. The desulfurized methane can be then injected into the demethanizer 807.

The methane effluent from the HS-FCC unit may contain hydrogen sulfide ($H_2S$) or hydrogen disulfide ($H_2S_2$). The $H_2S$ and/or $H_2S_2$ may be at a concentration of at least about 0.1 wt. %, at least about 0.5 wt. %, at least about 1 wt. %, at least about 2 wt. %, at least about 3 wt. %, at least about 4 wt. %, at least about 5 wt. %, at least about 7 wt. %, at least about 10 wt. %, at least about 12 wt. % or more.

In some embodiments, the high-severity fluidized catalytic cracker (HS-FCC) operates at a temperature of at least about 400° C., at least about 450° C., at least about 500° C., at least about 550° C., at least about 600° C., at least about 650° C., at least about 700° C., at least about 750° C., at least about 800° C., at least about 850° C., at least about 900° C., or more.

The high-severity catalytic cracker (HS-FCC) may contain an HS-FCC catalyst. The HS-FCC catalyst may comprise a zeolite. The HS-FCC zeolite catalyst may comprise a ZSM-5 zeolite catalyst. The HS-FCC zeolite catalyst may comprise a high USY zeolite.

In some cases, the HS-FCC contains a catalyst that aids in the decrease of molecular weight of a hydrocarbon feedstock. This cracking reaction can take place in the gas phase, in some cases homogenously.

The high-severity fluidized catalytic cracker (HS-FCC) may operate with a residence time of less than about 10 seconds (s), less than about 5 seconds (s), less than about 4 seconds (s), less than about 3 seconds (s), less than about 2 seconds (s), less than about 1 second (s), less than about 0.5 seconds (s), less than about 0.2 seconds (s), less than about 0.1 seconds (s), or less. In some cases, the residence time is a period of time that passes between the feed stream entering the vessel and the cracked hydrocarbon stream exiting the vessel.

In some cases, the HS-FCC unit has a down-comer tube in which reactant and catalyst flows, which may be followed by recovery of the catalyst. In some cases, the catalyst is not fluidized.

Integrations of Oxidative Coupling of Methane with a Propane Dehydrogenation

In some cases, an OCM process is integrated with a propane dehydrogenation (PDH) process. The PDH process can convert propane into propene and by-product hydrogen. The propene from propane yield can be about 85 mass %. Reaction by-products (mainly hydrogen) can be used as fuel for the PDH reaction. As a result, propene may tend to be the only product, unless local demand exists for hydrogen. This route can be used in various regions, such as the Middle East, where there may be an abundance of propane from oil/gas operations. In this region, the propane output may be expected to be capable of supplying not only domestic needs, but also the demand from other regions (such as China), where many PDH projects may be scheduled to go on stream. The PDH process may be accomplished through different commercial technologies. Differences between these technologies may include catalysts employed, design of the reactor and strategies to achieve higher conversion rates.

The integration of the PDH process with an OCM process as described herein can increase the capacity of a PDH process by 40-100 kta in some cases. In some instances, all carbon contained in PDH off-gas can be converted to olefins via OCM and methanation, leading to nearly 100% propane utilization. In some cases, integrating an OCM process with the PDH process can lead to a stable plant capacity over PDH catalyst lifecycle because an increase in PDH off-gas can result in an increased capacity to OCM. The OCM unit can be designed to generate ethylene and butane-1 as co-products to be used as co-monomers in a polypropylene unit, which can enable production of all grades of polypropylene. In some cases, exothermicity of OCM can be used to produce steam and reduce overall firing in the PDH heaters, leading to overall higher carbon utilization in the process.

Figure 9A:
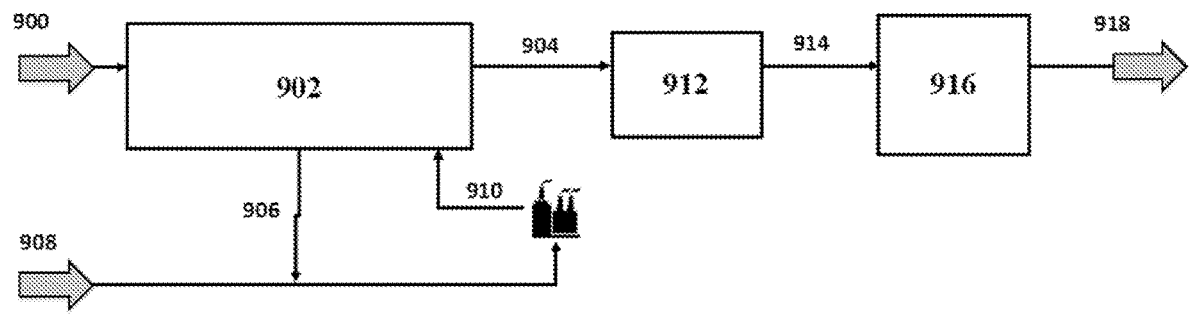
FIG. 9A shows an example of a propane dehydrogenation process.

Turning attention to FIG. 9A, shown here is an example PDH plant with polypropylene (PP) production. Propane 900 can be fed into a PDH unit 902, which can produce a $C_{3+}$ fraction 904 and off-gas 906. The off-gas can include $C_1$ molecules such as methane, carbon dioxide and carbon monoxide, as well as $C_2$ molecules such as ethane and ethylene, and hydrogen ($H_2$). The off-gas can be supplemented with natural gas 908 and burned to produce heat and steam 910 for the PDH unit. The $C_{3+}$ product can be fractionated 912 to produce propylene 914. The propylene can be polymerized in a polypropylene plant 916 to produce polypropylene 918. One limitation of a PDH plant may be that performance decays over the lifetime of the catalyst, leading to a drop in plant capacity before the catalyst can be replaced. About 90% of the propane may be utilized when natural gas is available as a fuel, but may be substantially less when the only fuel is PDH off-gas. Furthermore, without an exogenous supply of ethylene, the only polymer that can be made is homo-polypropylene, which is the lowest grade of polypropylene. These limitations can be alleviated by integrating PDH with an OCM process.

Figure 9B:
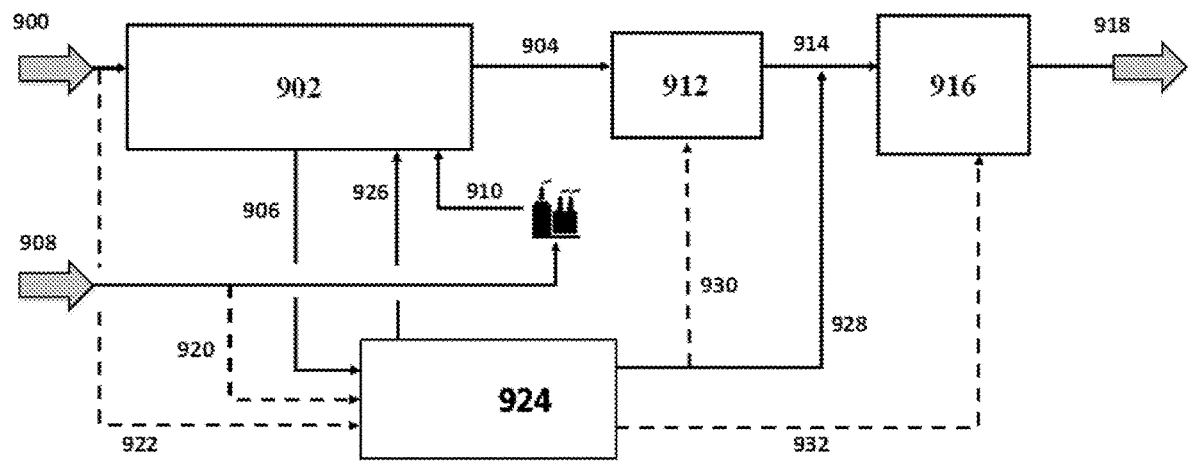
FIG. 9B shows an example of a propane dehydrogenation process integrated with an OCM process.

For example, FIG. 9B shows an example of OCM integrated with PDH. Dashed lines show optional streams. Some natural gas 920 and/or some propane 922 can be diverted into an OCM process 924. The PDH off-gas 906 can also be fed into OCM. The OCM process may be exothermic, and can produce steam 926. The OCM process can produce $C_{3+}$ products that can be added to the propylene product 928 or further refined 930 to propylene if needed. The OCM process can also produce ethylene and/or butene-1, which can be used as a co-monomer 932 in the production of higher grade polypropylene products.

Figure 9C:
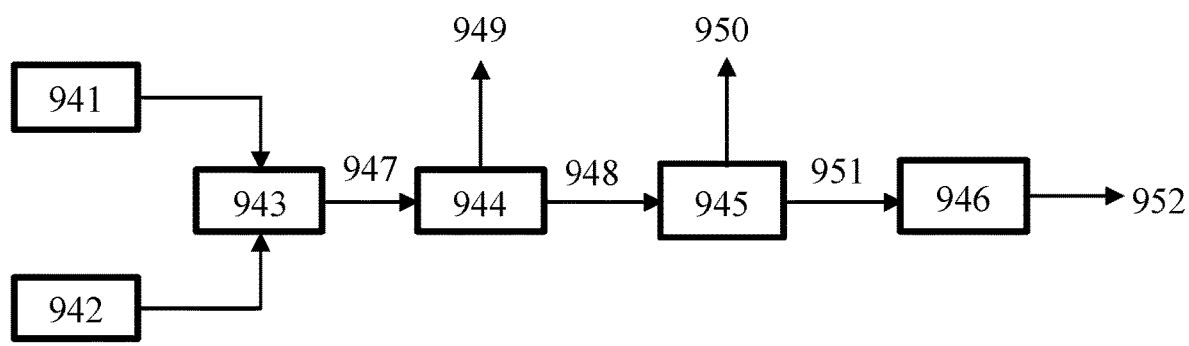
FIG. 9C shows an example system for producing propylene through dehydrogenation of propane that is generated in an oxidative coupling of methane (OCM) process.

FIG. 9C shows an example system for producing propylene through dehydrogenation of propane that is generated in an oxidative coupling of methane process 940. A source containing methane 941 and a source containing oxygen 942 can be injected into an oxidative coupling of methane subsystem 943. The source containing methane can be from the off-gas of a fluidized catalytic cracker. The source containing oxygen can come from an air separation subunit. In some embodiments, the source containing oxygen is the same as the source of methane. Additionally, the source of methane can contain other hydrocarbons, e.g. ethane and propane. The oxidative coupling of methane subsystem can convert methane and oxygen into ethylene. The oxidative coupling of methane subsystem may also generate propylene. The oxidative coupling of methane subsystem may comprise a single reactor or multiple reactors. The oxidative coupling of methane subsystem may comprise one or more post-bed cracking units. The effluent of the OCM subsystem 947 can be injected into a separations subsystem 944 which can generate at least one stream comprising ethylene 949 and at least one stream comprising propylene and propane 948. The separations subsystem can include one or more distillation columns, one or more adsorption subsystems, or combinations thereof. In some embodiments, an adsorption subsystem comprising a metal-organic framework material is used. In some embodiments, an adsorption subsystem comprising a zeolite material is used. The separation subsystem 944 can also comprise one or more units for separating $CO_2$ gas. The stream comprising propylene and propane 948 can then be injected into a separations subsystem 945 which can separate propylene from propane to generate a stream comprising propylene 950 and a stream comprising propane 951. The separations subsystem 945 can include one or more distillation towers, one or more adsorption units, one or more membrane units, or combinations thereof. The stream comprising propane 951 is injected into a propane dehydrogenation (PDH) unit 946 that converts propane into propylene and $H_2$.

Figure 10:
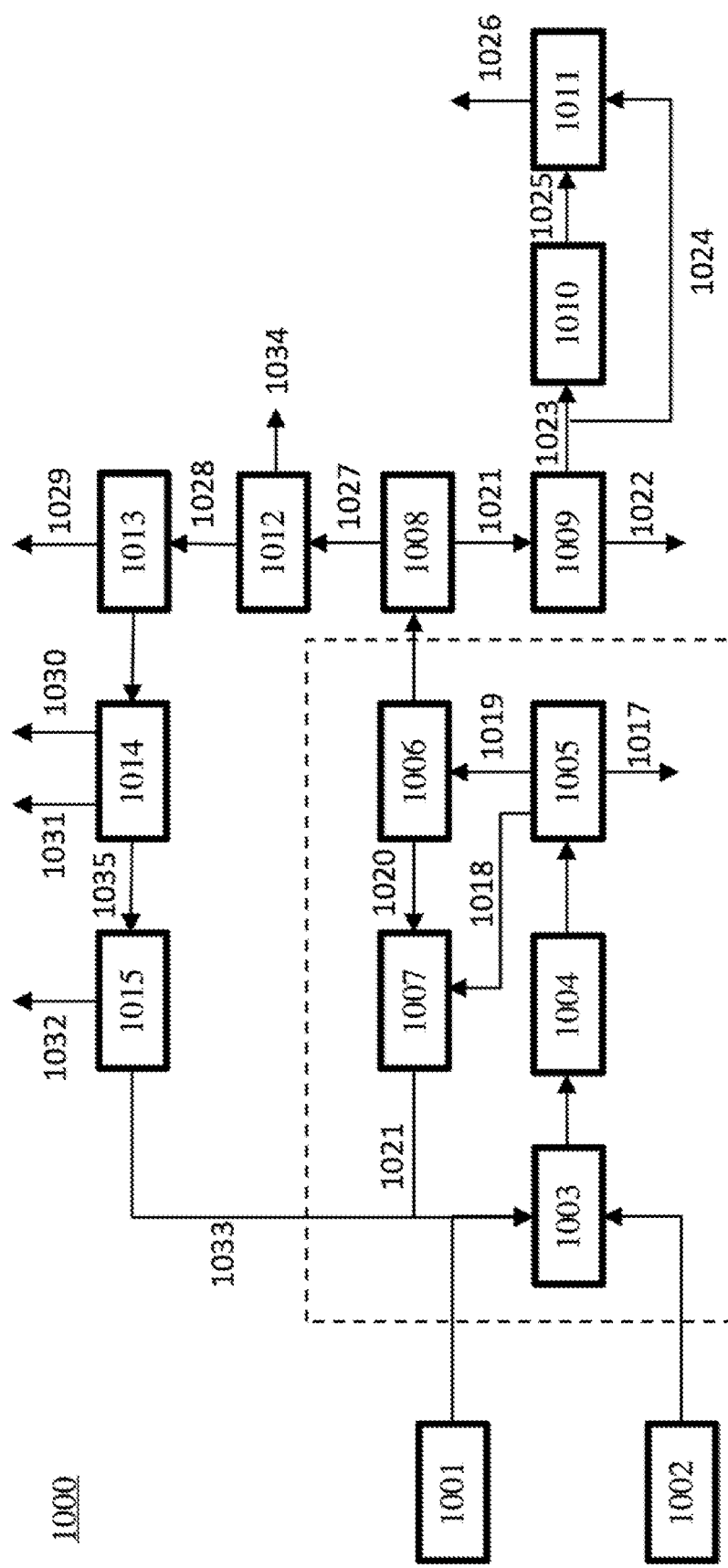
FIG. 10 shows an example system for producing propylene through an integration of an oxidative coupling of methane subsystem, dimerization and metathesis subsystem, and a propane dehydrogenation subsystem.

FIG. 10 shows an example system for producing propylene through the integration of an oxidative coupling of methane subsystem, dimerization and metathesis subsystem, and a propane dehydrogenation subsystem 1000. A source containing methane 1001 and a source containing oxygen 1002 are injected into an oxygen coupling of methane (OCM) subsystem 1003. The source containing methane may be from a recycle loop within the example system 1000. The source containing oxygen may be from an air separation subsystem. The air separation system may include one or more distillation columns, one or more adsorption subsystems, one or more membrane subsystems, or combinations thereof. The source containing methane may come from a fluidized catalytic cracker (FCC) system. The source containing methane may come from an offgas stream within a refinery. The source containing methane may come from natural gas. The source containing methane may also contain heavier hydrocarbons, e.g. ethane, ethylene, propane, propylene, and may also include additional components, e.g. water, $N_2$, $CO_2$, or CO. The source containing methane may be the same as the source containing oxygen. The source containing oxygen and the source containing methane may be mixed within a mixing apparatus separate from or within the OCM subsystem. The OCM subsystem may include an OCM catalyst. The OCM subsystem may include a post bed cracking (PBC) unit.

The effluent of the OCM subsystem is injected into process gas compressor (PGC) subsystem 1004. The PGC subsystem can increase the pressure of the OCM effluent gas to generate a pressurized OCM effluent gas. The PGC subsystem can pressurize the gas to greater than 1 bar, greater than 2 bar, greater than 3 bar, greater than 4 bar, greater than 5 bar, greater than 6 bar, greater than 7 bar, greater than 10 bar, or greater than 15 bar. The pressurized OCM effluent gas can be injected into a $CO_2$ separation subsystem 1005. The $CO_2$ separation subsystem can comprise one or more absorber units, one or more desorber units, one or more adsorption units, one or more membrane units, or combinations thereof. The $CO_2$ separation subsystem can produce a stream containing $CO_2$ 1017, a stream containing $CO_2$ for recycle 1018, and a stream containing methane 1019. The stream containing methane may contain less than 1% $CO_2$, less than 0.5% $CO_2$, less than 0.1% $CO_2$, or less than 0.05% $CO_2$. The stream containing methane is injected into a demethanizer subsystem 1006. The demethanizer subsystem may include one or more distillation columns, one or more adsorption units, one or more membrane units, or combinations thereof. The demethanizer subsystem generates a stream containing methane 1020 and a stream containing $C_{2+}$ hydrocarbons. The stream containing methane may contain additional gases, e.g. CO, $CO_2$, $H_2$, $N_2$, Ar, or $C_2H_2$. The stream containing methane can optionally be injected into a hydrogenation unit that converts $C_2H_2$ into $C_2H_4$. The stream containing methane 1020 and the stream containing $CO_2$ for recycle 1018 are injected into a methanation subsystem 1007. The methanation subsystem can contain a methanation catalyst. The methanation subsystem can convert $H_2$ and $CO_2$ into $CH_4$. The effluent of the methanation subsystem 1021 can be the same as the source of methane 1001. The effluent of the methanation subsystem is injected into the OCM subsystem 1003. The OCM subsystem, PGC subsystem, $CO_2$ removal subsystem, demethanizer subsystem, methanation subsystem, and optional hydrogenation subsystem comprise an OCM recycle loop 1016.

The effluent of the demethanizer subsystem that contains $C_{2+}$ hydrocarbons is injected into a deethanizer subsystem 1008 that generates a stream containing ethylene and ethane 1021, and a stream containing $C_{3+}$ hydrocarbons 1027. The stream containing ethylene and ethane 1021 is injected into a C2 splitter 1009 that generates a stream containing ethane 1022 and a stream containing ethylene 1023. The stream containing ethane 1022 can be mixed with the source containing methane 1001. In some embodiments, the stream containing ethane is injected into the OCM subsystem 1003, the PGC subsystem 1004, or both. In some embodiments, the stream containing ethane is used as a fuel gas in another unit. The stream containing ethylene 1023 is split, with a portion of the stream being injected into a dimerization subsystem 1010 and another portion of the stream being diverted into a bypass loop 1024 and injected into a metathesis subsystem 1011. The dimerization subsystem 1010 can convert ethylene into a stream containing butenes 1025, with some of the butenes being 1-butene. The selectivity for 1-butene may be at least 1%, at least 5%, at least 10%, at least 20%, at least 30%, at least 40%, at least 50%, at least 60%, at least 70%, at least 80%, at least 90%, at least 95%, at least 99%, or at least 100%. The selectivity for 1-butene is the flow rate of 1-butene divided by the flow rate of all C4 hydrocarbons in the effluent of the dimerization subsystem. The dimerization subsystem can contain one or more dimerization reactors. The one or more dimerization reactors can contain a dimerization catalyst. The dimerization catalyst may be a heterogeneous catalyst or a dissolved homogeneous catalyst. Of all the ethylene in the effluent of the C2 splitter, at least 5%, at least 10%, at least 15%, at least 20%, at least 25%, at least 30%, at least 35%, at least 40%, at least 45%, or at least 50% may be injected into the dimerization subsystem. The stream containing butenes 1025 and the ethylene bypass loop 1024 are injected into a metathesis subsystem 1011 that generates a stream containing propylene 1026. The metathesis subsystem may include one or more metathesis reactors. The metathesis reactors may include a metathesis catalyst. The conversion of butenes to propylene in the metathesis subsystem may be at least 10%, at least 20%, at least 30%, at least 40%, at least 50%, at least 60%, at least 70%, at least 80%, at least 90%, at least 95%, or at least 99%.

The stream containing $C_{3+}$ hydrocarbons 1027 is injected into a depropanizer subsystem 1012 that generates a stream containing propylene and propane 1028 and a stream containing $C_{4+}$ hydrocarbons 1034. The depropanizer subsystem can include one or more distillation columns. The stream containing propylene and propane 1028 is injected into a C3 splitter subsystem 1013 that produces a stream containing propylene 1029 and a stream containing propane. The C3 splitter subsystem can include one or more distillation columns, one or more adsorbent units, one or more membrane units, or combinations thereof. The stream containing propane produced from the C3 splitter subsystem is injected into a propane dehydrogenation (PDH) subsystem 1014. The PDH subsystem can dehydrogenate propane to generate a stream containing propylene 1030, a stream containing propane 1031, and a stream containing hydrogen and methane 1035. The stream containing propylene coming from the PDH subsystem 1030 can be combined with the stream containing propylene coming from the metathesis subsystem 1026. In some embodiments, the C3 splitter subsystem is contained within the PDH subsystem. The PDH subsystem can include one or more PDH reactors. The one or more PDH reactors can contain a PDH catalyst. The stream containing hydrogen and methane 1035 can optionally be combined with the offgas of a fluidized catalytic cracking (FCC) system. The stream containing hydrogen and methane 1035 is injected into a separation subsystem 1015 that separates hydrogen from methane. The separation subsystem 1015 can comprise one or more pressure swing adsorption units, one or more membrane units, or combinations thereof. The separation subsystem 1015 generates a stream containing hydrogen 1032 and a stream containing methane 1033. The stream containing hydrogen 1032 can be used as a source of fuel gas, injected into the methanation reactor 1007, or both. The stream containing methane 1033 is injected into the oxidative coupling of methane (OCM) subsystem 1003.

The generation of additional hydrogen in the PDH subsystem increases the carbon efficiency of the OCM recycle loop 1016. The carbon efficiency of the OCM recycle loop may be greater than 10%, greater than 20%, greater than 30%, greater than 40%, greater than about 50%, greater than about 60%, greater than about 70%, greater than about 75%, greater than about 80%, greater than about 85%, greater than about 90%, greater than about 95%, or greater than about 99%.

Integration of OCM Processes with Methanol Processes

There exists an infrastructure for chemical production throughout the world. This infrastructure is deployed on virtually every continent, addresses wide ranging industries, and employs a wide variety of different implementations of similar or widely differing technologies.

The present disclosure provides systems and methods for integrating OCM systems and methods with various chemical processes, such as methanol (MeOH) production, chlorine ($Cl_2$) and sodium hydroxide (NaOH) production (e.g., chloralkali process), vinylchloride monomer (VCM) production, ammonia ($NH_3$) production, processes having syngas (e.g., mixtures of hydrogen ($H_2$) and carbon monoxide (CO) in any proportion), or olefin derivative production.

As will be appreciated, the capital costs associated with each of the facility types described above can run from tens of millions to hundreds of millions of dollars each. Additionally, there are inputs and outputs, of these facilities, in terms of both energy and materials, which have additional costs associated with them, both financial and otherwise that may be further optimized in terms of cost and efficiency. Further, because different facilities tend to be optimized for the particularities (e.g., products, processing conditions) of the market in which they exist, they tend to be operated in an inflexible manner, in some cases without the flexibility or option to optimize for their given market. The present inventors have recognized surprising synergies when integrating OCM with the aforementioned chemical processes which can result in improved economics and/or operational flexibility.

In some cases, the OCM processes described herein are integrated with an olefin oligomerization process, such as an ethylene-to-liquids ("ETL") process as described in U.S. Pat. No. 9,598,328, and U.S. Patent Publication No. 2015/0232395, the full disclosures of each of which are incorporated herein by reference in its entirety for all purposes.

In some instances, the OCM process can be sized to fit the needs of an ethylene derivatives plant. Such a synergy can liberate the derivatives producer from being a merchant buyer of ethylene, allowing the producer more ethylene cost and supply certainty. Examples of ethylene derivatives include polyethylene, including low-density polyethylene (LDPE), linear low-density polyethylene (LLDPE), and high-density polyethylene (HDPE). Additional ethylene derivatives include ethylbenzene, styrene, acetic acid, vinylacetate monomer, ethylene dichloride, vinylchloride monomer, ethylene oxide and alpha olefins.

The OCM processes can be integrated with methanol production processes to realize unexpected synergies potentially including, but not limited to (a) additional methanol capacity with minimal or no modification to the methanol plant and (b) additional ethylene capacity with low investment and environmental footprint.

Figure 11:
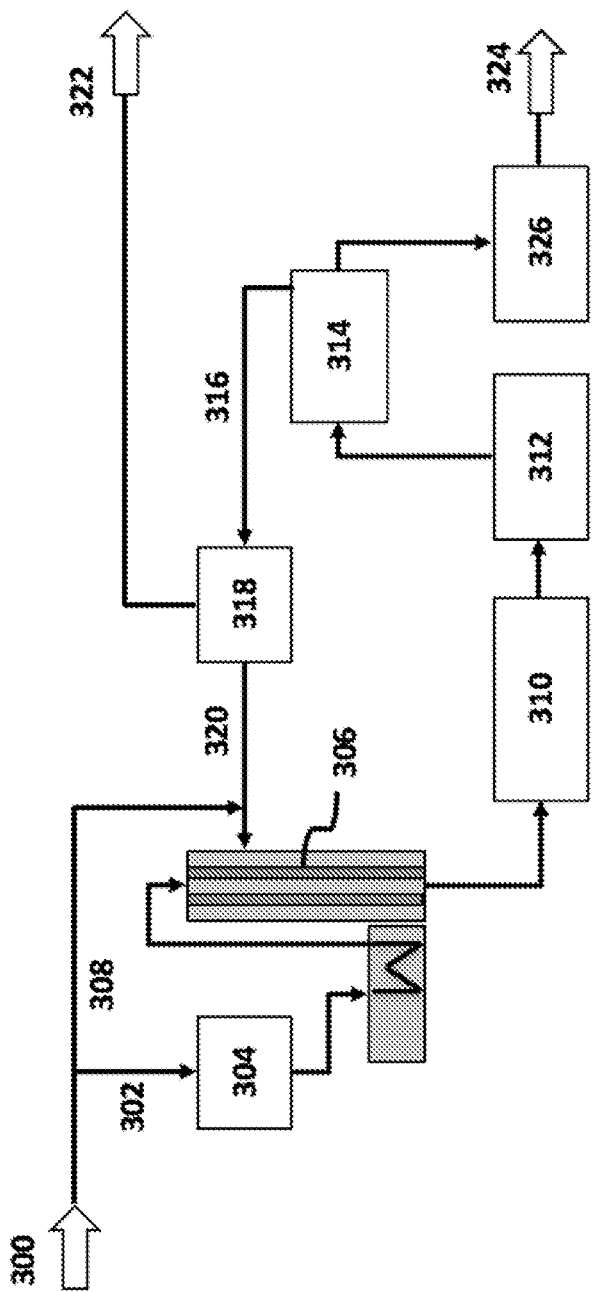
FIG. 11 is a schematic illustration of a methanol production process.

FIG. 11 shows an example of a block flow diagram of a methanol plant (e.g., a traditional methanol process, recognizing that alternate embodiments are allowed and details have been emitted for clarity). As shown, natural gas 300 can be used for feed and fuel for the process. The feed 302 (e.g., natural gas providing the carbon atoms for the methanol product) can have sulfur-containing compounds removed in a de-sulfurization module 304 before being fed into a steam methane reformer (SMR, entire gray shaded unit) 306. The SMR can also accept natural gas as fuel 308 (e.g., natural gas providing energy for the methanol plant), which does not necessarily have to be de-sulfurized. The effluent of the steam methane reformer is syngas, which can have heat recovered in a heat recovery module 310 and compressed in a compression module 312. Compressed syngas can be fed into the synthesis module 314 where conversion to methanol occurs. One suitable methanol synthesis module can have a catalyst that is a mixture of copper, zinc, and alumina, and operates at a pressure between about 50 and about 100 atmospheres and a temperature of about 250° C. The production of syngas produces 3 moles of $H_2$ per mol of $CH_4$, while the stoichiometry of methanol formation from syngas consumes only 2 moles of $H_2$. Thus, excess $H_2$ (and unreacted $CH_4$) can be purged 316 from the synthesis module and separated in a gas separation module 318 (e.g., a pressure swing adsorber). The separation module can produce additional fuel 320 for the SMR and a $H_2$ co-product 322. The methanol product 324 can be enriched (e.g., by a distillation module 326). In some cases, the excess $H_2$ is used as fuel (not shown).

A combined process that integrates OCM with methanol production is shown in FIG. 4, where like numerals represent like elements. The OCM portion of the combined process can accept the de-sulfurized natural gas feedstock 414 and include an OCM reaction module 400, a process gas compression module 402, a $CO_2$ removal module (e.g., process gas cleanup) 404, a drying module 406 and a separations module (e.g., a cryogenic de-methanizer) 408. In some cases, the separation module produces the $C_{2+}$ compounds 410. The $C_{2+}$ compounds can be further refined, and/or sent to a cracker (e.g., to the separation section of a cracker). Note that the OCM process does not require a methanation module. The OCM reaction can produce high-pressure super-heated (HPSH) steam 412 that can be used in the process and/or to produce power using a steam turbine.

Figure 12:
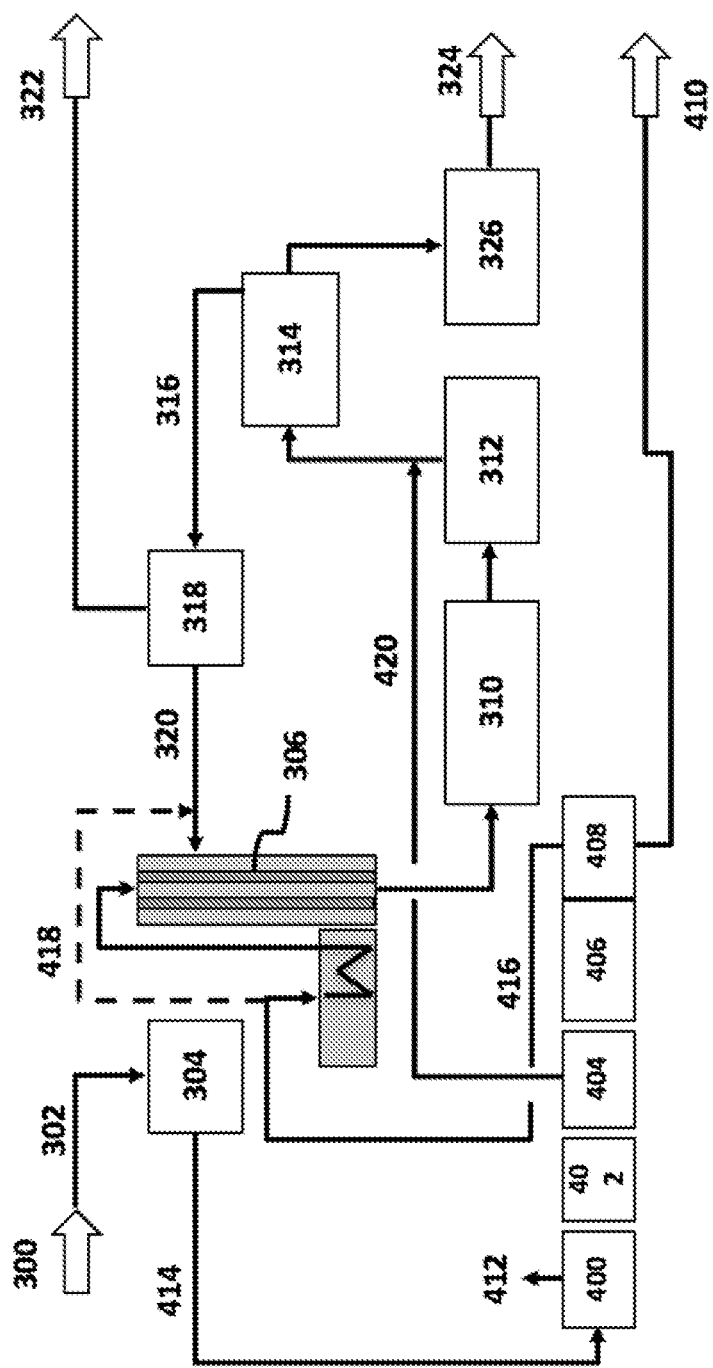
FIG. 12 is a schematic illustration of OCM integrated with a methanol production process.

Continuing with FIG. 12, the OCM portion of the process can produce a stream of methane that was not converted to $C_{2+}$ compounds 416 in the OCM reaction. This stream 416 can have $H_2$ and CO in addition to methane and can be used as the feed to the methanol production process (e.g., at the SMR) and/or as fuel to the process (dashed line) 418. The stream of $CO_2$ 420 from the OCM process can also be used in the methanol synthesis module 314 to produce one mole of methanol and one mole of water from one mole of $CO_2$ and 3 moles of $H_2$. The water co-product can be removed in the distillation module 326.

The combined OCM-methanol process has considerable economic and environmental benefits. In some cases, $CO_2$ from OCM 420 can be used to re-balance the make-up gas to the synthesis module and convert some or all of the excess $H_2$ to methanol (e.g., the flow-rate of stream 322 can be zero or very small in comparison to the flow rate without OCM integration). Furthermore, the reformer 306 capacity can be automatically increased due to the "pre-formed" nature of the OCM demethanizer overhead 416 stream (e.g., already contains some $H_2$ and CO). This can be useful for replacing a mixed feed coil. In some instances, the only cost associated with the production of extra methanol due to OCM integration is the loss in value of the $H_2$ co-product 322 in situations where that stream is actually monetized or monetizable. Such integration schemes can result in improved efficiency of an existing methanol system, for example by using excess $H_2$ by reacting it with $CO_2$ produced from an OCM unit to produce a more valuable methanol product. Depending on the capacity of the OCM process, an integrated OCM-methanol system can be pushed to a low emission, high carbon efficiency process.

When retrofitting an existing methanol plant, the OCM process can be sized to the desired amount of extra methanol production. From the OCM perspective, building an OCM process to be integrated with a methanol plant can require significantly less capital than building a stand-alone OCM process, e.g., due to reducing or eliminating the need for fractionation and methanation equipment. The OCM process can also use the utilities of the existing methanol plants, such as steam. In some cases, the combined process produces zero or a minimal amount of $NO_x$ and $SO_x$ compounds.

Figure 13:
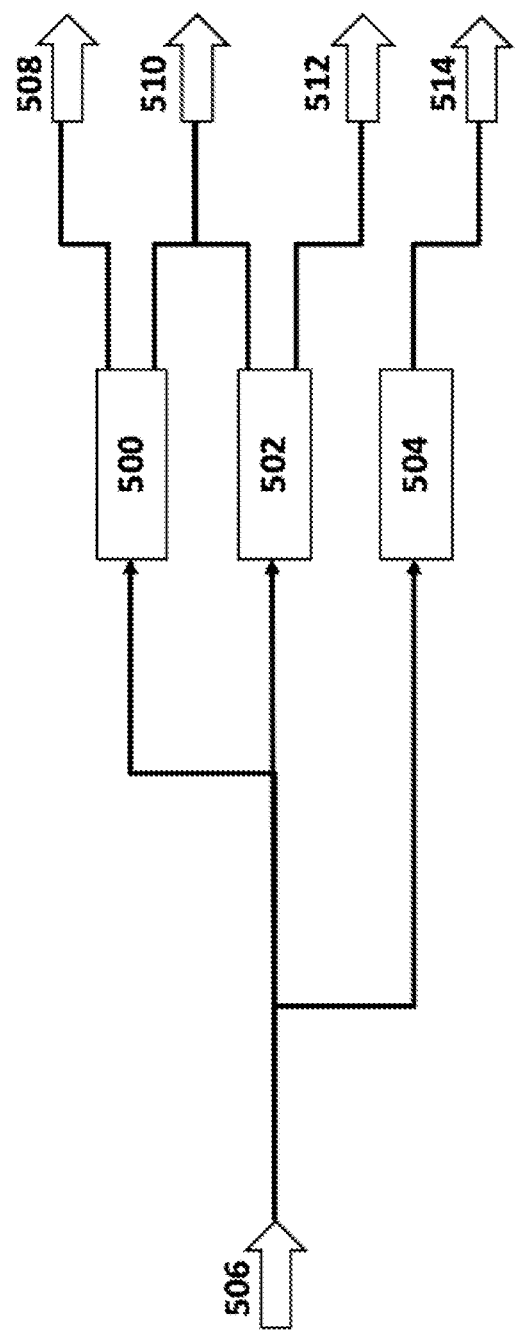
FIG. 13 is a schematic illustration of a petrochemical complex with a methanol production process and a cracker.

The combined OCM-methanol process can be about 100% carbon efficient (e.g., with reference to FIG. 13, all of the carbon atoms input to the process 300 end up in the methanol 324 or the $C_{2+}$ compounds 410). In some cases, the combined process is less than 100% carbon efficient, e.g., greater than or equal to about 99%, greater than or equal to about 98%, greater than or equal to about 97%, greater than or equal to about 96%, greater than or equal to about 95%, greater than or equal to about 93%, greater than or equal to about 90%, greater than or equal to about 85%, greater than or equal to about 80%, or greater than or equal to about 75% carbon efficient.

In some cases, with reference to FIG. 5, methanol plants 500 are located in proximity to crackers 502 and/or other processes 504 that use natural gas (e.g., within 1, 5, 10, 20, 50, 100, 200 miles or more). In some cases, these processes share a piping infrastructure and/or can access a piping infrastructure for transporting natural gas, ethylene, hydrogen and other chemicals. These processes can convert the natural gas 506 into a combination of methanol 508, hydrogen 510, ethylene 512, and other products 514. OCM can be integrated with any combination of these processes (e.g., 500, 502 and 504) in a number of ways as shown in FIG. 6, FIG. 7 and FIG. 8.

Figure 14:
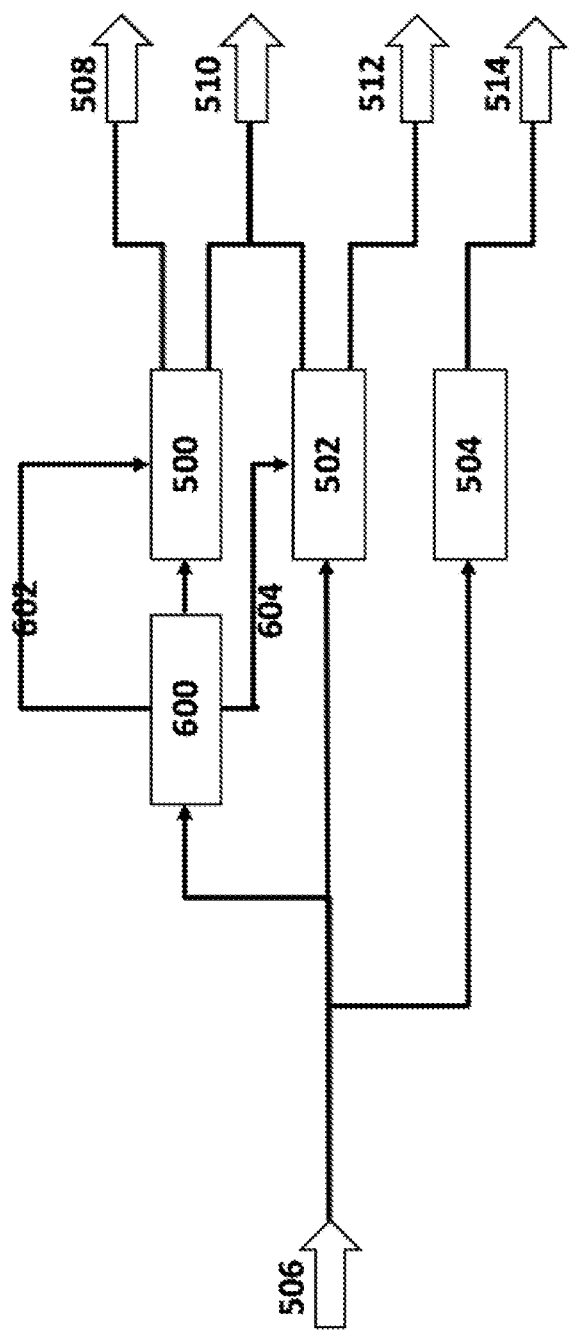
FIG. 14 is a schematic illustration of an integration of OCM with a methanol production process and a cracker.

FIG. 14 shows a "minimum revamp case" where an OCM process 600 accepts natural gas 506 and provides $CO_2$ 602 to a methanol process 500 and crude ethylene 604 to a cracker 502. The ethylene can be refined to a finished product (e.g., polymer grade ethylene) 512 using the fractionation capacity of the cracker. In this case, the OCM process can be sized to accept an amount of natural gas that is substantially equivalent to the methanol plant natural gas input (e.g., about 60 to 70 MMSCFD). This OCM capacity can result in about 25-30 kTa additional ethylene and about 15% to 20% additional methanol produced. In some cases, for the minimum revamp case, the only capital investment is for the OCM unit 600 and in some cases mixed feed coil replacement in the SMR.

Figure 15:
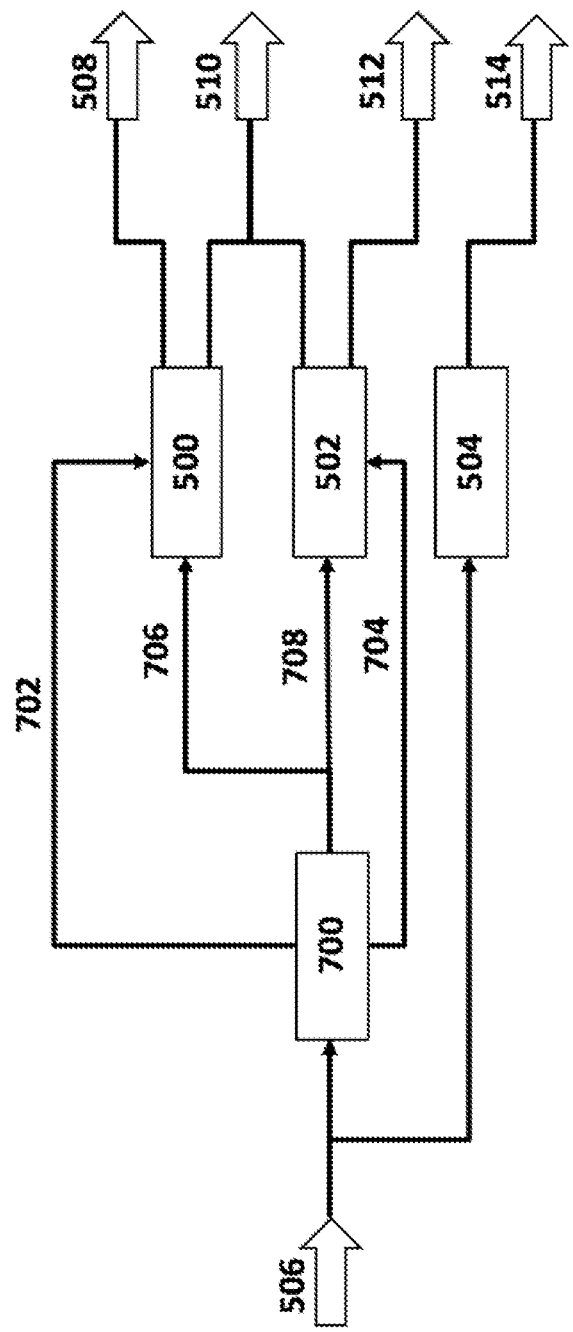
FIG. 15 is a schematic illustration of an integration of OCM with a methanol production process and a cracker.

FIG. 15 shows a "medium revamp case" where an OCM process 700 accepts natural gas 506 and provides $CO_2$ 702 to a methanol process 500 and crude ethylene 704 to a cracker 502. In this case, the OCM process can be sized to accept an amount of natural gas that is substantially equivalent to the methanol plant natural gas input 706 and cracker fuel input 708 (e.g., about 140 to 150 MMSCFD). This OCM capacity can result in about 60-80 kTa additional ethylene and about 30% to 40% additional methanol produced. In some cases, for the medium revamp case, capital investment is needed for the OCM unit 700 and methanol debottlenecking (e.g., reformer, syngas compressor, synthesis module and topping column).

Figure 16:
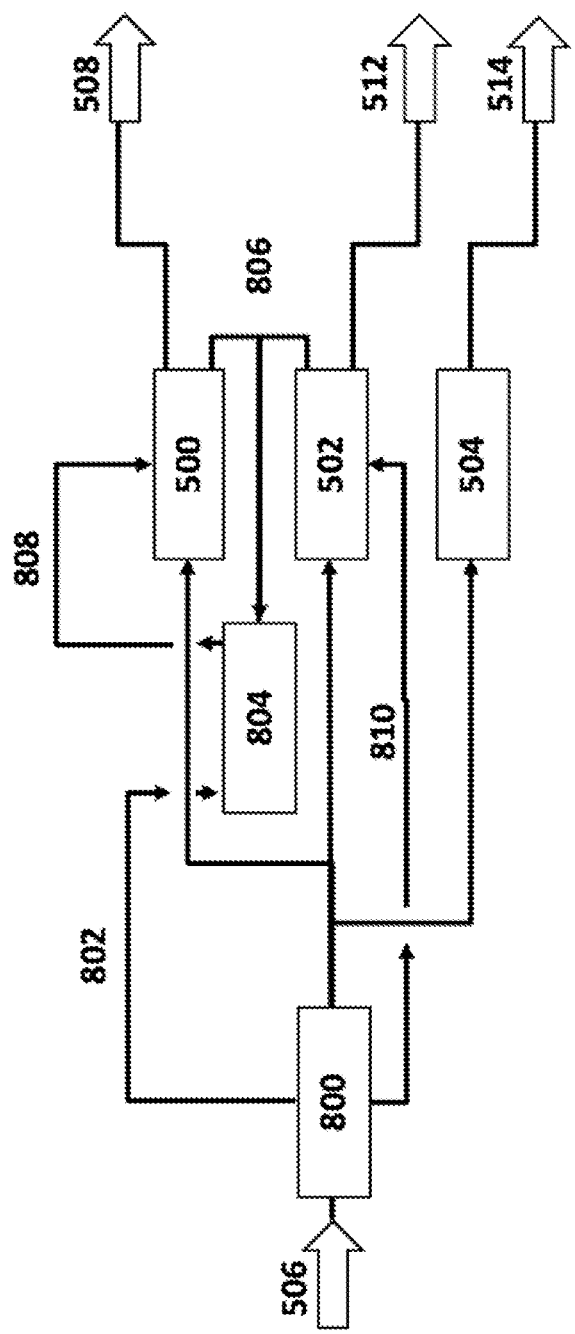
FIG. 16 is a schematic illustration of an integration of OCM with a methanol production process and a cracker.

FIG. 16 shows a "maximum efficiency revamp case" where the size of the OCM process is not constrained. For example, all of the natural gas entering an entire petrochemical complex can be skimmed. An OCM process 800 accepts natural gas 506 and provides $CO_2$ 802 to a new methanol synthesis module 804. In some cases, the new methanol synthesis module 804 accepts $H_2$ 806 from various sources including an existing methanol process 500 and/or a cracker 502. The new methanol synthesis module 804 can provide crude methanol 808 to the existing methanol process for refining to a methanol product 508. As in the other revamp scenarios, crude ethylene 810 can be refined in a cracker 502. In some cases, the OCM results in about 150-200 kTa additional ethylene, the integration results in about 60% to 70% additional methanol produced. In some cases, for the maximum efficiency revamp case, capital investment is needed for the OCM unit, a new methanol synthesis module (fed with the excess $H_2$ across the entire complex and $CO_2$ from OCM) and in some cases debottlenecking of methanol distillation. The various revamp cases are not mutually exclusive and can be designed as successive project phases. In addition, larger capacity plants can be combined with larger methanol production plants.

Figure 17:
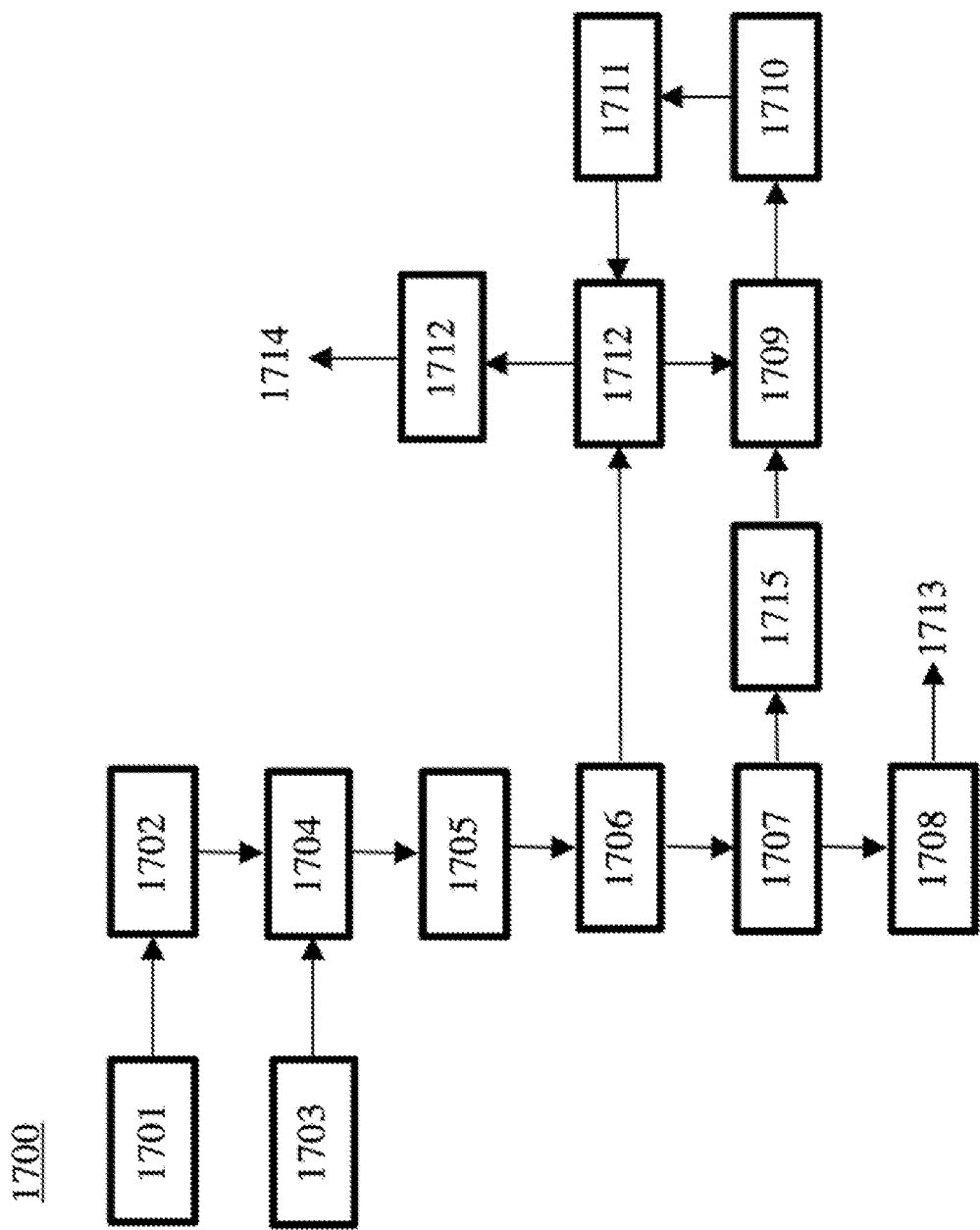
FIG. 17 is a schematic illustration of an integration of OCM with a methanol production process and a synloop.

FIG. 17 shows a schematic illustration of an integration of OCM with a methanol production process and a synloop 1700. A stream containing methane 1701 is injected into a desulfurization subsystem 1702 that removes sulfur from the stream containing methane. The stream containing methane can be natural gas. The desulfurization subsystem can include one or more hydrodesulfurization reactors. The desulfurization subsystem can include one or more adsorbent units. The effluent of the desulfurization subsystem and a stream containing oxygen 1703 is injected into an oxidative coupling of methane (OCM) subsystem 1704. The oxidative coupling of methane subsystem can contain an oxidative coupling of methane (OCM) catalyst. The oxidative coupling of methane subsystem can comprise one or more post-bed cracking (PBC) units. The oxidative coupling of methane (OCM) subsystem can generate an OCM effluent stream containing ethylene, $CO_2$ and/or CO, and unconverted methane. The OCM effluent stream is injected into a process gas compressor (PGC) subsystem 1705 that elevates the pressure of the gas to produce a pressurized oxidative coupling of methane (OCM) effluent. The pressurized OCM effluent is injected into a separation subsystem 1706 that removes $CO_2$ from the pressurized OCM effluent to generate a stream containing $CO_2$ and a stream containing ethylene and methane. The separation subsystem can comprise one or more absorber units, one or more adsorber units, one or more distillation columns, or combinations thereof. The stream containing ethylene and methane is injected into a purification subsystem 1707 that generates a stream containing methane and a stream containing ethylene. The purification subsystem can comprise one or more distillation columns, one or more adsorbent units, one or more membrane units, or combinations thereof. The stream containing ethylene can also include ethane and hydrocarbons with three or more carbon atoms ($C_{3+}$ hydrocarbons). The stream containing ethylene is injected into a separation subsystem 1708 that generates a stream containing ethylene 1713.

The stream containing methane that is the effluent of the purification subsystem 1707 is injected into a hydrogenation subsystem 1715. The hydrogenation subsystem can contain one or more hydrogenation reactors. The one or more hydrogenation reactors can contain a hydrogenation catalyst. The hydrogenation subsystem can hydrogenate acetylene. The effluent of the hydrogenation subsystem contains CO and/or $CO_2$. The effluent of the hydrogenation subsystem is injected into a steam methane reformer (SMR) subsystem 1709, without be injected into a pre-reformer. The pre-reformer may otherwise generate CO and $H_2$ from hydrocarbons before entering the steam methane reformer (SMR) subsystem. The steam methane reformer subsystem can convert water and methane into a syngas stream that comprises CO and $H_2$. The syngas stream is injected into a heat recovery subsystem 1710 that removes heat from the syngas stream. The effluent of the heat recovery subsystem is injected into a syngas compressor subsystem 1711 that increases the pressure of the syngas stream to produce a pressurized syngas stream. The pressurized syngas stream is injected into a methanol synthesis subsystem 1712 that at least partially converts CO and $H_2$ into methanol. The $CO_2$ that is generated in the separation subsystem 1706 is also injected into the methanol synthesis subsystem. The methanol synthesis subsystem can also include one or more water gas shift reactors. The one or more water gas shift reactors can convert $CO_2$ and $H_2$ into CO and water. The methanol synthesis subsystem can produce an offgas. The offgas can be comprised of methane, CO, $CO_2$, $H_2$ or combinations thereof. The offgas is injected into the steam methane reformer subsystem. The offgas can be used as a fuel to heat the steam methane reformer subsystem, or can be used as a feedstock for the steam methane reformer subsystem, or both. The methanol syntheses subsystem can also produce non-methanol impurities. At least a portion of the effluent of the methanol synthesis subsystem is injected into a product recovery subsystem 1712 to produce a methanol stream 1714. The product recovery subsystem can include one or more distillation columns.

The source of oxygen 1703 can also be used in an autothermal reformer (ATR) subsystem that converts methane and oxygen into CO and $H_2$. The ATR subsystem can use the effluent of the steam methane reformer (SMR) subsystem as a source of methane, or can use a separate source of methane, or both.

Integration of OCM Processes with Methanol to Olefins (MTO) Processes

Methanol-to-Olefins/Methanol-to-Propene may convert synthesis gas (syngas) to methanol, and then convert the methanol to ethylene and/or propene. The process may produce water as by-product. Synthesis gas may be produced from the reformation of natural gas or by the steam-induced reformation of petroleum products such as naphtha, or by gasification of coal.

Application of an MTO process may use acidic zeolite catalysts. The conversion of methanol to olefins on acidic zeolites may take place through a complex network of chemical reactions. The distribution of products and thus the "selectivity" may depend on the temperature, among other factors. Selectivity may be a measure of the amount of one product produced relative to others when the possibility to form multiple products exists. Selectivity may depend on temperature through the Arrhenius law for the different rate constants.

In some cases, at lower temperatures methanol reacts to form dimethyl ether (DME). At higher temperatures, the desired products (olefins) may be produced and the selectivity for DME may decrease.

In some cases, the methanol can be converted to olefins using a methanol to olefins (MTO) process. The OCM process can be integrated with an MTO process to realize certain synergies. The carbon efficiency of the combined process can be greater than either of the processes individually. For example, in the combined process, at least about 80%, at least about 85%, at least about 90%, at least about 95%, at least about 98%, at least about 99%, at least about 99.5%, or at least about 99.9% of the feedstock carbon can be converted to final products. In some cases, a single air separations unit (ASU) can be used for both the methanol/MTO and the OCM processes. In some cases, a single separations and/or olefin purification train can be used for both the methanol/MTO and the OCM processes. In some cases, a single utility train can be used for both the methanol/MTO and the OCM processes (i.e., with tight energy integration).

In some embodiments, the combined OCM and methanol/MTO process can share a separations train (e.g., cryogenic distillation). Because of this synergy, the combined process can achieve increased capacity with essentially the same equipment. In MTO, the syngas train represents the most capital intensive area of the process. Combo-reforming can be used to achieve the ideal syngas composition for methanol synthesis. In some cases, combo-reforming is needed to achieve greater than 5,000 metric ton per day (MTD) methanol capacity on a single train. In some instances, olefin conversion technology (OCT), which involves converting $C_{4+}$ into ethylene and propylene, can be used to increase the carbon yield of light olefins.

Figure 18:
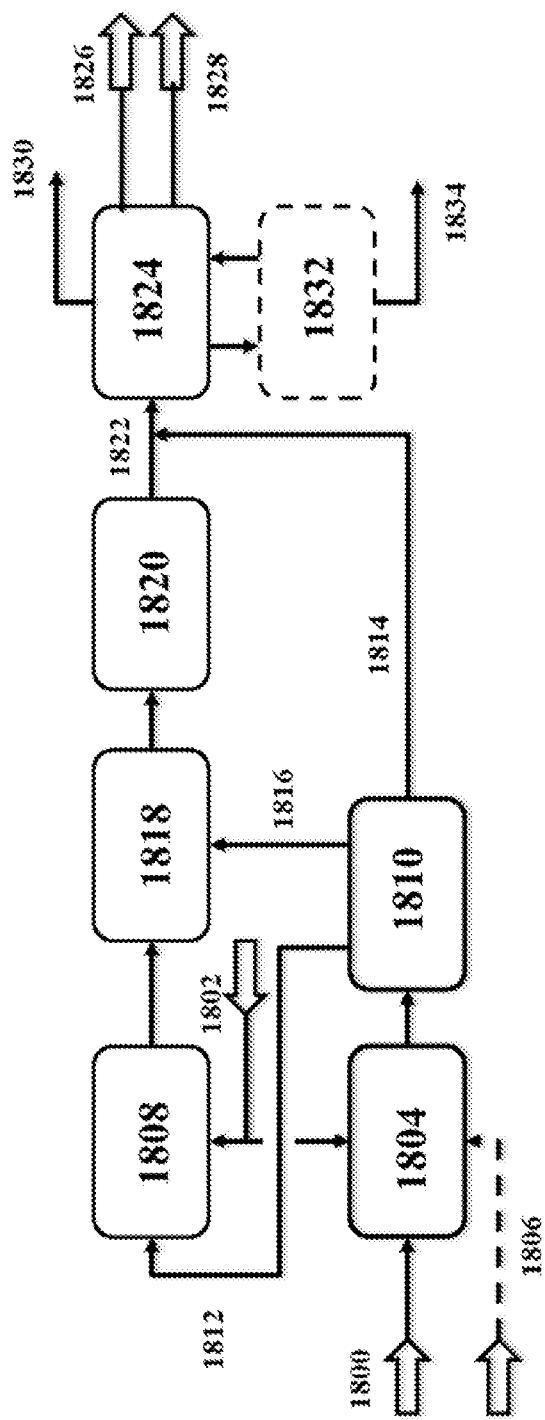
FIG. 18 is a schematic illustration of an integration of OCM with a MTO production process.

Referring to FIG. 18, natural gas 1800 and oxygen 1802 can be fed into an OCM reactor 1804, optionally with additional $C_2$-$C_4$ feed 1806. Some of the oxygen can also be fed into the methanol process, e.g., at the ATR or SMR 1808. A first separation module 1810 can separate light gasses 1812 (having, e.g., $CH_4$, CO and $H_2$) from an ethylene-rich stream 1814. The first separation module does not need to produce purity or enriched ethylene. In some cases, the first separation module includes a PSA. The separations module can also produce a $CO_2$ stream 1816, that can be sent to the MeOH synthesis module 1818. The MeOH can then be fed to a MTO unit 1820 to produce olefins 1822. The olefins from the MTO process 1822 and from the OCM process 1814 can be combined and recovered in an olefin recovery module 1824. The olefin recovery module can produce an ethylene product stream 1826, a propylene product stream 1828, and fuel gas 1830. In some cases, $C_{4+}$ products can be sent to an olefin conversion technology unit 1832 to be converted to additional ethylene and propylene, and in some cases a byproduct 1834.

In another aspect, provided herein is a method for producing olefins, comprising: (a) directing methane ($CH_4$) and oxygen ($O_2$) into an oxidative coupling of methane (OCM) reactor to produce a product stream comprising the $C_{2+}$ compounds including olefins, carbon monoxide (CO) and/or carbon dioxide ($CO_2$), and un-reacted $CH_4$; (b) enriching the CO and/or $CO_2$ from the product stream to generate an enriched CO and/or $CO_2$ stream; (c) directing the enriched CO and/or $CO_2$ stream to an MeOH reactor to produce MeOH; (d) directing at least some of the MeOH to a methanol to olefins (MTO) reactor to produce a second olefins stream; (e) enriching the un-reacted $CH_4$ from the product stream to produce an enriched $CH_4$ stream; and (f) directing at least a portion of the enriched $CH_4$ stream to a steam methane reformer (SMR) that produces hydrogen ($H_2$) and CO and/or $CO_2$. In some embodiments, the method further comprises (g) recovering olefins from the product stream and the second olefins stream.

In another aspect, provided herein is a system for producing olefins, comprising: (a) an oxidative coupling of methane (OCM) reactor that (i) receives methane ($CH_4$) and oxygen ($O_2$) and (ii) reacts the $CH_4$ and $O_2$ to yield a product stream comprising the $C_{2+}$ compounds including olefins, carbon monoxide (CO) and/or carbon dioxide ($CO_2$), and un-reacted $CH_4$; (b) an MeOH reactor that (i) receives CO and/or $CO_2$ enriched from the product stream and (ii) reacts the CO and/or $CO_2$ to produce MeOH; (c) a methanol to olefins (MTO) reactor that converts at least some of the MeOH into olefins to produce a second olefins stream; and (d) a steam methane reformer (SMR) that (i) receives un-reacted $CH_4$ enriched from the product stream and (ii) provides hydrogen ($H_2$) and at least one of carbon monoxide (CO) and $CO_2$ to the MeOH reactor to produce MeOH. In some embodiments, the system further comprises a separations module that enriches olefins from the product stream and the second olefins stream.

Oxidative Coupling of Methane Process

In an OCM process, methane ($CH_4$) may react with an oxidizing agent over a catalyst bed to generate $C_{2+}$ compounds. For example, methane can react with oxygen over a suitable catalyst to generate ethylene, e.g., $2\ CH_4 + O_2 \rightarrow C_2H_4 + 2\ H_2O$ (See, e.g., Zhang, Q., *Journal of Natural Gas Chem.*, 12:81, 2003; Olah, G. "Hydrocarbon Chemistry", Ed. 2, John Wiley & Sons (2003)). This reaction may be exothermic ($\Delta H = -280$ kJ/mol) and occur at very high temperatures (e.g., >450° C. or >700° C.). Non-selective reactions that can occur include (a) $CH_4 + 2O_2 \rightarrow CO_2 + 2\ H_2O$ and (b) $CH_4 + \frac{1}{2} O_2 \rightarrow CO + 2H_2$. These non-selective reactions may also be exothermic, with reaction heats of −891 kJ/mol and −36 kJ/mol respectively. The conversion of methane to COx products may be undesirable due to both heat management and carbon efficiency concerns.

Experimental evidence suggests that free radical chemistry may be involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) may be activated on the catalyst surface, forming methyl radicals which then couple on the surface or in the gas phase to form ethane ($C_2H_6$), followed by dehydrogenation to ethylene ($C_2H_4$). The OCM reaction pathway can have a heterogeneous/homogeneous mechanism, which involves free radical chemistry. Experimental evidence has shown that an oxygen active site on the catalyst activates the methane, removes a single hydrogen atom and creates a methyl radical. Methyl radicals may react in the gas phase to produce ethane, which may be either oxidative or non-oxidatively dehydrogenated to ethylene. The main reactions in this pathway can be as follows: (a) $CH_4 + O^- \rightarrow CH_3^* + OH^-$; (b) $2\ CH_3^* \rightarrow C_2H_6$; (c) $C_2H_6 + O^- \rightarrow C_2H_4 + H_2O$. In some cases, to improve the reaction yield, ethane can be introduced downstream of the OCM catalyst bed and thermally dehydrogenated via the following reaction: $C_2H_6 \rightarrow C_2H_4 + H_2$. This reaction is endothermic ($\Box H = 144$ kJ/mol), which can utilize the exothermic reaction heat produced during methane conversion. Combining these two reactions in one vessel can increase thermal efficiency while simplifying the process.

Catalysts for OCM, may include, e.g., various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and/or combinations thereof, on various supports. A number of doping elements may be used in combination with the above-mentioned catalysts.

Various limitations of the conventional approach to C—H bond activation may limit the yield of OCM reaction under practical operating conditions. For example, publications from industrial and academic labs have shown characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e., ethane and ethylene). In addition, almost all such reported yields required extremely high reactor inlet temperatures (>800° C.). Catalysts and processes adapted for performing OCM reaction at substantially more practicable temperatures, pressures and catalyst activities have been described in U.S. Patent Publication Nos. 2012/0041246, 2013/0023709, 2013/0165728, 2013/0158322, 2014/0121433, 2014/0274671, and 2015/0314267, each of which is incorporated herein by reference in its entirety for all purposes.

An OCM reactor can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed. In some embodiments, at least a portion of the OCM catalyst in at least a portion of the OCM reactor can include one or more OCM catalysts and/or nanostructure-based OCM catalyst compositions, forms and formulations. Examples of OCM reactors, separations for OCM, and OCM process designs are described in U.S. Patent Publication Nos. 2013/0225884, 2014/0107385, 2014/0012053, and 2015/0152025, each of which is incorporated herein by reference in its entirety for all purposes. An OCM reactor can be adiabatic or substantially adiabatic (including, for example, a post-bed cracking unit). An OCM reactor can be isothermal or substantially isothermal.

Figure 19:
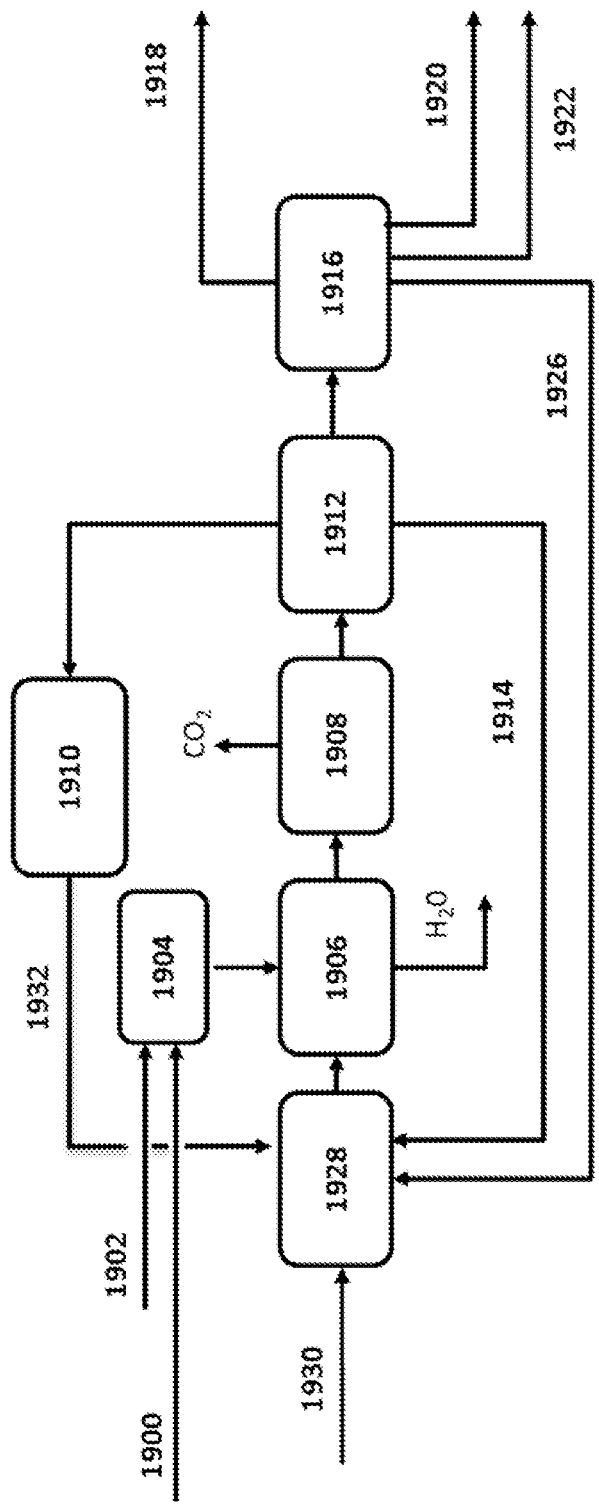
FIG. 19 is a schematic illustration of an example oxidative coupling of methane (OCM) process.

With reference to FIG. 19, natural gas 1900 and ethane 1902 can enter the process through a de-sulfurization module (or unit) 1904, which can flow into a process gas compression module 1906 where water can be removed. OCM product gas can be added to the process gas compression module 1906 as well. A process gas cleanup module 1908 can remove carbon dioxide ($CO_2$), some or all of which can be taken to a methanation module 1910. Following cleanup, the process gas can flow into a first separations module 1912 that removes $C_{2+}$ compounds from the process gas stream. The remaining process gas can flow to the methanation module 1910 and/or a fired heater (e.g., to heat incoming OCM gas streams 1914). The $C_{2+}$ compounds can be fractionated in a second separations module 1916 to produce ethylene ($C_2H_4$) 1918, $C_3$ compounds 1920, and $C_{4+}$ compounds 1922 for example. The second separations module 1916 can produce an ethane ($C_2H_6$) stream 1926 that can be returned to the OCM reactor 1928. At the OCM reactor 1928, oxygen 1930 can be reacted with methane from the methanation module 1932. Outside boundary limits (OSBL) systems may include a steam system, a boiler feed water system and a cooling water system.

Figure 20:
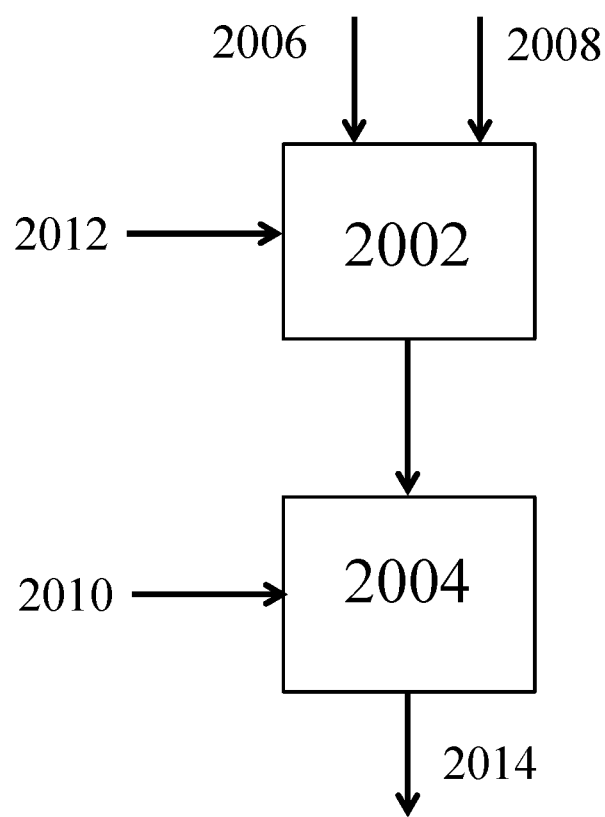
FIG. 20 is a schematic illustration of addition of ethane to an example OCM reactor.

The OCM reactor can perform the OCM reaction and a post-bed cracking (PBC) reaction, as described in U.S. Patent Publication No. 2015/0152025, which is incorporated herein by reference in its entirety. With reference to FIG. 20, the OCM reactor 2000 can have an OCM reaction section 2002 and a PBC section 2004. Methane 2006 (e.g., from natural gas) and oxygen 2008 can be injected (via a mixer) into the OCM reaction region (which comprises an OCM catalyst). The OCM reaction may be exothermic and the heat of reaction can be used to crack additional ethane 2010 that can be injected into the PBC region 2004. In some cases, yet more ethane 2012 can also be injected into the OCM reaction region 2002 and/or the methane feed is supplemented with ethane or other $C_{2+}$ alkanes (e.g., propane or butane). The OCM reactor may produce an OCM effluent 2014.

The relative amounts of supplemental ethane 2010 and 2012 can be varied to achieve a range of product outcomes from the system. In some cases, no ethane is injected into the OCM reaction region 2002 (referred to herein as Case-1). Another example presented herein has 3.5 mol % ethane injected into the OCM region (referred to herein as Case-2). Some process design results are presented in Table 1.

TABLE 1

Examples of various amounts of ethane in OCM feed

|  | Case-1 | Case-2 |
|---|---|---|
| Natural gas consumed (MMSCFD) | 15.5 | 16 |
| Ethane consumed (MMSCFD) | 2.2 | 8.3 |
| [Ethane] at inlet (mol %) | 0.07 | 3.5 |
| [Ethylene] at outlet (mol %) | 3.6 | 4.9 |
| $C_2$ products (kTa) | 85 | 115 |
| $C_3$ products (kTa) | 10.3 | 21.1 |
| $C_{4+}$ products (kTa) | 2.7 | 2.5 |
| $O_2$ consumed (ton/ton ethylene) | 2.2 | 1.8 |
| $CO_2$ produced from OCM (ton/ton ethylene) | 0.9 | 0.7 |
| $CO_2$ produced from fired heater (ton/ton ethylene) | 0.6 | 0.4 |

In some cases, an amount of hydrogen ($H_2$) exiting the OCM reactor is relatively higher for cases having relatively more ethane injection (e.g., 8% $H_2$ for Case-1 and about $H_2$ 10% for Case-2). The amount of ethane that can be injected can be limited by the desired temperature exiting the OCM reaction region 2002 or the OCM reactor 2014.

Methane can be combined with a recycle stream from downstream separation units prior to or during introduction into an OCM reactor. In the OCM reactor, methane can catalytically react with an oxidizing agent to yield $C_{2+}$ compounds. The oxidizing agent can be oxygen ($O_2$), which may be provided by way of air or enriched air. Oxygen can be extracted from air, for example, in a cryogenic air separation unit.

To carry out an OCM reaction in conjunction with some catalytic systems, the methane and oxygen containing gases may need to be brought up to appropriate reaction temperatures, e.g., in excess of 450° C. for some catalytic OCM processes, before being introduced to the catalyst, in order to allow initiation of the OCM reaction. Once that reaction begins or "lights off," then the heat of the reaction may be sufficient to maintain the reactor temperature at appropriate levels. Alternatively or additionally, these processes may operate at a pressure above atmospheric pressure, such as in the range of about 1 to 30 bars (absolute).

Once formed, $C_{2+}$ compounds can be subjected to further processing to generate one or more desired or otherwise predetermined chemicals. In some situations, alkane components of the $C_{2+}$ compounds are subjected to cracking in an OCM reactor or a reactor downstream of the OCM reactor to yield other compounds, such as alkenes (or olefins). See, e.g., U.S. Patent Publication No. 2015/0152025, which is entirely incorporated herein by reference.

The OCM effluent can be cooled after the conversion to ethylene has taken place. The cooling can take place within a portion of the OCM reactor and/or downstream of the OCM reactor (e.g., using at least about 1, 2, 3, 4, 5 or more heat exchangers). In some cases, a heat exchanger is a heat recovery steam generator (HRSG), such as the apparatus described herein. Cooling the OCM effluent suitably rapidly and to a suitably low temperature can prevent undesirable reactions from occurring with the OCM effluent, including, but not limited to the formation of coke or other by-products.

In some embodiments, the OCM effluent is cooled to a target temperature of less than or equal to about 700° C., 650° C., 600° C., 550° C., 500° C., 450° C., 400° C., 350° C., 300° C., ° C., 200° C., or less. In some cases, the OCM effluent is cooled to the target temperature less than or equal to about 1 second, 900 milliseconds (ms), 800 ms, 700 ms, 600 ms, 500 ms, 400 ms, 300 ms, 200 ms, 100 ms, 80 ms, 60 ms, 40 ms, 20 ms, or less of the production of the desired or otherwise predetermined concentration of a compound (e.g., ethylene) in the OCM reaction.

In some situations, an OCM system generates ethylene that can be subjected to further processing to produce different hydrocarbons with the aid of one or more conversion processes (or systems). Such a process can be part of an ethylene to liquids (ETL) process flow comprising one or more OCM reactors, separations units, and one or more conversion processes for generating higher molecular weight hydrocarbons. The conversion processes can be integrated in a switchable or selectable manner in which at least a portion or all of the ethylene containing product can be selectively directed to at least about 1, 2, 3, 4, 5, 6, 7, 8, 9, 10, or more different process paths to yield as many different hydrocarbon products. An example OCM and ETL (collectively "OCM-ETL" herein) is provided in U.S. Patent Publication No. 2014/0171707, which is entirely incorporated herein by reference.

An aspect of the present disclosure provides OCM processes that are configured to generate olefins (or alkenes), such as ethylene, propylene (or propene), butylenes (or butenes), etc. An OCM process can be a standalone process or can be integrated in a non-OCM process, such as a natural gas liquid(s) (NGL or NGLs) or gas processing system.

Reference will now be made to the figures, wherein like numerals refer to like parts throughout. It will be appreciated that the figures and features therein are not necessarily drawn to scale. In the figures, the direction of fluid flow between units is indicated by arrows. Fluid may be directed from one unit to another with the aid of valves and a fluid flow system. In some examples, a fluid flow system can include compressors and/or pumps, as well as a control system for regulating fluid flow, as described elsewhere herein.

In some cases, the process equipment is sized to accommodate a range of amounts of additional ethane such that the process is flexible. For example, more ethane can be injected into the process when the price of ethane is relatively cheap in comparison to the price of natural gas (e.g., low frac spread).

The ethane can be mixed with the natural gas and recycled to the OCM unit. The ethane can go straight to the OCM reactor, optionally through a separate de-sulfurization module. Injection of ethane through a separate de-sulfurization module can reduce the load in the recycle loop of the process and/or give additional production capacity keeping the same recirculation rate. The purge gas from the process can be used for fuel gas to the fired heater or sales gas.

The concentration of ethane in the feed to the OCM reactor can be any suitable value, including greater than or equal to about 0.0 mol %, 0.25 mol %, 0.5 mol %, 0.75 mol %, 1.0 mol %, 1.25 mol %, 1.5 mol %, 1.75 mol %, a 2.0 mol %, 2.25 mol %, 2.5 mol %, 2.75 mol %, 3.0 mol %, 3.25 mol %, 3.5 mol %, 3.75 mol %, 4.0 mol %, 4.25 mol %, 4.5 mol %, 4.75 mol %, 5.0 mol %, 25 mol %, 5.5 mol %, 5.75 mol %, 6.0 mol %, 7.0 mol %, 8.0 mol %, 9.0 mol %, 10.0 mol % or more. In some cases, the concentration of ethane in the feed to the OCM reactor is less than or equal to about 25 mol %, 20 mol %, 15 mol %, 10 mol %, 9 mol %, 8 mol %, 7 mol %, 6 mol %, 5 mol %, 4 mol %, 3 mol %, 2 mol %, 1 mol %, 0.8 mol %, 0.6 mol %, 0.4 mol %, 0.2 mol %, 0.1 mol % or less. In some cases, the concentration of ethane in the feed to the OCM reactor is between any of the two values described above, for example, between about 0.01 mol % to about 5 mol %.

The systems and methods of the present disclosure can be carbon-efficient and/or energy-efficient. In some cases, the systems or methods of the present disclosure have a carbon efficiency of at least about 50%, at least about 55%, at least about 60%, at least about 65%, at least about 70%, at least about 75%, at least about 80%, at least about 85%, at least about 90%, or more. In some cases, a system of the present disclosure or method for use thereof has a ratio of all carbon atoms output from the system as hydrocarbons to all carbon atoms input to the system of at least about 0.40, at least about 0.50, at least about 0.55, at least about 0.60, at least about 0.65, at least about 0.70, at least about 0.75, at least about 0.80, at least about 0.85, at least about 0.90, at least about 0.95, or more.

In some cases, the systems or methods of the present disclosure have a carbon efficiency of between about 50% and about 85%, between about 55% and about 80%, between about 60% and about 80%, between about 65% and about 85%, between about 65% and about 80%, or between about 70% and about 80%. In some cases, a system of the present disclosure or method for use thereof has a ratio of all carbon atoms output from the system as hydrocarbons to all carbon atoms input to the system of between about 0.50 and about 0.85, between about 0.55 and about 0.80, between about 0.60 and about 0.80, between about 0.65 and about 0.85, between about 0.65 and about 0.80, or between about 0.70 and about 0.80.

In some cases, the systems and methods combine OCM reaction, post-bed cracking (PBC), separations and methanation reactions. The separations can include oligomerization of ethylene to $C_{3+}$ compounds, which are more easily separated as described in PCT Patent Publication No. WO/2015/105911, which is incorporated herein by reference in its entirety. Additional details of OCM reactor and process design can be found in PCT Patent Publication Nos. WO/2015/081122 and WO/2015/106023, each of which is incorporated herein by reference in their entirety.

In an aspect, provided herein is a method for performing oxidative coupling of methane (OCM). The method can comprise (a) reacting oxygen ($O_2$) with methane ($CH_4$) to form heat, ethylene ($C_2H_4$) and optionally ethane ($C_2H_6$), hydrogen ($H_2$), carbon monoxide (CO) or carbon dioxide ($CO_2$); (b) reacting the heat produced in (a) with ethane ($C_2H_6$) to form ethylene ($C_2H_4$) and hydrogen ($H_2$); (c) performing at least one of (i) enriching the ethylene ($C_2H_4$) produced in (a) and (b) or (ii) oligomerizing the ethylene ($C_2H_4$) produced in (a) and (b) to produce $C_{3+}$ compounds and enriching the $C_{3+}$ compounds; and (d) reacting the hydrogen ($H_2$) produced in (a) and (b) with carbon monoxide (CO) and/or carbon dioxide ($CO_2$) to form methane ($CH_4$).

In another aspect, provided herein is a system for performing oxidative coupling of methane (OCM). The system can comprise an OCM reactor that permits oxygen ($O_2$) and methane ($CH_4$) to react in an OCM process to form heat, ethylene ($C_2H_4$) and optionally ethane ($C_2H_6$), hydrogen ($H_2$), carbon monoxide (CO) or carbon dioxide ($CO_2$). The system can further comprise a cracking vessel in fluid communication with the OCM reactor, which cracking vessel may utilize the heat produced in the OCM reactor to convert ethane ($C_2H_6$) into ethylene ($C_2H_4$) and hydrogen ($H_2$). The system can further comprise a separations module in fluid communication with the cracking vessel. The separations module may (i) enrich the ethylene ($C_2H_4$) produced in the OCM reactor and the cracking vessel or (ii) oligomerize the ethylene ($C_2H_4$) produced in the OCM reactor and the cracking vessel to produce $C_{3+}$ compounds and enriches the $C_{3+}$ compounds. The system can further comprise a methanation reactor in fluid communication with the separations module. The methanation reactor may permit the hydrogen ($H_2$) produced in the OCM reactor and the cracking vessel to react with carbon monoxide (CO) and/or carbon dioxide ($CO_2$) to form methane ($CH_4$).

In some cases, the ethane ($C_2H_6$) that is cracked in the cracking vessel is produced in the OCM reactor. In some instances, at least some of the ethane ($C_2H_6$) that is cracked is in addition to the ethane ($C_2H_6$) that was produced in the OCM reactor. In some cases, the OCM reactor produces ethane ($C_2H_6$), hydrogen ($H_2$), carbon monoxide (CO) and carbon dioxide ($CO_2$). In some cases, the carbon monoxide (CO) and carbon dioxide ($CO_2$) produced in the OCM reactor is methanated. The separations module can separate ethylene ($C_2H_4$) or $C_{3+}$ compounds from methane ($CH_4$), ethane ($C_2H_6$), hydrogen ($H_2$), carbon monoxide (CO) or carbon dioxide ($CO_2$). In some instances, the cracking vessel is a portion of the OCM reactor.

The methane formed in the methanation reactor can be returned to the OCM reactor or sold as sales gas. In some embodiments, the OCM reactor has an OCM catalyst. In some embodiments, the methanation reactor has a methanation catalyst. In some embodiments, the separations module comprises an ethylene-to-liquids (ETL) reactor comprising an oligomerization catalyst. At least some of the heat produced in the OCM reactor can be converted to power.

In another aspect, described herein is a method for producing $C_{2+}$ compounds from methane ($CH_4$). The method can comprise: (a) performing an oxidative coupling of methane (OCM) reaction which converts methane ($CH_4$) and oxygen ($O_2$) into ethylene ($C_2H_4$) and optionally ethane ($C_2H_6$); (b) optionally oligomerizing the ethylene ($C_2H_4$) to produce $C_{3+}$ compounds; and (c) isolating the $C_{2+}$ compounds, wherein the $C_{2+}$ compounds may comprise the ethylene ($C_2H_4$), the ethane ($C_2H_6$) and/or the $C_{3+}$ compounds. In some cases, the method has a carbon efficiency of at least about 50%, 60%, 70%, 80%, 90%, 95%, or more. In some cases, the isolated the $C_{2+}$ compounds are not pure. In some cases, the isolated the $C_{2+}$ compounds comprise methane, CO, $H_2$, $CO_2$ and/or water.

In some cases, the systems or methods of the present disclosure consume less than or equal to about 150, 140, 130, 120, 110, 100, 95, 90, 85, 80, 75, 70, 65, 60, 55, or 50, or less million British Thermal Units (MMBtu) of energy per ton of ethylene ($C_2H_4$) or $C_{3+}$ compounds enriched. In some cases, the amount of energy consumed by the system includes the energy content of the feedstock used to make the ethylene ($C_2H_4$) or $C_{3+}$ compounds.

In some cases, the systems or methods of the present disclosure have consume between about 65 and about 100, between about 70 and about 110, between about 75 and about 120, between about 85 and about 130, between about 40 and about 80, or between about 50 and about 80 MMBtu of energy per ton of ethylene ($C_2H_4$) or $C_{3+}$ compounds enriched. In some cases, the amount of energy consumed by the system includes the energy content of the feedstock used to make the ethylene ($C_2H_4$) or $C_{3+}$ compounds.

In some cases, the systems or methods of the present disclosure have a specific oxygen consumption of greater than or equal to about 1.2, about 1.3, about 1.4, about 1.5, about 1.6, about 1.7, about 1.8, about 1.9, about 2.0, about 2.1, about 2.2, about 2.3, about 2.4, about 2.5, about 2.6 about 2.7, about 2.8, about 2.9, about 3, about 3.2, about 3.4, about 3.6, about 3.8, about 4.0, or more.

In some cases, the systems or methods of the present disclosure have a specific oxygen consumption of between about 1.2 and about 2.7, between about 1.5 and about 2.5, between about 1.7 and about 2.3 or between about 1.9 and about 2.1.

In some cases, the systems or methods of the present disclosure have a specific $CO_2$ emission of greater than or equal to about 0.5, about 0.6, about 0.7, about 0.8, about 0.9, about 1.0, about 1.1, about 1.2, about 1.3, about 1.4, about 1.5, about 1.6, about 2.0, about 2.2, about 2.4, about 2.6, about 2.8, about 3.0, about 3.2, about 3.4, about 3.6, or more.

In some cases, the systems or methods of the present disclosure have a specific $CO_2$ emission of between about 0.5 and about 1.7, between about 0.7 and about 1.4, between about 0.8 and about 1.3 or between about 0.9 and about 1.1.

In some cases, the systems or methods of the present disclosure produces $C_{2+}$ products, and the $C_{2+}$ products comprise at least about 1%, 2.5%, 5%, 7.5%, 10%, 12.5%, 15%, 17.5%, 20% (wt % or mol %) or more $C_{3+}$ hydrocarbons.

In some cases, the systems or methods of the present disclosure produces $C_2$ products and $C_{3+}$ products, and a molar ratio of the $C_2$ products to the $C_{3+}$ products is at least or equal to about 2, 3, 4, 5, 6, 7, 8, 9, 10, 11, 12, 13, 14, 15, 16, 17, 18, 19, 20 or more. In some cases, the molar ratio of the $C_2$ products to the $C_{3+}$ products is less than or equal to about 50, 45, 40, 35, 30, 25, 20, 18, 16, 14, 12, 10, 8, 6, 4, 2, or less. In some cases, the molar ratio of the $C_2$ products to the $C_{3+}$ products is between any of the two values described above, for example, from about 5 to about 20.

In another aspect, provided herein is a method for producing $C_{2+}$ compounds from methane ($CH_4$), the method comprising: (a) performing an oxidative coupling of methane (OCM) reaction which may convert methane ($CH_4$) and oxygen ($O_2$) into ethylene ($C_2H_4$) and optionally ethane ($C_2H_6$); (b) optionally oligomerizing the ethylene ($C_2H_6$) to produce $C_{3+}$ compounds; and (c) isolating the $C_{2+}$ compounds, wherein the $C_{2+}$ compounds may comprise the ethylene ($C_2H_4$), the ethane ($C_2H_6$) and/or the $C_{3+}$ compounds. In some cases, the amount of energy consumed by the system includes the energy content of the feedstock used to make the isolated $C_{2+}$ compounds. In some cases, the isolated $C_{2+}$ compounds are not pure. In some cases, the isolated the $C_{2+}$ compounds comprise methane, CO, $H_2$, $CO_2$ and/or water.

In some cases, the method consumes less than or equal to about 150, 140, 130, 120, 110, 100, 95, 90, 85, 80, 75, 70, 65, 60, 55, 50, or less MMBtu of energy per ton of $C_{2+}$ compounds isolated. In some cases, the method consumes greater than or equal to about 20, 30, 40, 50, 60, 70, 80, 90, 100, or more MMBtu of energy per ton of $C_{2+}$ compounds isolated. In some cases, the method consumes between about 65 and about 100, between about 70 and about 110, between about 75 and about 120, between about 85 and about 130, between about 40 and about 80, or between about 50 and about 80 MMBtu of energy per ton of $C_{2+}$ compounds isolated.

In another aspect, provided herein is a method for producing $C_{2+}$ compounds from methane ($CH_4$). The method may comprise performing an oxidative coupling of methane (OCM) reaction using an OCM catalyst. The OCM reaction may be performed at a set of reaction conditions to convert a quantity of methane ($CH_4$) into ethylene ($C_2H_4$) at a carbon efficiency. The OCM catalyst may have a $C_{2+}$ selectivity at the set of reaction conditions that is less than the carbon efficiency at the set of reaction conditions. The set of reaction conditions can include a temperature, a pressure, a methane to oxygen ratio and a gas hourly space velocity (GHSV).

In another aspect, provided herein is a method for producing $C_{2+}$ compounds from methane ($CH_4$). The method may comprise (a) performing an oxidative coupling of methane (OCM) reaction using an OCM catalyst at a set of reaction conditions to convert a quantity of methane ($CH_4$) into ethylene ($C_2H_4$) and ethane ($C_2H_6$); and (b) cracking the ethane ($C_2H_6$) to produce additional ethylene ($C_2H_4$). The combined carbon efficiency of (a) and (b) may be greater than the $C_{2+}$ selectivity of the OCM catalyst at the set of reaction conditions. The set of reaction conditions can include a temperature, a pressure, a methane to oxygen ratio and a gas hourly space velocity (GHSV).

In some instances, the $C_{2+}$ selectivity is less than or equal to about 70%, 65%, 60%, 55%, 50%, 45%, 40%, 35%, 30% or less. In some instances, the $C_{2+}$ selectivity is greater than or equal to about 20%, 25%, 30%, 35%, 40%, 50%, 60%, 70%, 80%, or more. In some cases, the $C_{2+}$ selectivity is between any of the two values described herein, for example, from about 25% to about 50%.

In another aspect, provided herein is a method for producing $C_{2+}$ compounds. The method may comprise a) providing a first feedstock comprising methane ($CH_4$) and optionally a first amount of ethane ($C_2H_6$); (b) performing an OCM reaction on the first feedstock to produce an OCM product comprising a first amount of ethylene ($C_2H_4$); (c) combining the OCM product with a second feedstock comprising a second amount of ethane ($C_2H_6$) to produce a third feedstock; and (d) cracking the third feedstock to produce a second amount of ethylene ($C_2H_4$). In some cases, the second amount of ethylene includes ethylene produced in (b) and (d).

In some cases, the fraction of the second amount of ethylene ($C_2H_4$) that is derived from the first or the second amounts of ethane ($C_2H_6$) is at least about 1%, at least about 3%, at least about 5%, at least about 7%, at least about 10%, at least about 15%, at least about 20%, at least about 25%, at least about 30%, at least about 35%, at least about 40%, at least about 45%, at least about 50%, at least about 55%, or more.

In some cases, the combined moles of the first amount and second amount of ethane ($C_2H_6$) divided by the combined moles of the first feedstock and the second feedstock is greater than or equal to about 1%, 3%, 5%, 7%, 10%, 15%, 20%, 25%, 30%, 35%, 40%, 45%, 50%, 55%, 60%, or more. In some cases, the combined moles of the first amount and second amount of ethane ($C_2H_6$) divided by the combined moles of the first feedstock and the second feedstock is less than or equal to about 90%, 80%, 70%, 60%, 50%, 40%, 30%, 20%, 10% or less.

In some cases, the combined moles of the first amount and second amount of ethane ($C_2H_6$) divided by the combined moles of the first feedstock and the second feedstock is between about 1% and about 50%, between about 1% and about 40%, between about 1% and about 30%, between about 1% and about 20%, between about 1% and about 15%, between about 1% and about 10%, or between about 10% and about 50%.

In some cases, the first feedstock is natural gas. In some cases, the first feedstock is natural gas supplemented with the first amount of ethane ($C_2H_6$). In some cases, the first feedstock is natural gas having passed through a separations system to substantially remove the hydrocarbons other than methane.

In some cases, the molar percent of ethane ($C_2H_6$) in methane ($CH_4$) in the first feedstock is greater than or equal to about 1%, 3%, 5%, 7%, 10%, 15%, 20%, or more.

In some cases, some or all of a methane-containing feed stream (e.g., natural gas) can be processed in a separation system prior to being directed into an OCM reactor. Directing a methane-containing feed stream into an OCM reactor via a separation system or subsystem rather than into an OCM reactor directly can provide advantages, including but not limited to increasing the carbon efficiency of the process, optimizing the OCM process for methane processing, and optimizing the post-bed cracking (PBC) process for ethane processing. Such a configuration can result in higher back-end sizing for the system. In some cases (e.g., when using high pressure pipeline natural gas as a feedstock, high recycle ratio), the back-end sizing increase can be reduced or moderated. The separation system or subsystem can comprise a variety of operations including any discussed in the present disclosure, such as $CO_2$ removal via an amine system, caustic wash, dryers, demethanizers, deethanizers, and $C_2$ splitters. In some cases, all of the methane and ethane in the methane-containing feed stream (e.g., natural gas) passes through a separations system or separations subsystem prior to passing through an OCM reactor. Some or all of the ethane from the feed stream can be directed from the separation system or subsystem into the inlet of an OCM reactor or into a post-bed cracking (PBC) unit.

In some configurations, an OCM system can be operated in a cycle, with at least some of the products from one unit or subsystem being processed or reacted in the next unit or subsystem. For example, oxygen ($O_2$) and methane ($CH_4$) feed can be provided to an OCM reactor, which produces an OCM product stream comprising ethane ($C_2H_6$), ethylene ($C_2H_4$), carbon monoxide (CO) and/or carbon dioxide ($CO_2$), and heat. The OCM product stream can then be fed into an ethane conversion subsystem (e.g., a cracking vessel or an ethane cracker) in fluid communication with the OCM reactor. The ethane conversion subsystem can also receive an additional $C_2H_6$ stream. The ethane conversion subsystem can convert $C_2H_6$ (e.g., crack $C_2H_6$ to $C_2H_4$) with the aid of the heat liberated by the OCM reaction. The heat can also be used to crack the $C_2H_6$ in the additional $C_2H_6$ stream. A $C_2H_4$ product stream can then be directed from the ethane conversion subsystem into a separations module in fluid communication with the ethane conversion subsystem. The separations module can enrich products such as $C_2H_4$ in the product stream. The separations module can also oligomerize $C_2H_4$ to form compounds comprising three or more carbon atoms ($C_{3+}$ compounds). An enriched product stream enriched in $C_2H_4$ and/or $C_{3+}$ compounds can be recovered from the separations module. A lights stream comprising components such as hydrogen ($H_2$) (e.g., hydrogen generated from the cracking of $C_2H_6$) and CO and/or $CO_2$ can be recovered from the separations module and directed into a methanation reactor in fluid communication with the separations module. The methanation reactor can react $H_2$ with CO and/or $CO_2$ to form a methanated stream comprising $CH_4$. The methanated stream can then be directed into the OCM reactor to provide additional methane for the OCM process. In some cases, energy generated in the methane conversion section in the form of high pressure steam, high temperature steam, heat, electricity, heat transferred via gas-gas heat exchanger, heat transferred via gas-liquid heat exchanger, or other forms, can be used to provide all of the energy and power required to run the entire plant or system.

In some cases, a cyclical system or process can operate with a carbon efficiency such as those discussed in this disclosure. For example, such a system or process can operate with a carbon efficiency of greater than or equal to about 50%, 55%, 60%, 65%, 70%, 75%, 80%, 85%, 90%, or more. In some cases, such a system or process can operate with a carbon efficiency of between about 50% and about 85%, between about 55% and about 80%, between about 60% and about 80%, between about 65% and about 85%, between about 65% and about 80%, or between about 70% and about 80%.

In some cases, such a system or process (or method) can operate such that a ratio of all carbon atoms output from the system as hydrocarbons to all carbon atoms input to the system is greater than or equal to about 0.50, 0.55, 0.60, 0.65, 0.70, 0.75, 0.80, 0.85, 0.90, or more. In some cases, such a system or process can operate such that a ratio of all carbon atoms output from the system as hydrocarbons to all carbon atoms input to the system is between about 0.50 and about 0.85, between about 0.55 and about 0.80, between about 0.60 and about 0.80, between about 0.65 and about 0.85, between about 0.65 and about 0.80, or between about 0.70 and about 0.80.

An example process can comprise an OCM unit, a process gas compressor, a process gas cleanup unit, a cryogenic separations unit, a fractionation unit, a methanation unit, and a sulfur-removal unit. An oxygen stream may be fed into the OCM unit, along with a $C_1$ recycle stream from the methanation unit and a $C_2$ recycle stream from the fractionation unit. A natural gas stream and an ethane stream may be fed into the sulfur removal unit. Output from the OCM unit and the sulfur removal unit may be directed into the process gas compressor, and then into the process gas cleanup unit, which removes a $CO_2$ stream. The remaining product stream may be directed into the cryogenic separations unit, where light components including $H_2$ and CO or $CO_2$ may be directed into the methanation unit, and the remaining product stream, including ethylene and other $C_{2+}$ compounds, may be directed into the fractionation unit. The fractionation unit may be configured to separate an ethylene stream and a $C_{3+}$ compound stream comprising $C_3$ compounds, $C_4$ compounds, and $C_{5+}$ compounds, as well as the $C_2$ recycle which may be directed back to the OCM unit. The methanation unit may convert the light components into methane, a first portion of which may be recycled to the OCM unit and a second portion of which may be output as sales gas. The operating flow rates for the input streams may be as follows: 20.3 MT/h of oxygen, 16.0 MT/h of natural gas, and 2.9 MT/h of ethane. The operating flow rates for the output streams may be as follows: 9.0 MT/h of ethylene, 1.4 MT/h of $C_{3+}$ compounds, 4.3 MT/h of sales gas, and 8.2 MT/h of $CO_2$. The corresponding carbon content of the input streams may be 972 kmol/h of carbon in the natural gas stream, and 194 kmol/h of carbon in the ethane stream. The corresponding carbon content of the output streams may be 642 kmol/h of carbon in the ethylene stream, 96 kmol/h of carbon in the $C_{3+}$ compounds stream, 247 kmol/h of carbon in the sales gas stream, and 181 kmol/h of carbon in the $CO_2$ stream. The amount of carbon input to the system may be 1166 kmol/h, and the amount of carbon output from the system in hydrocarbon products (e.g., excluding $CO_2$) is 985 kmol/h, for a resulting carbon efficiency of 84.5%.

Reaction heat (e.g., OCM reaction heat) can be used to supply some, most, or all of the energy used to operate systems and perform processes of the present disclosure. In some examples, reaction heat can be used to supply greater than or equal to about 50%, 55%, 60%, 65%, 70%, 75%, 80%, 85%, 90%, 95%, 96%, 97%, 98%, 99%, or 100% of energy for operating systems and performing processes of the present disclosure. For example, the reaction heat can be used to supply at least about 80% or 90% of all of the energy for operating systems or processes of the present disclosure. This can provide for an efficient, substantially self-contained system with reduced or even minimum external energy input.

Integration of OCM with an FCC

The systems and methods described herein can be implemented in a number of scenarios, including using feedstocks from refineries (e.g., FCC offgas).

Figure 21A:
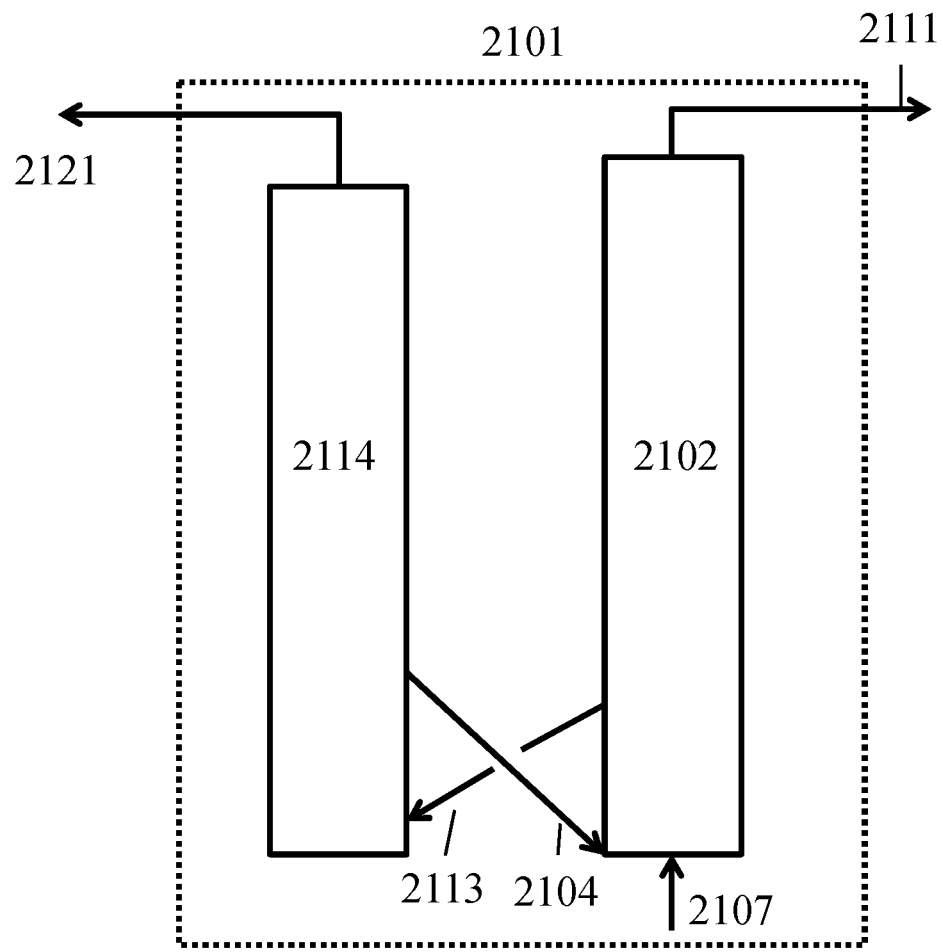
FIG. 21A shows an example of a fluidized catalytic cracker (FCC) unit.
Figure 21B:
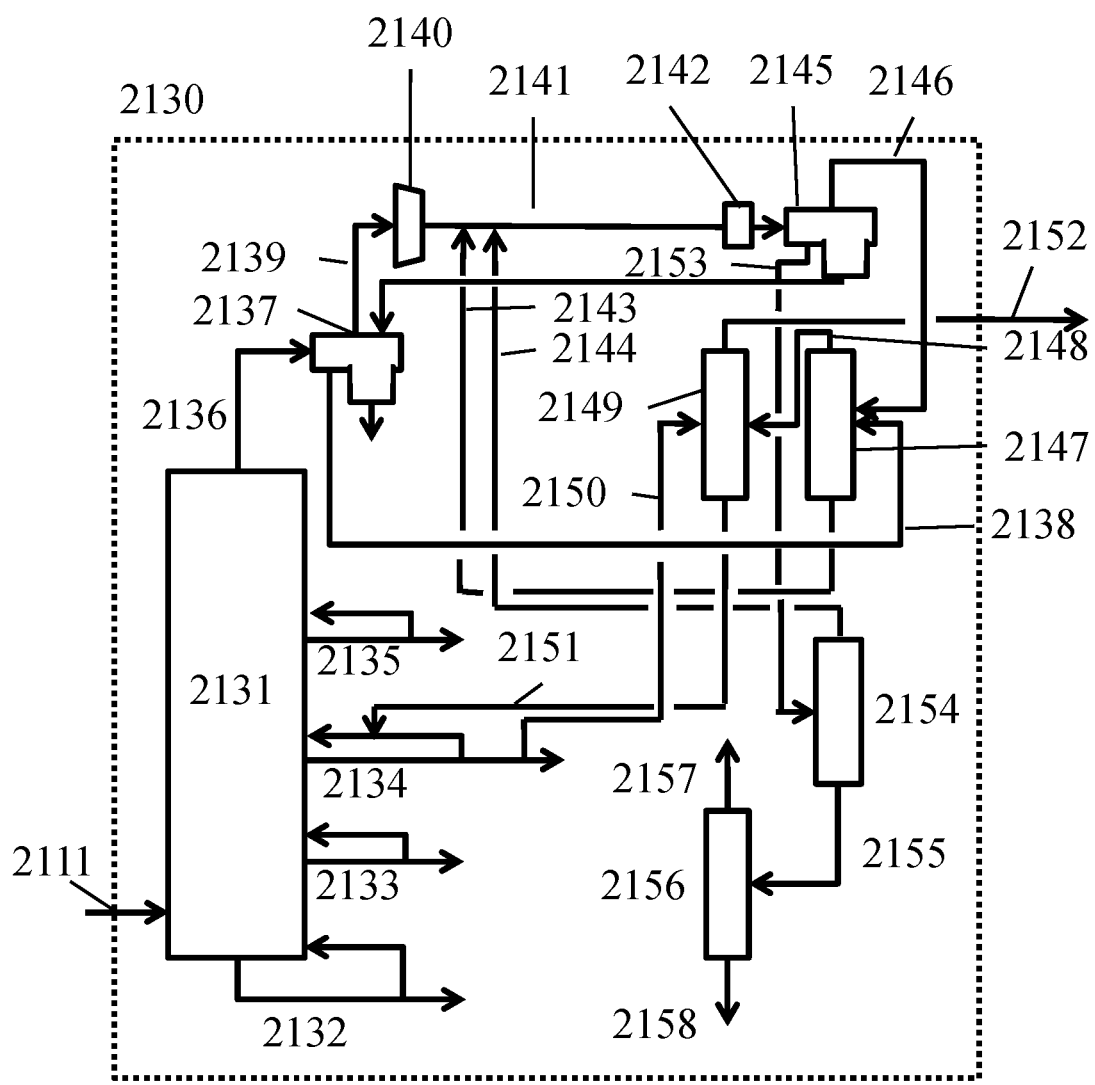
FIG. 21B shows an example of a separations train.
Figure 21C:
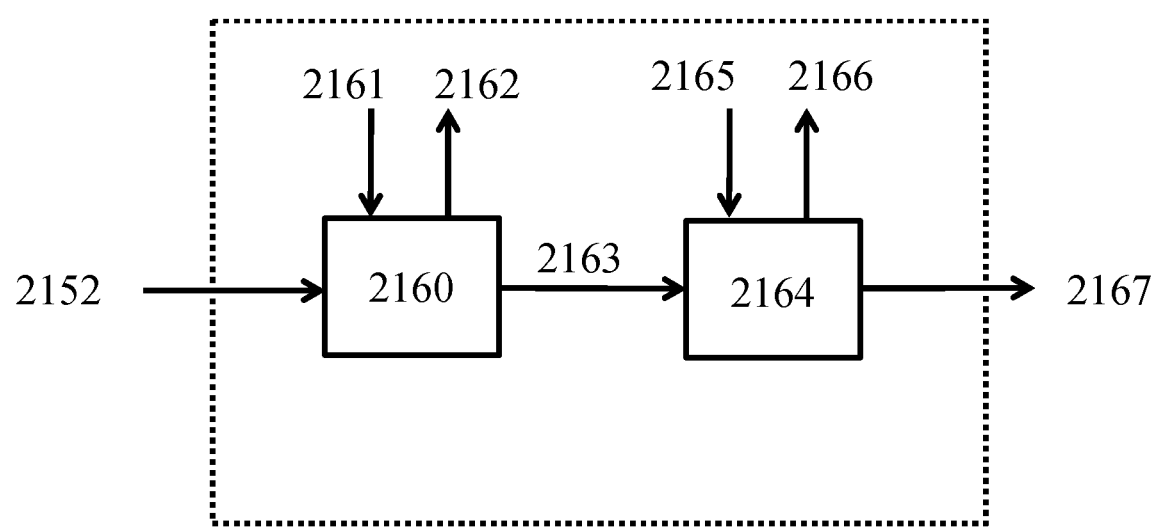
FIG. 21C shows an example of treatment of FCC off-gas.

FIGS. 21A-21C shows a refinery system comprising a fluid catalytic cracking (FCC) unit 2101 and a separations unit 2130. The FCC unit can comprise an FCC reactor 2102, and in some cases a catalyst regeneration unit 2114, as shown for example in FIG. 21A. In the FCC reactor, a hydrocarbon feed stream (e.g., raw oil) can be contacted with a regenerated cracking catalyst entering from a regenerated catalyst standpipe 2104. The hydrocarbon feed stream can contact the catalyst in a riser, which can extend to the bottom of a reactor vessel. The feed and catalyst can be fluidized, for example by gas from a fluidizing line 2107.

In some cases, heat from the catalyst vaporizes the hydrocarbon feed, and which is then cracked in the presence of the catalyst to produce lighter molecular weight hydrocarbon products as the catalyst and hydrocarbon feed are transferred up the riser into the reactor vessel. Side reactions can occur in the riser, depositing coke on the catalyst and lowering catalyst activity.

The light hydrocarbon products can then be separated from the coked catalyst, for example using cyclonic separators. Cyclonic separators can include a primary separator and one, two, or more stages of cyclones in the reactor vessel. After separation from the catalyst, gaseous cracked light hydrocarbon products exit the reactor vessel through a product outlet along a stream 2111 and are transported downstream to the separations unit 2130, as shown in FIG. 21B.

Spent or coked catalyst can be regenerated for further use. For example, coked cracking catalyst, after separation from the gaseous product hydrocarbons, can be sent into a stripping section, where steam is injected (e.g., through a nozzle) to purge residual hydrocarbon vapor. After the stripping operation, the coked catalyst can be transported to the catalyst regeneration unit 2114 through a spent catalyst standpipe 2113. The catalyst regeneration unit can comprise a combustor or other types of regenerators. In the catalyst regeneration unit, a stream of oxygen-containing gas, such as air, can be introduced through an air distributor to contact the coked catalyst, thereby combusting the coke from the coked catalyst to yield regenerated catalyst and flue gas. The catalyst regeneration process can add heat to the catalyst, which can provide energy for the endothermic cracking reactions.

Catalyst and air can flow together up a combustor riser located within the catalyst regenerator. After regeneration, the catalyst and air can be initially separated by discharge through a disengager. Additional recovery of regenerated catalyst and flue gas exiting the disengager can be achieved using first and second stage separator cyclones within the catalyst regeneration unit. Catalyst separated from flue gas can be dispensed through diplegs from the first and second stage separator cyclones. Regenerated catalyst can be carried back to the riser through the regenerated catalyst standpipe. Flue gas, relatively lighter in catalyst, can sequentially exit the cyclones and the regenerator vessel through a flue gas outlet along flue gas stream 2121. The flue gas can contain components including CO, $CO_2$, $N_2$ and $H_2O$, and other species.

The separations unit 2130 can be in downstream communication with the product outlet 2110. In the separations unit 2130, the gaseous cracked light FCC products in line 2111 can be directed to a lower section of a main fractionation column 2131, which can be in downstream communication with the product outlet 2110. Several different fractions of FCC product can be separated and taken from the main fractionation column, including but not limited to a heavy slurry oil stream 2132 from the bottoms, a heavy cycle oil stream 2133, a light cycle oil stream 2134, and a heavy naphtha stream 2135. Any or all of streams 2132, 2133, 2134, and 2135 may be cooled and pumped back to the main fractionation column 2131, typically at a higher location, to cool the main column.

Gasoline and gaseous light hydrocarbons can be removed in overhead stream 2136 from the main fractionation column 2131 and condensed before entering a main column receiver 2137. The main column receiver 2137 can be in downstream communication with the product outlet 2110, and the main column 2131 can be in upstream communication with the main column receiver 2137. An aqueous stream can be removed from a boot in the main column receiver 2137. A condensed light naphtha stream can removed in stream 2138 and an overhead stream 2139 can also be removed. The overhead stream 2139 can contain gaseous light hydrocarbons, which can comprise a dilute ethylene stream.

The streams 2138 and 2139 can be directed to a vapor recovery section 2142 of the separations unit. The vapor recovery section 2142 can comprise an absorption based system, or any other vapor recovery system such as a cold box system. The gaseous stream 2139 can be compressed in a compressor 2140, which can improve separation of light gas components. More than one compressor stage can be used, such as a dual stage compression. The compressed light hydrocarbon stream 2141 can be joined by streams 2121 and 2144, then chilled and delivered to a high pressure receiver 2145. An aqueous stream from the high pressure receiver 2145 can then be routed to the main column receiver 2137. A gaseous hydrocarbon stream 2146 comprising the dilute ethylene stream can be routed from the high pressure receiver to a primary absorber 2147 in which it can be contacted with unstabilized gasoline 2138 from the main column receiver 2137 to effect a separation between $C_{3+}$ and $C_{2-}$ hydrocarbons. The primary absorber 2147 can be in downstream communication with the main column receiver 2137. A liquid $C_{3+}$ stream 2143 can be returned to the compressed hydrocarbon stream 2141 prior to chilling.

A primary off-gas stream 2148 from the primary absorber 2147 can comprise the dilute ethylene stream. To concentrate the ethylene stream further and recover heavier components, the primary off-gas stream 2148 can be directed to a secondary absorber 2149, where a circulating stream of light cycle oil 2150 diverted from stream 2134 can absorb most of the remaining $C_{5+}$ and some $C_3$-$C_4$ material in the primary off-gas stream. The secondary absorber 2149 can be in downstream communication with the primary absorber 2147. Light cycle oil from the bottom of the secondary absorber 2151, richer in $C_{3+}$ material, can be returned to the main fractionation column 2131 via the pump-around for stream 2134. The overhead of the secondary absorber 2149 can comprise a dry gas of predominantly $C_{2-}$ hydrocarbons with hydrogen sulfide, ammonia, carbon oxides, and hydrogen, and can be removed in a secondary off-gas stream 2152 to comprise a dilute ethylene stream. A product stream containing ethylene from the separations unit 2130, such as stream 2152, can be processed by various techniques, including those discussed further herein.

Liquid 2153 from the high pressure receiver 2145 can be sent to a stripper 2154. Most of the $C_{2-}$ can be removed in the overhead of the stripper 2154 and returned the compressed hydrocarbon stream 2141 via overhead stream 2144. A liquid bottoms stream 2155 can be sent from the stripper 2154 to a debutanizer column 2156. An overhead stream 2157 from the debutanizer can comprise $C_3$-$C_4$ olefinic product, while a bottoms stream 2158 can comprise stabilized gasoline and can be further treated and sent to gasoline storage.

The dilute ethylene stream and/or FCC dry gas stream can be used as a feedstock for OCM as described herein, including OCM integrated with another process. The dilute ethylene stream can comprise an FCC dry gas stream, comprising between 5 weight-percent (wt %) and 50 wt % ethylene (in some cases, 10 wt % to 30 wt % ethylene). The dilute ethylene stream can comprise methane, for example at a concentration between 25 wt % and 55 wt %. The dilute ethylene stream can comprise ethane, for example at a concentration between 5 wt % and 45 wt %. The dilute ethylene stream can comprise propylene, for example at a concentration of between 0.1 wt % and 20 wt % propylene (in some cases, 0.5 wt % to 6 wt %). The dilute ethylene stream can comprise hydrogen and/or nitrogen, for example at a concentration between 1 wt % and 25 wt % each (in some cases, between 5 wt % and 20 wt % each). Saturation levels of water can also be present in the dilute ethylene stream. In some cases, if a secondary absorber 2149 is used, no more than 5 wt % of $C_{3+}$ compounds can be present, with typically less than 0.5 wt % propylene. Besides hydrogen, other impurities such as hydrogen sulfide, ammonia, carbon oxides and acetylene can also be present in the dilute ethylene stream.

Many impurities in a dry gas ethylene stream can poison a catalyst. The secondary off-gas stream 2152, comprising a dilute ethylene stream, can be introduced into an amine absorber unit 2160 to lower concentrations of hydrogen sulfide (see, e.g., FIG. 21C). A lean aqueous amine solution 2161, for example comprising monoethanol amine or diethanol amine, can be introduced the amine absorber unit 2160 and contacted with the flowing secondary off-gas stream to absorb hydrogen sulfide, and a rich aqueous amine absorption solution 2162 containing hydrogen sulfide can be removed from the amine absorber unit 2160, recovered, and in some cases further processed.

The amine-treated dilute ethylene stream 2163 can be introduced into a water wash unit 2164 to remove residual amine from the amine absorber 2160 and reduce the concentration of ammonia and carbon dioxide in the dilute ethylene stream 2167. Water 2165 can be introduced to the water wash unit. The water can be slightly acidified to enhance capture of basic molecules such as the amine. An aqueous stream 2166 rich in amine, and potentially ammonia and carbon dioxide, can leave the water wash unit 2164 and may be further processed, for example as discussed herein.

Figure 22:
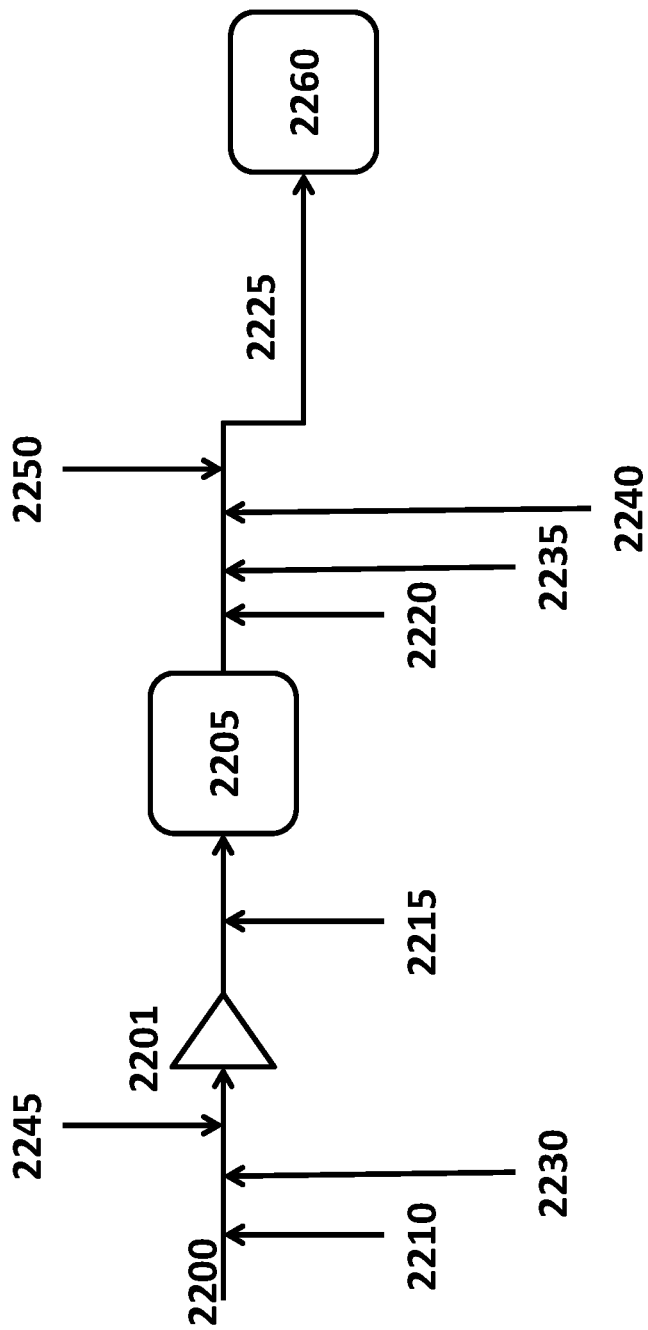
FIG. 22 shows an example of various ways of preparing an OCM feed and performing an OCM reaction using methane and olefins from the FCC.

FIG. 22 shows several approaches for preparing an OCM feed and performing an OCM reaction using methane and paraffins from an FCC. A methane-containing or paraffin-containing stream 2200 can be the product of the separations unit. The methane-containing or olefin-containing stream 2200 can be the FCC overhead gas with $H_2S$ and $CO_2$ removed or methanated and can be compressed in a compressor 2201. Additional compressors may be used. The methane-containing or paraffin-containing stream 2200 can be the FCC overhead gas with $H_2S$ and $CO_2$ removed and further reduced in a water wash unit. The methane-containing or paraffin-containing stream 2200 can be compressed in a compressor 2201. In such cases this can result in the same methane-containing or paraffin-containing stream (a first product stream) with the same composition but at a higher pressure. In some cases, one or more guard beds 2205 are located upstream and/or downstream of the compressor. In some cases, streams having methane or light paraffins (e.g., ethane and/or propane) can be added to the FCC overhead stream 2200. Examples of such methane-containing or paraffin-containing stream can be from a cumene unit, from a de-ethanizer, or from a de-propanizer in an unsaturated plant. In some cases. The methane-containing or paraffin-containing stream can be mixed with the FCC overhead before the compressor 2210 or after the compressor 2215. The methane-containing or paraffin-containing stream can be mixed with the FCC overhead before 2215 or after 2220 the guard bed(s) 2205.

One or more recycle streams can be added to the OCM feed 2225. The recycle streams can be added upstream of the compressor 2230 or downstream of the guard beds 2235. The composition of stream 2225 can be different than the composition of stream 2200. This compositional difference can be the result of removing components in the guard bed(s) 2205, addition of streams 2210, 2215, 2220, 2230, 2235, 2240, 2245, 2250, or combinations thereof. This compositional difference can be the result of removing components in the guard bed(s) 2205, addition of streams 2210, 2215, 2220, 2230, 2235, 2240, 2245, 2250, or combinations thereof.

The OCM feed stream 2225 can be sent to an OCM process 2260 and converted to olefins as described herein.

Integration of OCM with a DCU

A delayed coker unit (DCU) is a type of coker whose process comprises heating a residual oil feed to its thermal cracking temperature in a furnace with multiple parallel passes. This can crack the heavy, long chain hydrocarbon molecules of the residual oil into coker gas oil and petroleum coke. The DCU is one of the unit operations used in many oil refineries. A world scale DCU can have 1, 2, 3, 4, 5, 6, 7, 8, or more drums (e.g., each having diameters of up to about 10 meters and overall heights of up to about 43 meters). In some cases, the yield of coke from the DCU process ranges from about 18% to about 30% by weight of the feedstock residual oil. Some refineries produce as much as 2,000 to 3,000 tons or more of petroleum coke per day. Bitumen (e.g., from oil sands) is an example of a residual oil. Therefore, the present disclosure provides systems and methods for converting oil sands into olefins by OCM reactions of DCU off-gas.

Figure 23:
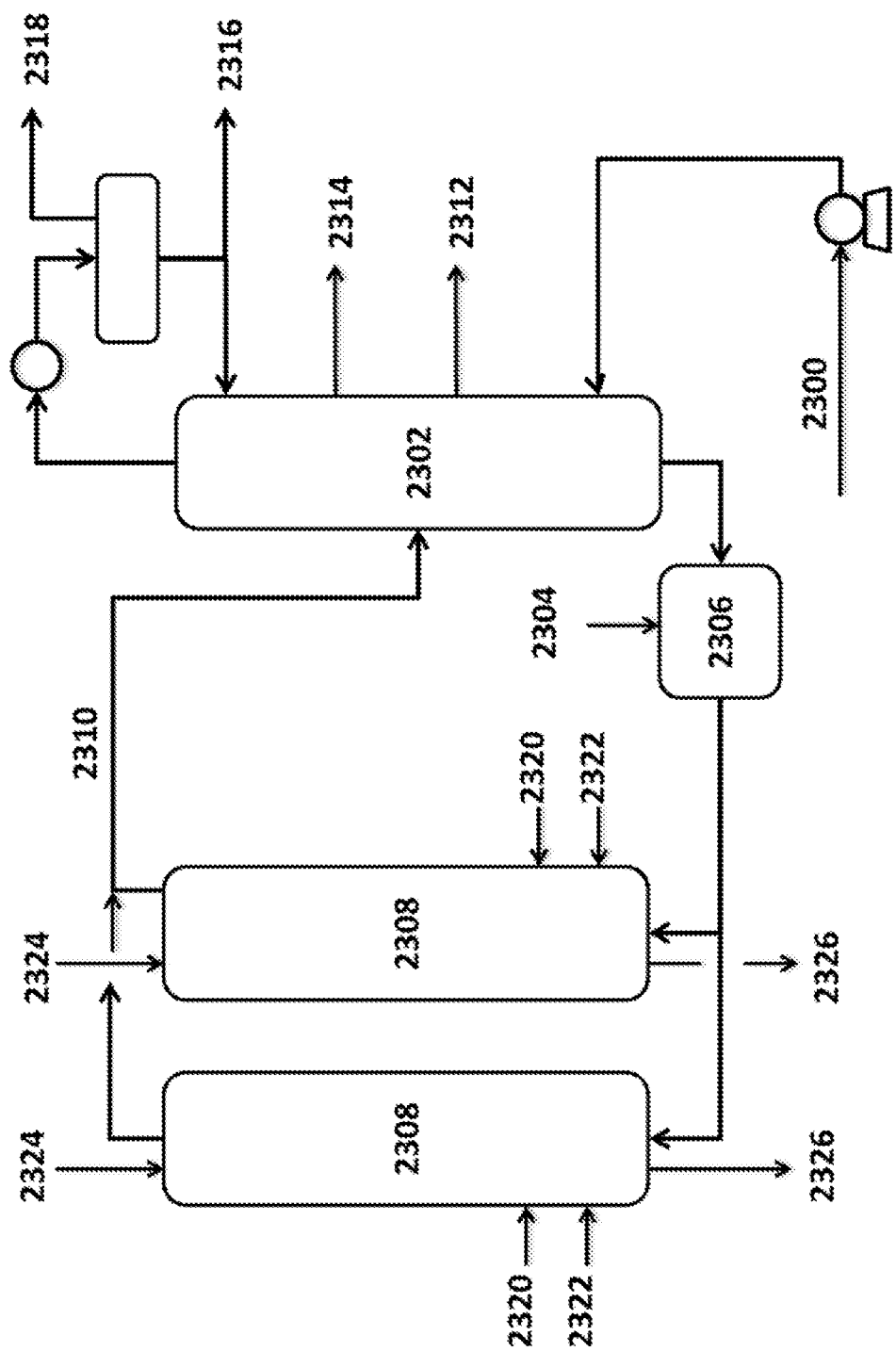
FIG. 23 shows an example of a delayed coking unit (DCU)

With reference to FIG. 23, residual oil 2300 (e.g., from the vacuum distillation unit, sometimes including high-boiling oils from other sources within the refinery) can be pumped into the bottom of the distillation column called the main fractionator 2302. From there, it can be pumped, along with some injected steam 2304, into the fuel-fired furnace 2306 and heated to its thermal cracking temperature (e.g., about 480° C.). Thermal cracking can begin in the pipe between the furnace 2306 and the coke drums 2308, and finishes in the coke drum(s) that are on-stream (the coke drums are alternately filled and emptied of coke). The injected steam 2304 can help to minimize the deposition of coke within the furnace tubes.

Pumping the incoming residual oil into the bottom of the main fractionator, rather than directly into the furnace, can preheat the residual oil by having it contact the hot vapors in the bottom of the fractionator. At the same time, some of the hot vapors can condense into a high-boiling liquid, which can be recycled back into the furnace along with the hot residual oil.

As cracking takes place in the drum, gas oil and lighter components 2310 can be generated in vapor phase and separated from the liquid and solids. The drum effluent is vapor except for any liquid or solids entrainment, and can be directed to main fractionator where it is separated into the desired boiling point fractions (e.g., heavy gas oil 2312, light gas oil 2314, coker naptha 2316, and DCU off-gas 2318).

The solid coke may be deposited and remain in the coke drum in a porous structure that may allow flow through the pores. Depending upon the overall coke drum cycle being used, a coke drum can fill in about 16 to 24 hours.

After the drum is full of the solidified coke, the hot mixture from the furnace may be switched to another drum. While the other drum is filling, the full drum may be steamed out 2320 to reduce the hydrocarbon content of the petroleum coke, and then quenched with water 2322 to cool it. The top and bottom heads of the full coke drum may be removed, and the solid petroleum coke may then be cut from the coke drum with a high-pressure water nozzle 2324, where it may fall into a pit, pad, or sluiceway for reclamation to storage 2326. In some embodiments, the coke drums 2308 operate at a pressure of about 3 to about 8 bar, the coke cutting water 2324 is injected at about 140 bar, and the DCU off-gas 2318 is withdrawn at about 2 to 3 bar (pressures absolute).

In order to simplify the present disclosure, the processing of DCU off-gas to OCM feed is described with reference to the embodiments described for FCC off-gas. Without limitation, the DCU off-gas stream 2318 can be compressed, have various streams or components added and/or have various streams or components removed prior to olefin oligomerization according to the ETL systems and methods described in FIG. 22. For example, the FCC off-gas stream 2200 of FIG. 22 can be substituted for or combined with the DCU off-gas stream 2318 of FIG. 23.

Control Systems

The present disclosure also provides computer control systems that can be employed to regulate or otherwise control the methods and systems provided herein. A control system of the present disclosure can be programmed to control process parameters, for example, temperatures, pressures in a given system such as OCM, ATR and/or or SMR subsystems.

Figure 24:
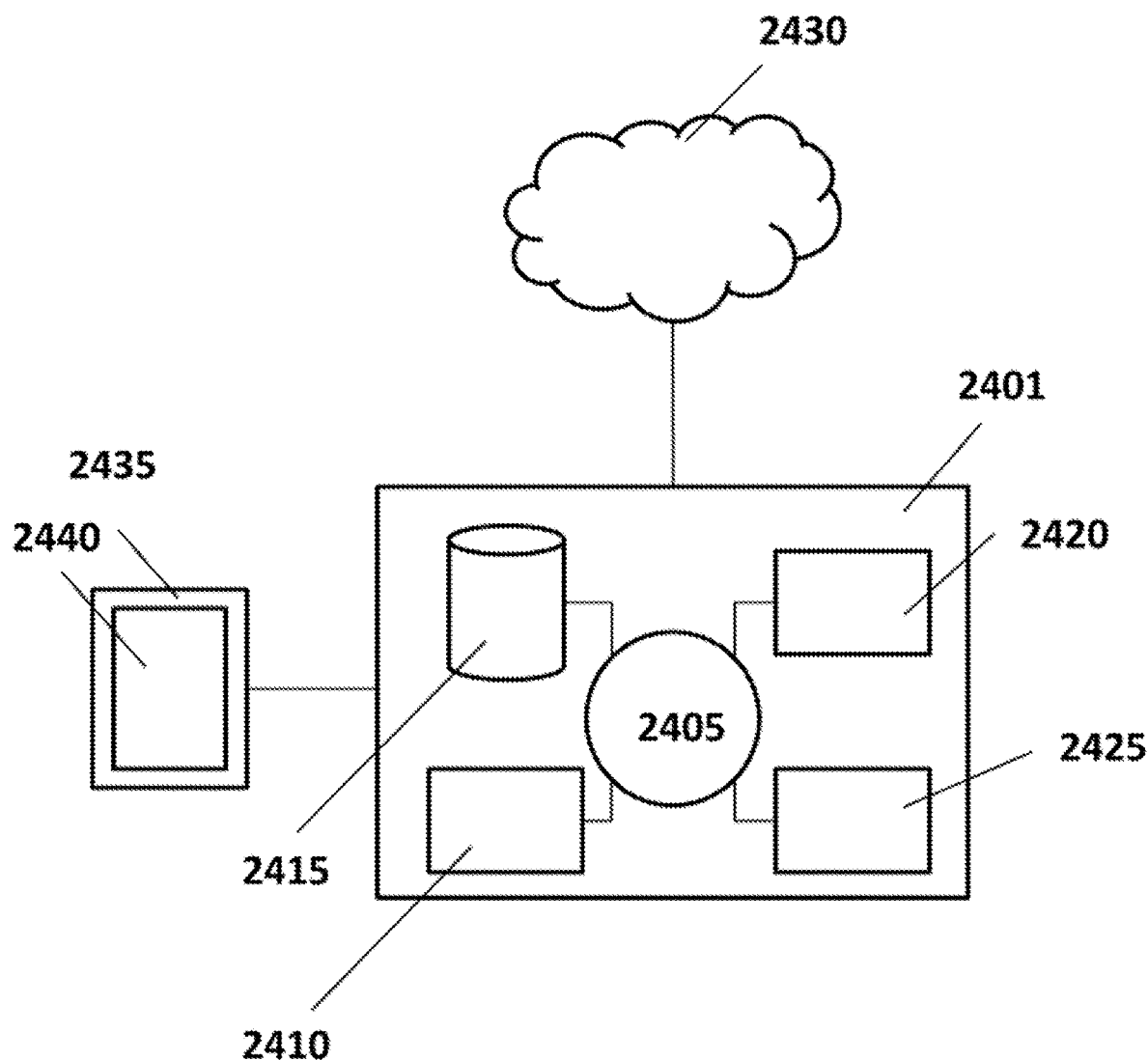
FIG. 24 schematically illustrates a computer system that is programmed or otherwise configured to implement systems and methods of the present disclosure.

FIG. 24 shows a computer system 2401 that is programmed or otherwise configured to regulate reactions or reaction conditions in various systems/subsystems such as OCM, hydrogenation, ATR, and/or SMR subsystems. The computer system 2401 can regulate, for example, fluid stream ("stream") flow rates, stream temperatures, stream pressures, reaction unit temperatures, reactor unit pressures, molar ratio between reactants, contact time of the reactant (or compounds) and reaction catalyst(s), and the quantity of products that are recycled, or directed into or out of a given system/unit.

The computer system 2401 includes a central processing unit (CPU, also "processor" and "computer processor" herein) 2405, which can be a single core or multi core processor, or a plurality of processors for parallel processing. The computer system 2401 also includes memory or memory location 2410 (e.g., random-access memory, read-only memory, flash memory), electronic storage unit 2415 (e.g., hard disk), communication interface 2420 (e.g., network adapter) for communicating with one or more other systems, and peripheral devices 2425, such as cache, other memory, data storage and/or electronic display adapters. The memory 2410, storage unit 2415, interface 2420 and peripheral devices 2425 are in communication with the CPU 2405 through a communication bus (solid lines), such as a motherboard. The storage unit 2415 can be a data storage unit (or data repository) for storing data.

The CPU 2405 can execute a sequence of machine-readable instructions, which can be embodied in a program or software. The instructions may be stored in a memory location, such as the memory 2410. Examples of operations performed by the CPU 2405 can include fetch, decode, execute, and writeback. The CPU 2405 can be part of a circuit, such as an integrated circuit. One or more other components of the system 2401 can be included in the circuit. In some cases, the circuit is an application specific integrated circuit (ASIC).

The storage unit 2415 can store files, such as drivers, libraries and saved programs. The storage unit 2415 can store programs generated by users and recorded sessions, as well as output(s) associated with the programs. The storage unit 2415 can store user data, e.g., user preferences and user programs. The computer system 2401 in some cases can include one or more additional data storage units that are external to the computer system 2401, such as located on a remote server that is in communication with the computer system 2401 through an intranet or the Internet. The computer system 2401 can communicate with one or more remote computer systems through the network 2430.

Methods as described herein can be implemented by way of machine (e.g., computer processor) executable code stored on an electronic storage location of the computer system 2401, such as, for example, on the memory 2410 or electronic storage unit 2415. The machine executable or machine readable code can be provided in the form of software. During use, the code can be executed by the processor 2405. In some cases, the code can be retrieved from the storage unit 2415 and stored on the memory 2410 for ready access by the processor 2405. In some situations, the electronic storage unit 2415 can be precluded, and machine-executable instructions are stored on memory 2410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2401, can be embodied in programming. Various aspects of the technology may be thought of as "products" or "articles of manufacture" in some cases in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2401 can include or be in communication with an electronic display 2435 that comprises a user interface (UI) 2440 for providing, for example, signals from a chip with time. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2405.

It will be appreciated that systems and methods described herein are provided as examples and that various alternatives may be employed. It will be further appreciated that components of systems described herein are interchangeable.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for producing propylene, the method comprising:
    (a) injecting a first stream containing methane ($CH_4$) and a second stream containing an oxidizing agent into an oxidative coupling of methane (OCM) reactor at a temperature of at least about 400° C. and a pressure of at least about 3 bar(g) to produce an OCM product stream comprising ethylene, propylene, propane, and unconverted methane ($CH_4$);
    (b) fractionating the OCM product stream using one or more separation units to generate (i) a third stream comprising ethylene and (ii) a fourth stream comprising propylene and propane;
    (c) injecting at least a portion of the fourth stream into an additional separation unit to generate a propylene stream and a propane stream;
    (d) injecting at least a portion of the propane stream into a propane dehydrogenation (PDH) unit to generate a PDH effluent comprising propylene, methane, and hydrogen;
    (e) seperating the PDH effluent into a fifth stream comprising propylene, a sixth stream comprising methane, and a seventh stream comprising hydrogen;
    (f) injecting at least a portion of the sixth stream into the OCM reactor;
    (g) injecting at least a portion of the third stream into a dimerization reactor to produce a butene stream, wherein less than about 50% of said butene stream is isobutene; and
    (h) injecting said butene stream into a metathesis reactor to produce an effluent stream comprising propylene and unconverted butene.

2. The method of claim 1, wherein (e) and (f) are performed in a single vessel.

3. The method of claim 1, wherein the dimerization and the metathesis are performed in a single reactor or over a single catalyst.

4. The method of claim 1, wherein at least about 50% of said butene stream is 1-butene or 2-butene.

5. The method of claim 1, wherein a portion of the ethylene produced in the OCM reactor is injected into the dimerization reactor, and an additional portion of the ethylene produced in the OCM reactor is injected into the metathesis reactor.

6. The method of claim 5, wherein about 70% of the ethylene produced in the OCM reactor is injected into the dimerization reactor, and about 30% of the ethylene produced in the OCM reactor is injected into the metathesis reactor.

7. The method of claim 1, wherein substantially no ethylene is injected into the metathesis reactor without first being injected into the dimerization reactor.

8. The method of claim 7, wherein the ethylene that is injected into the dimerization reactor has a purity of at least about 99.5 mol %.

9. The method of claim 8, wherein at least about 95% of the ethylene that is injected into the dimerization reactor is converted into butenes.

10. The method of claim 1, wherein the butene stream produced in the dimerization reactor contains $C_{5+}$ compounds, and wherein said $C_{5+}$ compounds are removed using a de-butanizer prior to (f).

11. The method of claim 1, wherein ethylene is separated from $C_{3+}$ components in the effluent stream of the metathesis reactor.

12. The method of claim 11, wherein a portion of the separated ethylene is recycled to the metathesis reactor.

13. The method of claim 1, wherein the propylene in the effluent stream of the metathesis reactor is separated from the unconverted butene.

14. The method of claim 13, wherein the unconverted butene is recycled to the metathesis reactor.

15. The method of claim 1, wherein the butene that is injected into the metathesis reactor further comprises unconverted ethylene, which unconverted ethylene is passed through the dimerization reactor without being converted to butene.

16. The method of claim 15, wherein the unconverted ethylene is about the only ethylene that is injected into the metathesis reactor.

17. The method of claim 1, wherein the unconverted methane from the OCM product stream is removed through a vacuum pressure swing adsorption (VPSA) process to produce a VPSA effluent stream that contains less than about 1% methane.

18. The method of claim 17, wherein the VPSA effluent stream is injected into a distillation column that removes $C_{3+}$ species to generate a distillation effluent stream that has a higher concentration of ethylene than the VPSA effluent stream.

* * * * *